(12) United States Patent
Wenchell et al.

(10) Patent No.: US 8,113,408 B2
(45) Date of Patent: Feb. 14, 2012

(54) SURGICAL STAPLING DEVICE

(75) Inventors: Thomas Wenchell, Durham, CT (US); Stanislaw Marczyk, Stratford, CT (US); Kenneth H. Whitfield, New Haven, CT (US); Roman Czernik, Trumbull, CT (US); Henry E. Holsten, Southington, CT (US); Frank C. Maffei, Shelton, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 13/008,284

(22) Filed: Jan. 18, 2011

(65) Prior Publication Data
US 2011/0163148 A1  Jul. 7, 2011

Related U.S. Application Data

(63) Continuation of application No. 12/732,366, filed on Mar. 26, 2010, now Pat. No. 8,033,440, which is a continuation of application No. 12/500,062, filed on Jul. 9, 2009, now Pat. No. 7,891,534, which is a continuation of application No. 12/036,659, filed on Feb. 25, 2008, now Pat. No. 7,934,628, which is a continuation of application No. 10/490,790, filed as application No. PCT/US02/32031 on Oct. 4, 2002.

(60) Provisional application No. 60/363,502, filed on Mar. 11, 2002, provisional application No. 60/363,487, filed on Mar. 11, 2002, provisional application No. 60/327,527, filed on Oct. 5, 2001.

(51) Int. Cl.
*A61B 17/0025* (2006.01)
(52) U.S. Cl. ............. 227/176.1; 227/19; 227/175.1
(58) Field of Classification Search ............ 227/19, 227/175.1, 178.1, 176.1
See application file for complete search history.

(56) References Cited

U.S. PATENT DOCUMENTS
3,079,606 A  3/1963  Bobrov et al.
(Continued)

FOREIGN PATENT DOCUMENTS
DE  2744824  2/1980
(Continued)

*Primary Examiner* — Rinaldi Rada
*Assistant Examiner* — Nathaniel Chukwurah

(57) ABSTRACT

A surgical stapling device for sequentially applying a plurality of fasteners to body tissue and simultaneously incising tissue is provided. The surgical stapling device is adapted to receive disposable loading units having staples in linear rows whose length can be between about 30 mm and 60 mm. The disposable loading unit includes a proximal body portion, a mounting assembly and a tool assembly. The mounting assembly is secured to the proximal end of the tool assembly and pivotally mounted about a pivot axis to the distal end of the proximal body portion. A support member or blow-out plate assembly is positioned on opposite sides of the pivot avis and extends between the proximal body portion and the mounting assembly. An axial drive assembly is slidably positioned between the support members and is translatable through the cartridge assembly to eject staples from the cartridge assembly. The support members prevent outward buckling of the axial drive assembly during actuation of the device especially when the tool assembly is articulated. Preferably, a protrusion is provided in the proximal body portion of the disposable loading unit at a position to frictionally engage an articulation link. Engagement between the protrusion and the articulation link retains the articulation link at a fixed position within the proximal body portion to maintain the tool assembly in a desired orientation until a predetermined axial force is applied to the articulation link. The disposable loading unit also preferably includes a locking member which is operably connected to the axial drive assembly. The locking member provides an audible and/or tactile indication that the device has been actuated.

8 Claims, 64 Drawing Sheets

U.S. PATENT DOCUMENTS

| | | | |
|---|---|---|---|
| 3,490,675 A | 1/1970 | Green et al. | |
| 4,429,695 A | 2/1984 | Green | |
| 4,505,414 A | 3/1985 | Filipi | |
| 4,589,413 A | 5/1986 | Malyshev et al. | |
| 4,602,634 A | 7/1986 | Barkley | |
| 4,608,981 A | 9/1986 | Rothfuss et al. | |
| 4,610,383 A | 9/1986 | Rothfuss et al. | |
| 4,633,861 A | 1/1987 | Chow et al. | |
| 4,633,874 A | 1/1987 | Chow et al. | |
| 4,671,445 A | 6/1987 | Barker et al. | |
| 4,703,887 A | 11/1987 | Clanton et al. | |
| 4,728,020 A | 3/1988 | Green et al. | |
| 4,784,137 A | 11/1988 | Kulik et al. | |
| 4,863,088 A | 9/1989 | Redmond et al. | |
| 4,892,244 A | 1/1990 | Fox et al. | |
| 4,991,764 A | 2/1991 | Mericle | |
| 5,040,715 A | 8/1991 | Green et al. | |
| 5,065,929 A | 11/1991 | Schulze et al. | |
| 5,074,454 A | 12/1991 | Peters | |
| 5,083,695 A | 1/1992 | Foslien et al. | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,170,925 A | 12/1992 | Madden et al. | |
| RE34,519 E | 1/1994 | Fox et al. | |
| 5,307,976 A | 5/1994 | Olson et al. | |
| 5,312,023 A * | 5/1994 | Green et al. | 227/175.1 |
| 5,318,221 A | 6/1994 | Green et al. | |
| 5,326,013 A | 7/1994 | Green et al. | |
| 5,332,142 A | 7/1994 | Robinson et al. | |
| 5,364,003 A | 11/1994 | Williamson, IV | |
| 5,376,095 A | 12/1994 | Ortiz | |
| 5,381,943 A | 1/1995 | Allen et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,407,293 A | 4/1995 | Crainich | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,431,323 A | 7/1995 | Smith et al. | |
| 5,433,721 A | 7/1995 | Hooven et al. | |
| 5,447,265 A | 9/1995 | Vidal et al. | |
| 5,452,837 A | 9/1995 | Williamson, IV et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,474,566 A | 12/1995 | Alesi et al. | |
| 5,484,451 A | 1/1996 | Akopov et al. | |
| 5,485,947 A | 1/1996 | Olson et al. | |
| 5,487,500 A | 1/1996 | Knodel et al. | |
| 5,489,058 A | 2/1996 | Plyley et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,937 A | 7/1996 | Boiarski et al. | |
| 5,551,622 A | 9/1996 | Yoon | |
| 5,553,765 A | 9/1996 | Knodel et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,573,543 A | 11/1996 | Akopov et al. | |
| 5,577,654 A | 11/1996 | Bishop | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bitner et al. | |
| 5,676,674 A | 10/1997 | Bolanos et al. | |
| 5,680,982 A | 10/1997 | Schulze et al. | |
| 5,690,269 A | 11/1997 | Bolanos et al. | |
| 5,692,668 A | 12/1997 | Schulze et al. | |
| 5,697,542 A | 12/1997 | Knodel et al. | |
| 5,704,534 A | 1/1998 | Huitema et al. | |
| 5,709,334 A | 1/1998 | Sorrentino et al. | |
| 5,711,472 A | 1/1998 | Bryan | |
| 5,713,505 A | 2/1998 | Huitema | |
| 5,716,366 A | 2/1998 | Yates | |
| 5,728,110 A | 3/1998 | Vidal et al. | |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,256 A | 6/1998 | Mastri et al. | |
| 5,769,303 A | 6/1998 | Knodel et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,826,776 A | 10/1998 | Schultze et al. | |
| 5,829,662 A | 11/1998 | Allen et al. | |
| 5,833,695 A | 11/1998 | Yoon | |
| 5,836,147 A | 11/1998 | Schnipke | |
| 5,862,972 A | 1/1999 | Green et al. | |
| 5,865,361 A | 2/1999 | Milliman et al. | |
| 5,871,135 A | 2/1999 | Williamson, IV et al. | |
| 5,897,562 A | 4/1999 | Bolanos et al. | |
| 5,901,895 A | 5/1999 | Heaton et al. | |
| 5,911,353 A | 6/1999 | Bolanos et al. | |
| 5,918,791 A | 7/1999 | Sorrentino et al. | |
| 5,954,259 A | 9/1999 | Viola et al. | |
| 6,004,335 A | 12/1999 | Vaitekunas et al. | |
| 6,010,054 A | 1/2000 | Johnson et al. | |
| 6,032,849 A | 3/2000 | Mastri et al. | |
| 6,079,606 A | 6/2000 | Milliman et al. | |
| 6,109,500 A | 8/2000 | Alli et al. | |
| 6,197,017 B1 | 3/2001 | Brock et al. | |
| 6,202,914 B1 | 3/2001 | Geiste et al. | |
| 6,241,139 B1 * | 6/2001 | Milliman et al. | 227/175.1 |

| | | |
|---|---|---|
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,439,446 B1 | 8/2002 | Perry et al. |
| 6,443,973 B1 | 9/2002 | Whitman |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,656,193 B2 | 12/2003 | Grant et al. |
| 6,669,073 B2 | 12/2003 | Milliman et al. |
| 6,698,643 B2 | 3/2004 | Whitman |
| 6,722,552 B2 | 4/2004 | Fenton, Jr. |

FOREIGN PATENT DOCUMENTS

| | | |
|---|---|---|
| DE | 2903159 | 7/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2070499 | 9/1981 |
| GB | 2141066 | 12/1984 |
| GB | 2165559 | 4/1986 |
| RU | 980703 | 12/1982 |
| RU | 990220 | 1/1983 |
| SU | 728848 | 5/1977 |
| SU | 659146 | 4/1979 |
| WO | WO 83/02247 | 7/1983 |
| WO | WO 89/10094 | 11/1989 |
| WO | WO 92/10976 | 7/1992 |
| WO | WO 93/08754 | 5/1993 |
| WO | WO 93/14706 | 8/1993 |

* cited by examiner

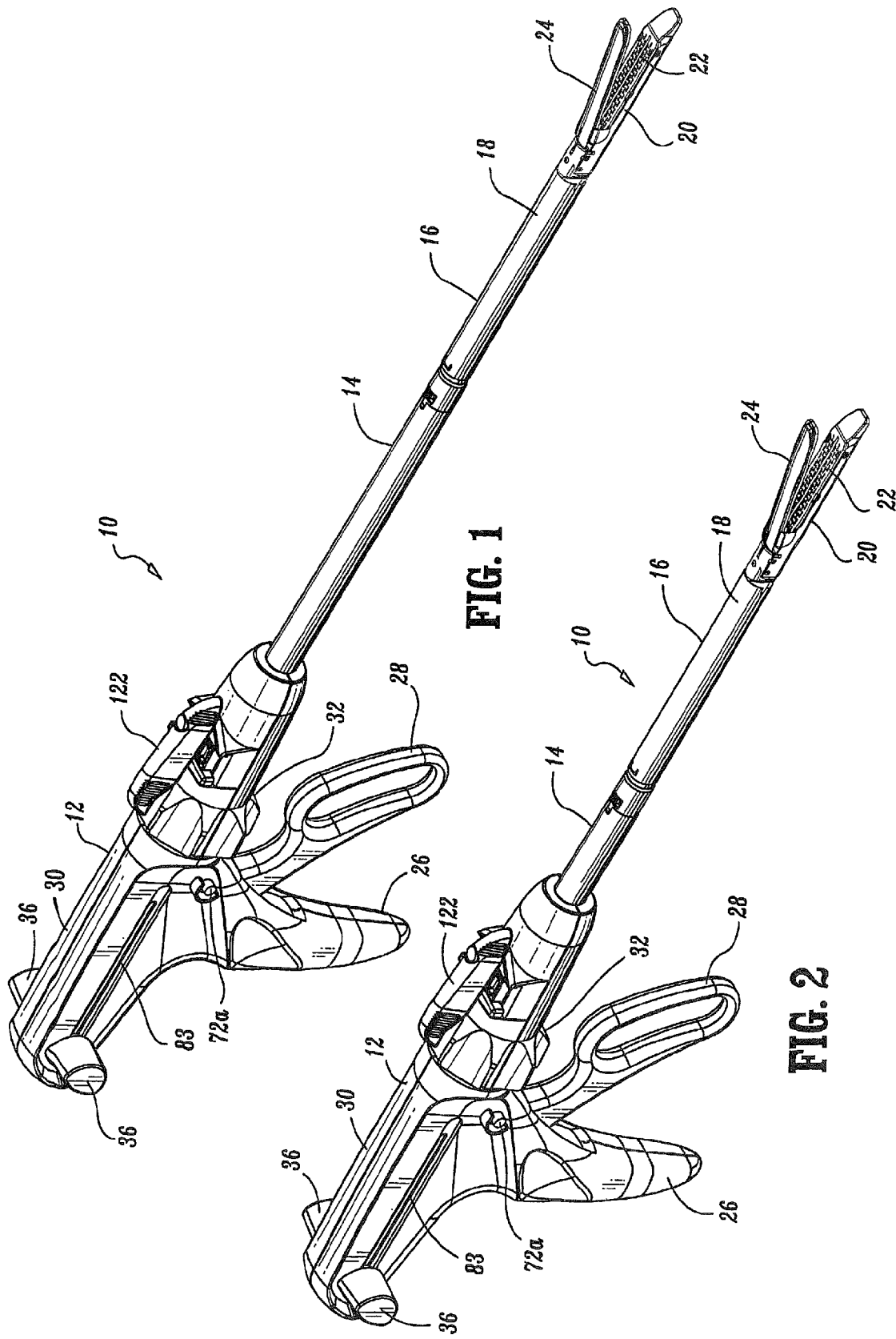

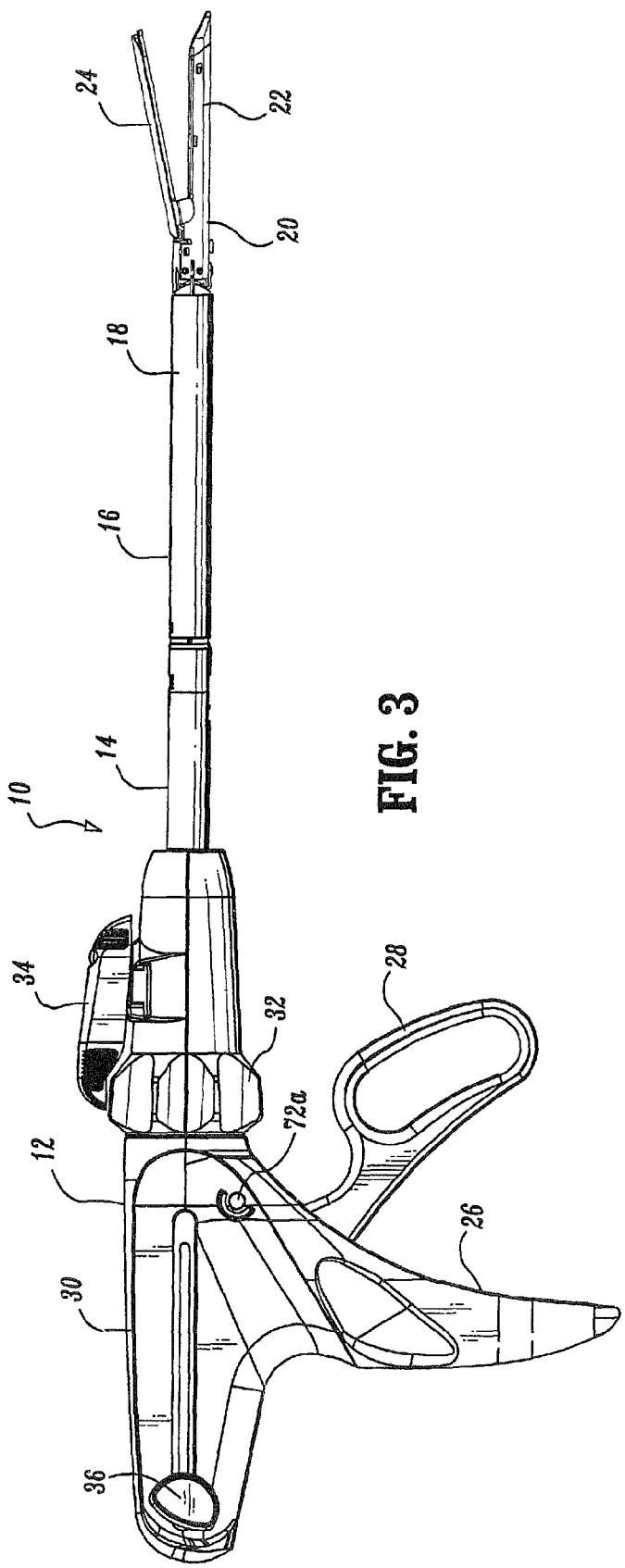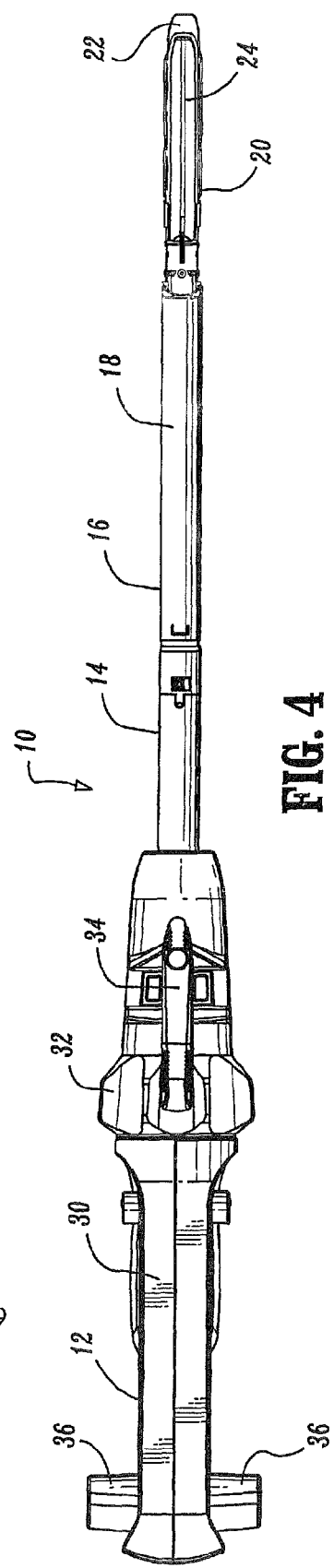

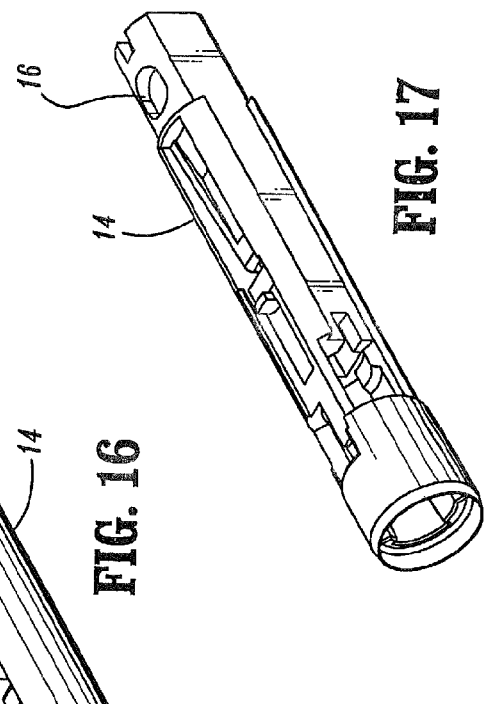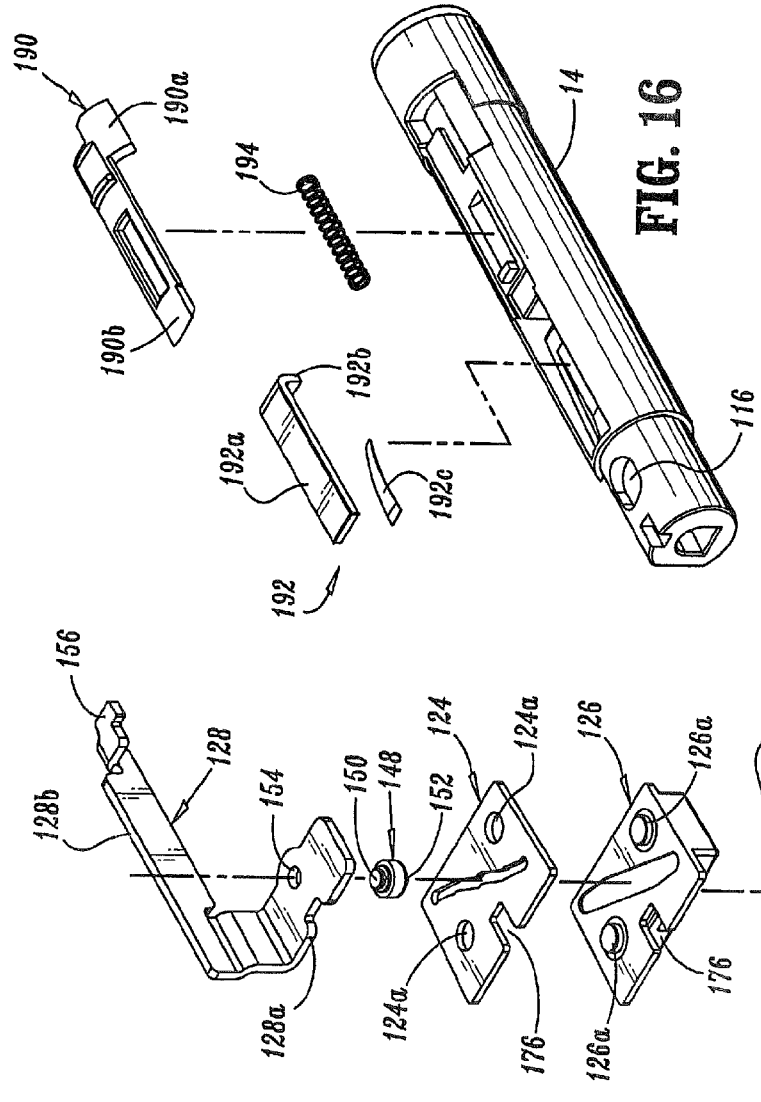

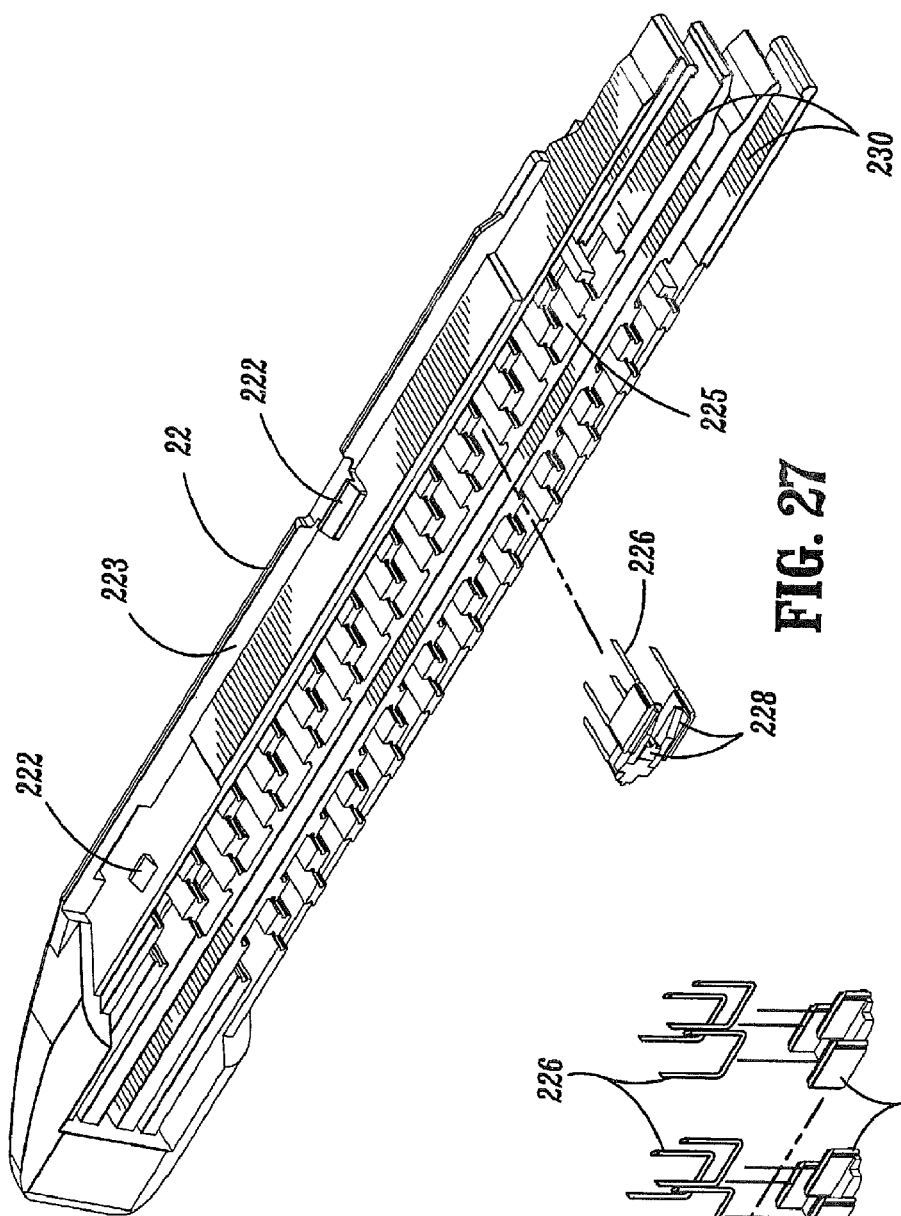
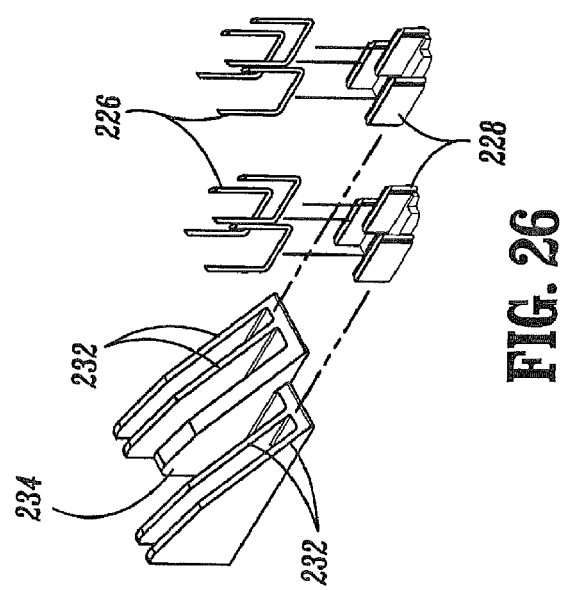
FIG. 27
FIG. 26

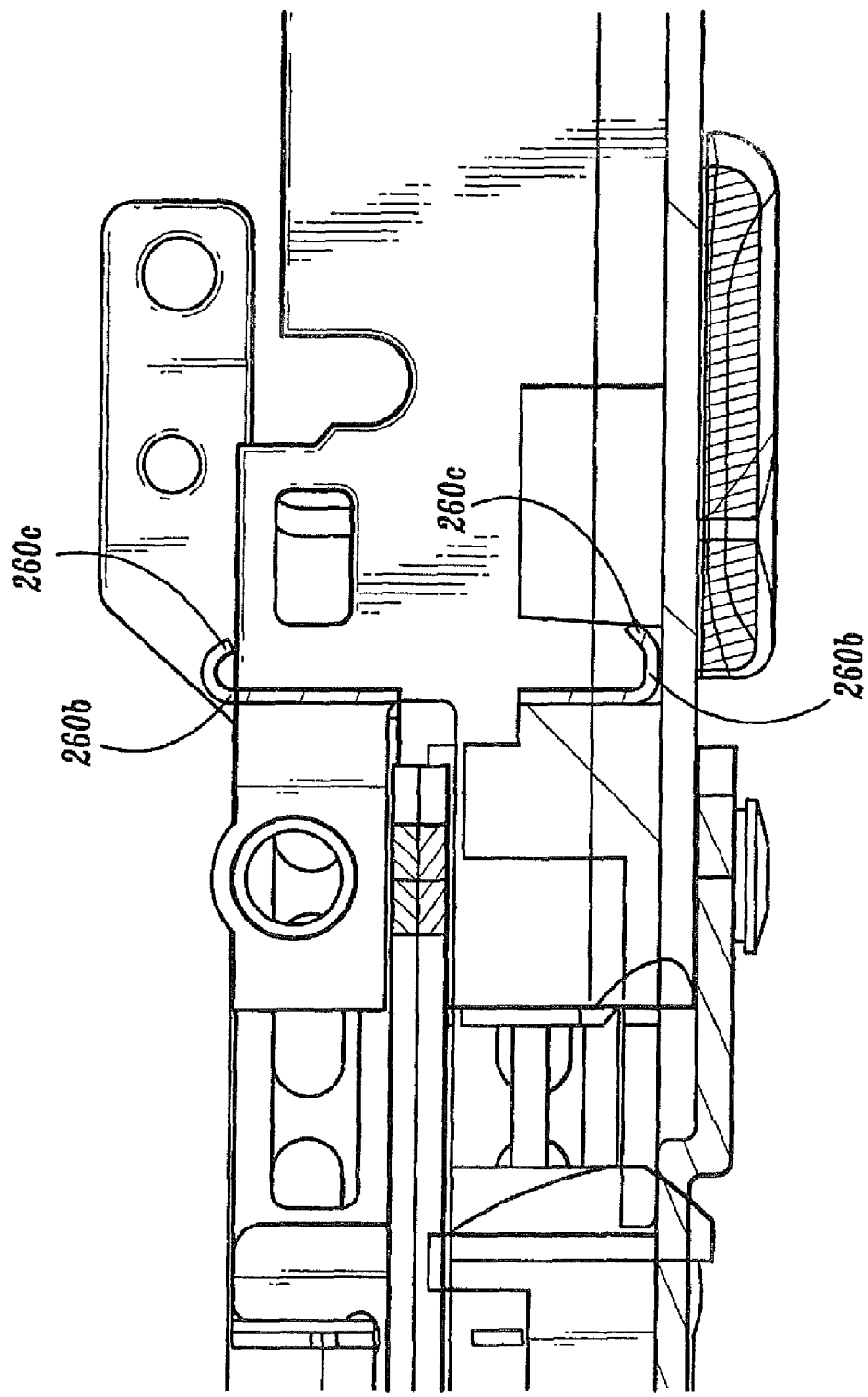

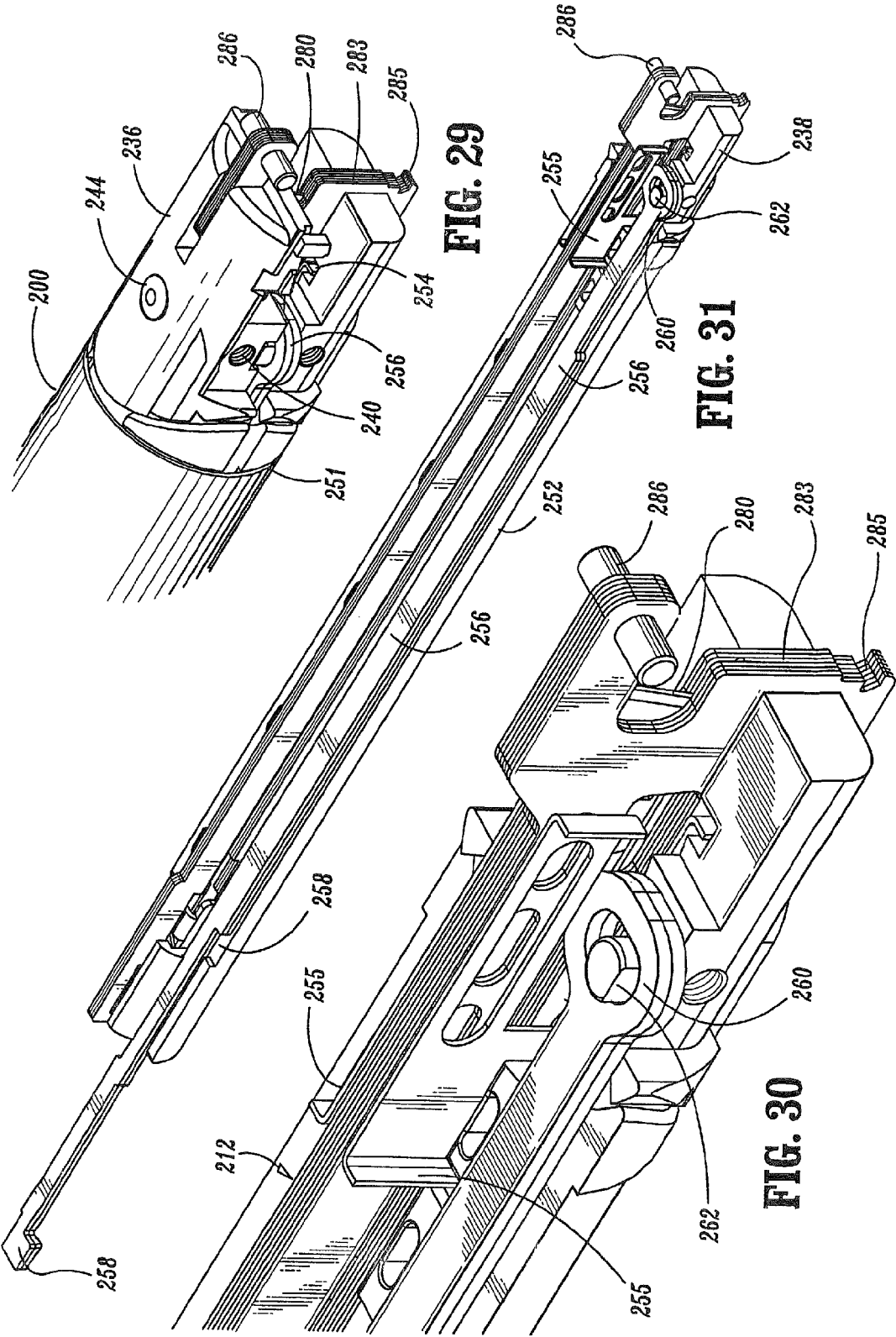

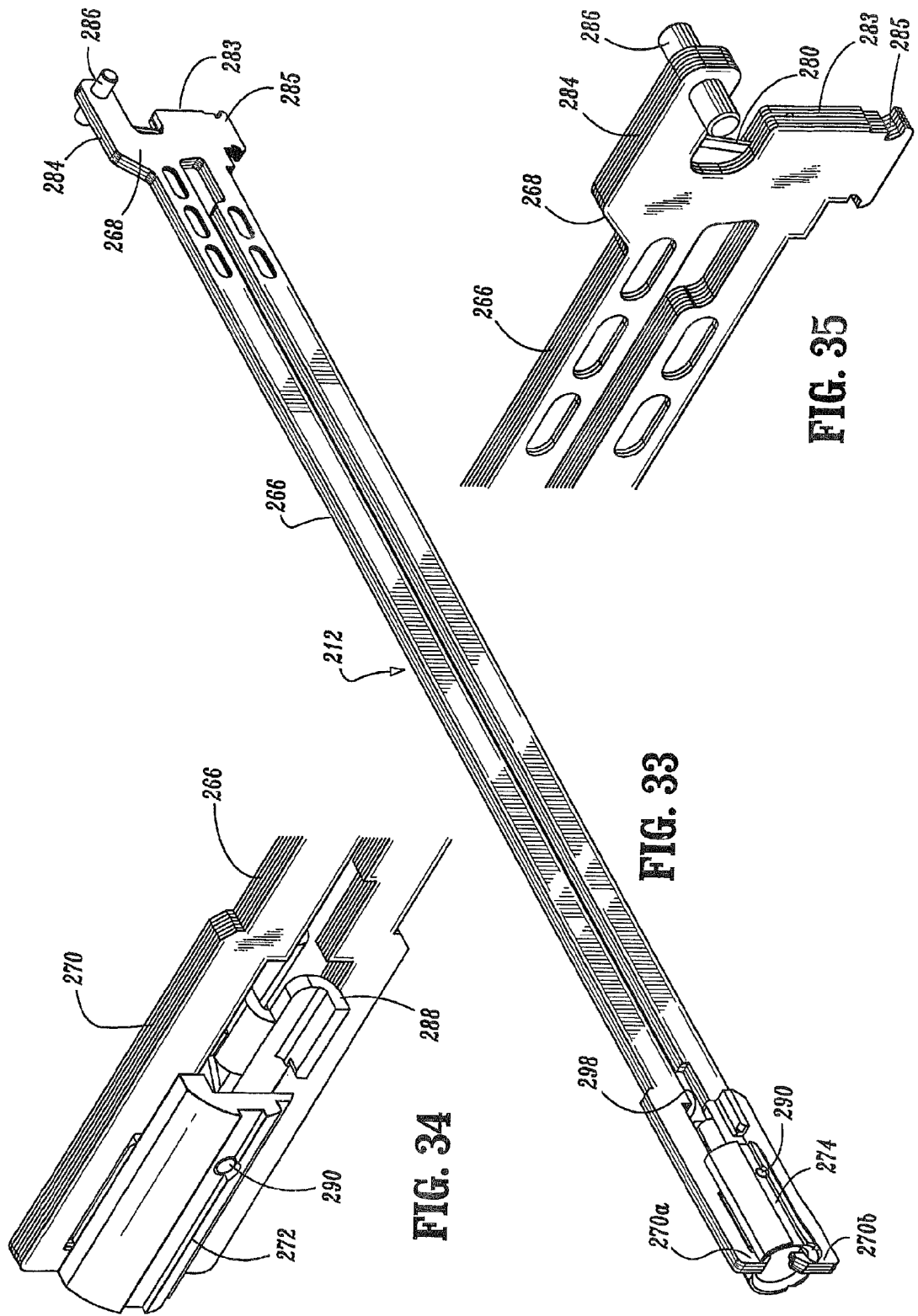

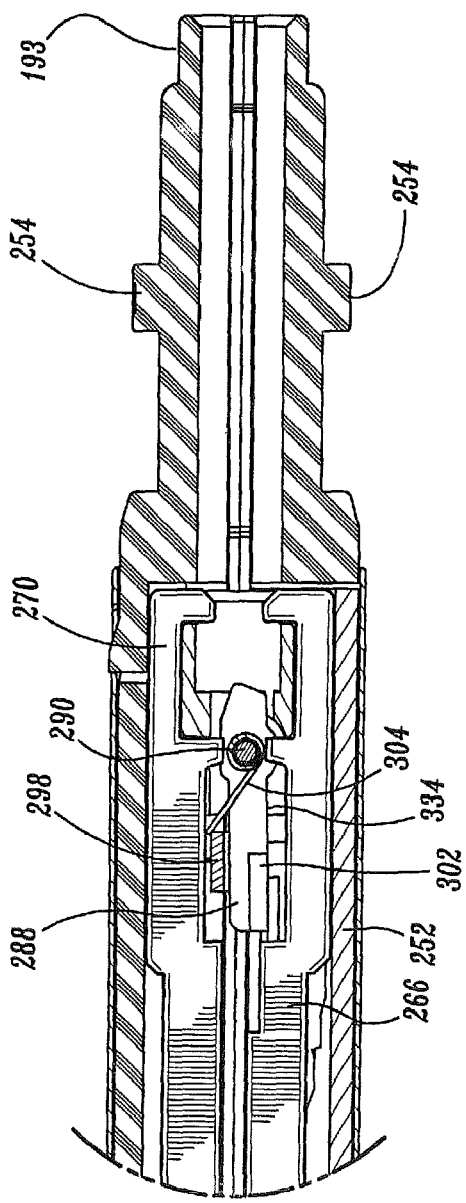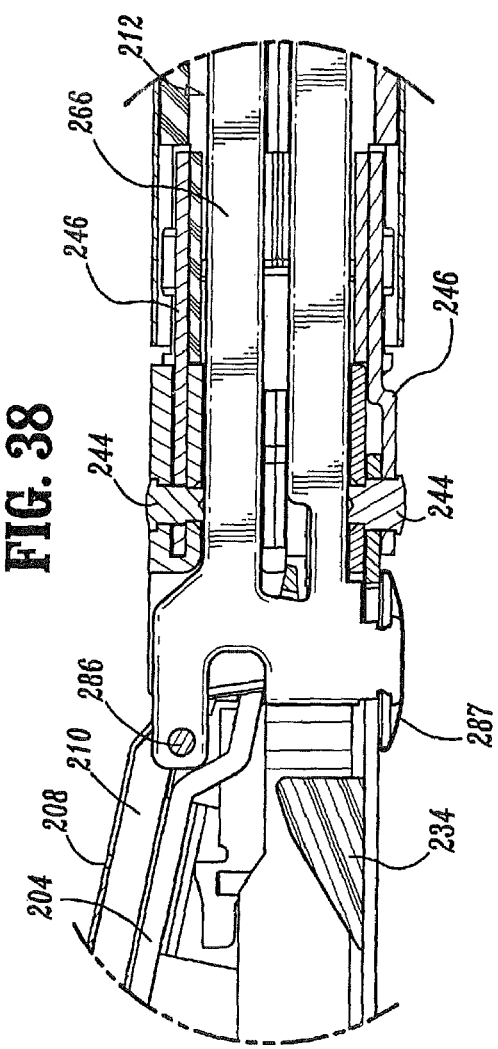

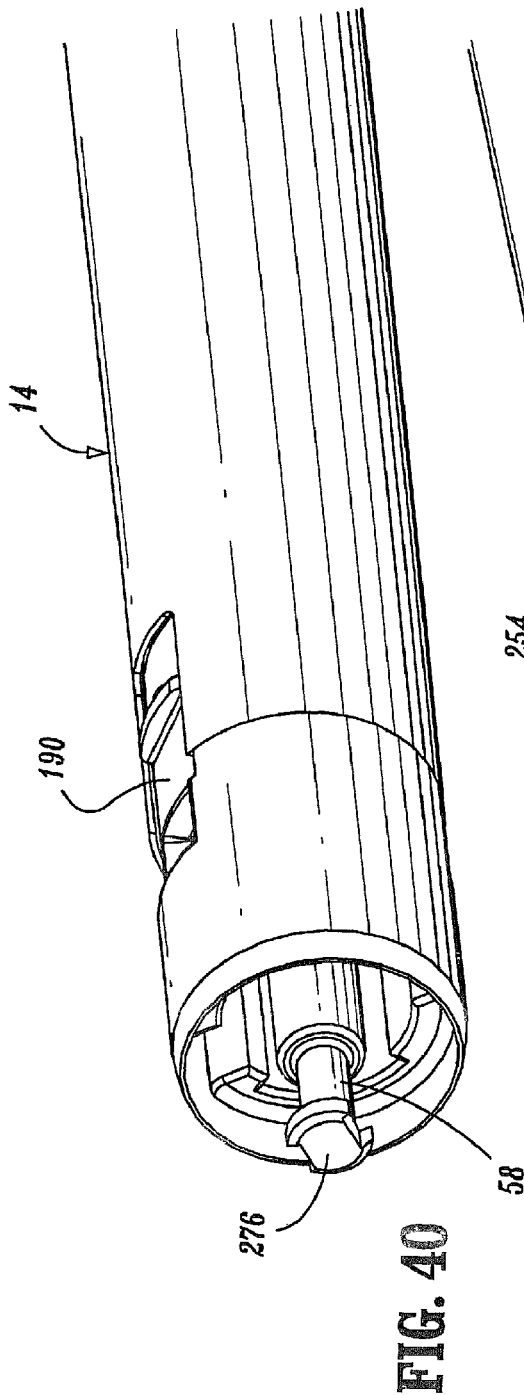
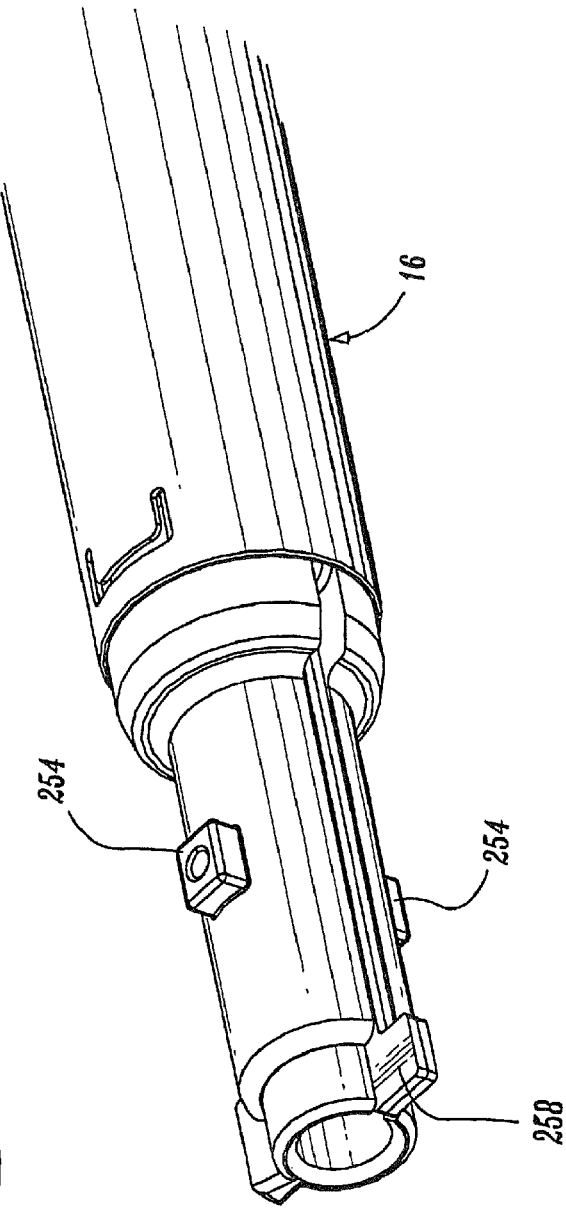

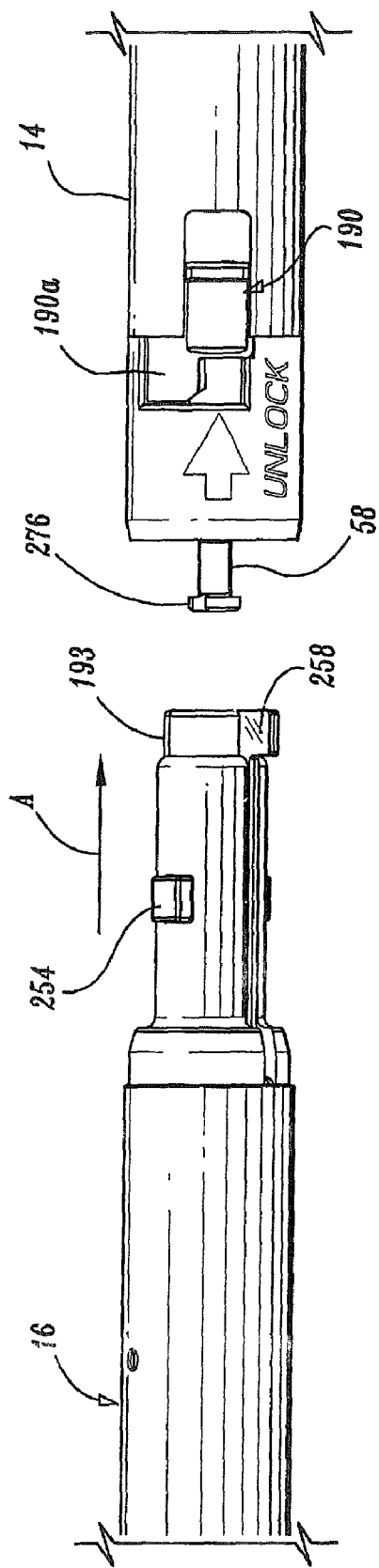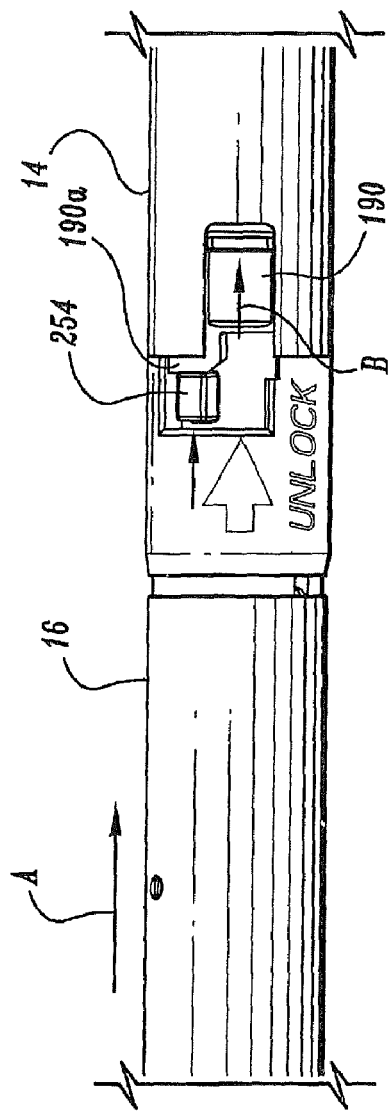
FIG. 42
FIG. 43

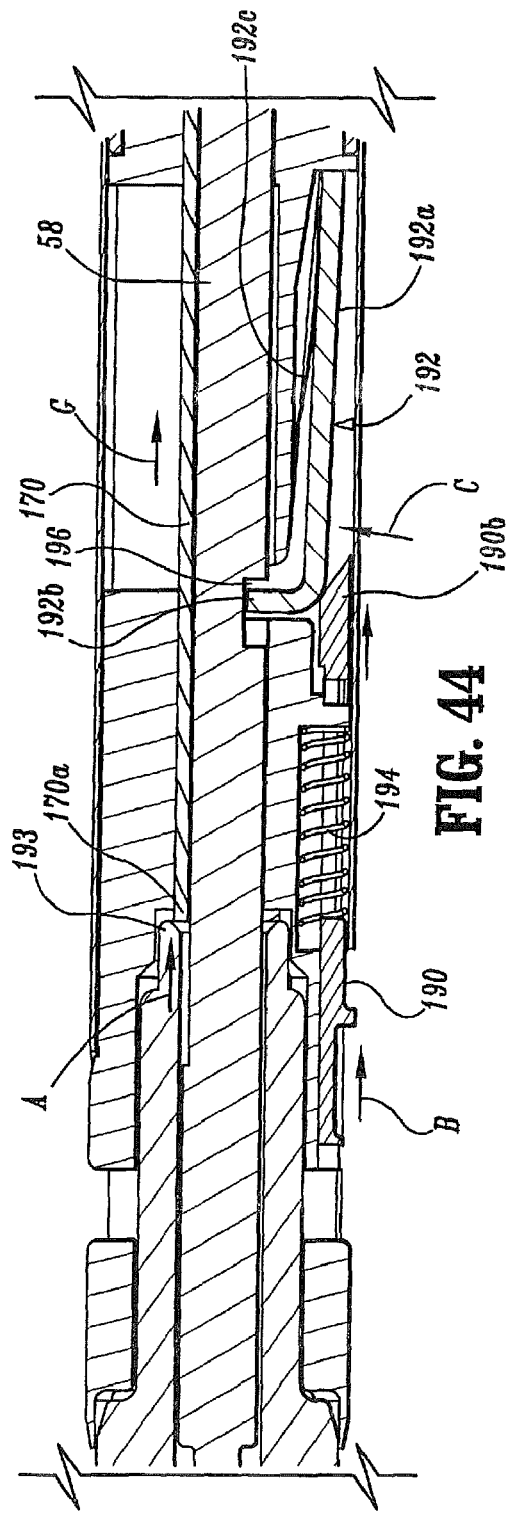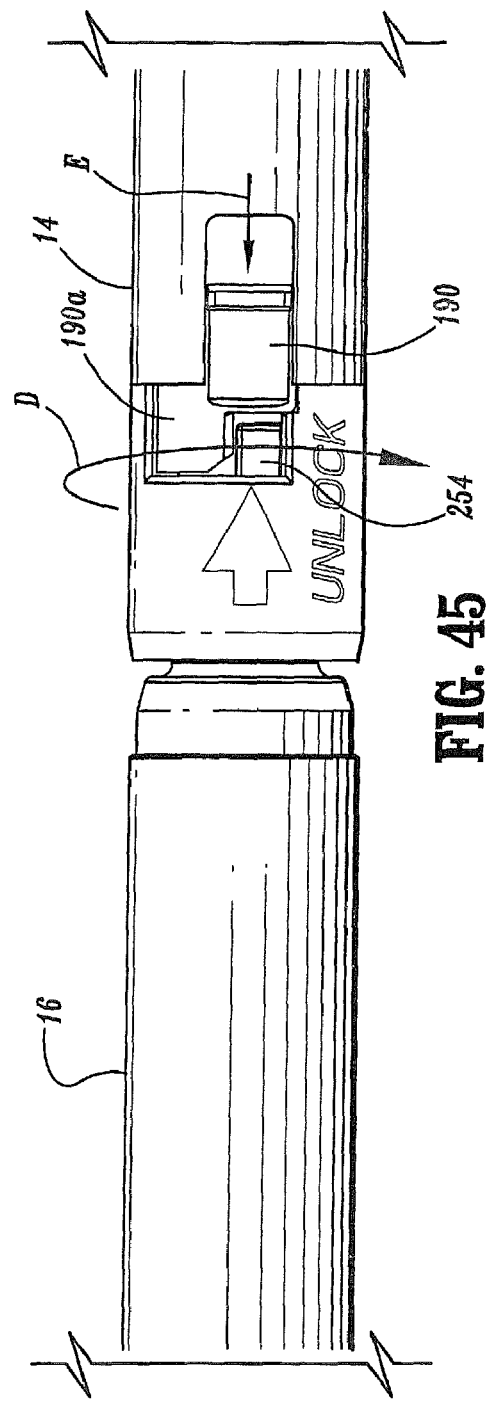

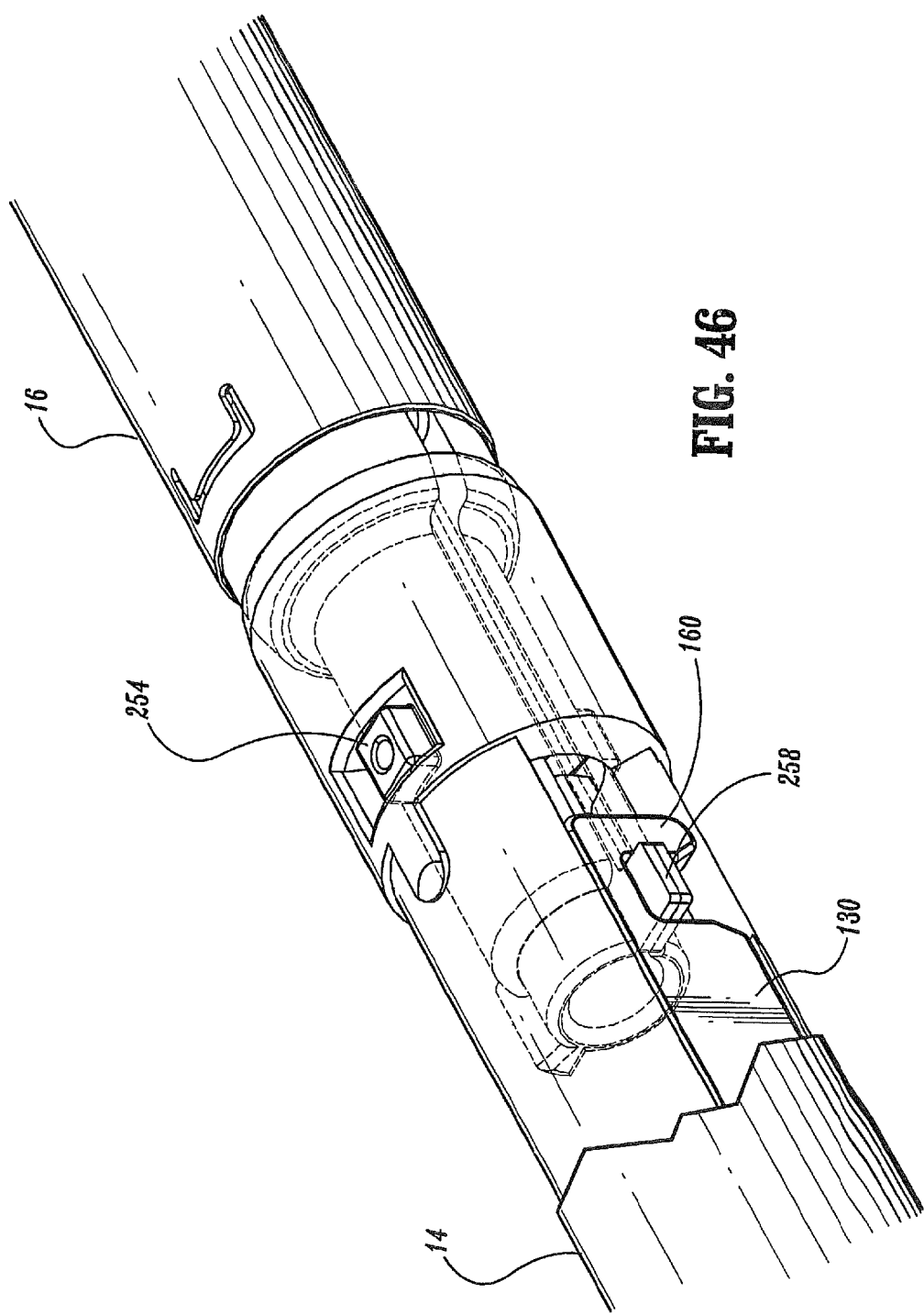

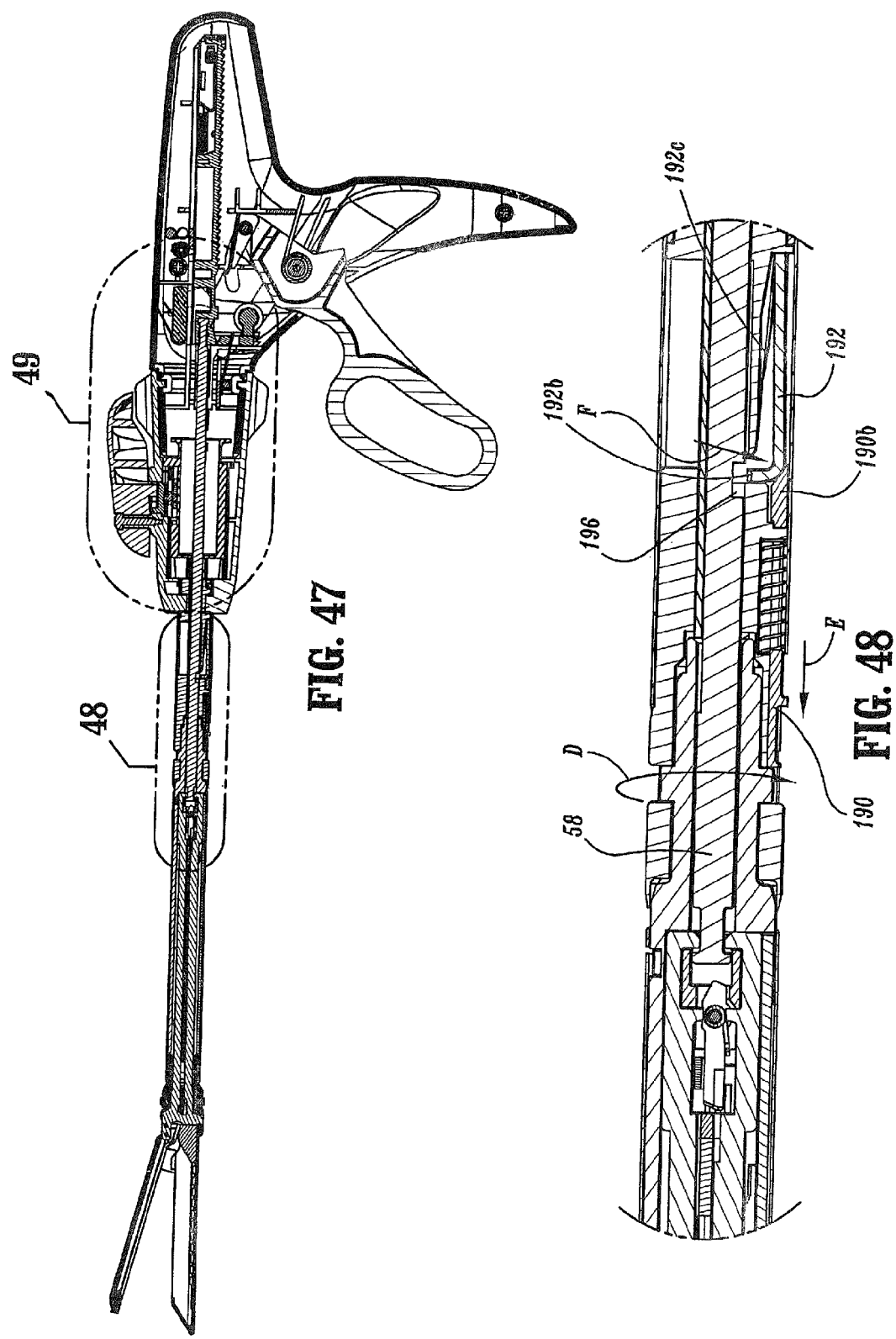

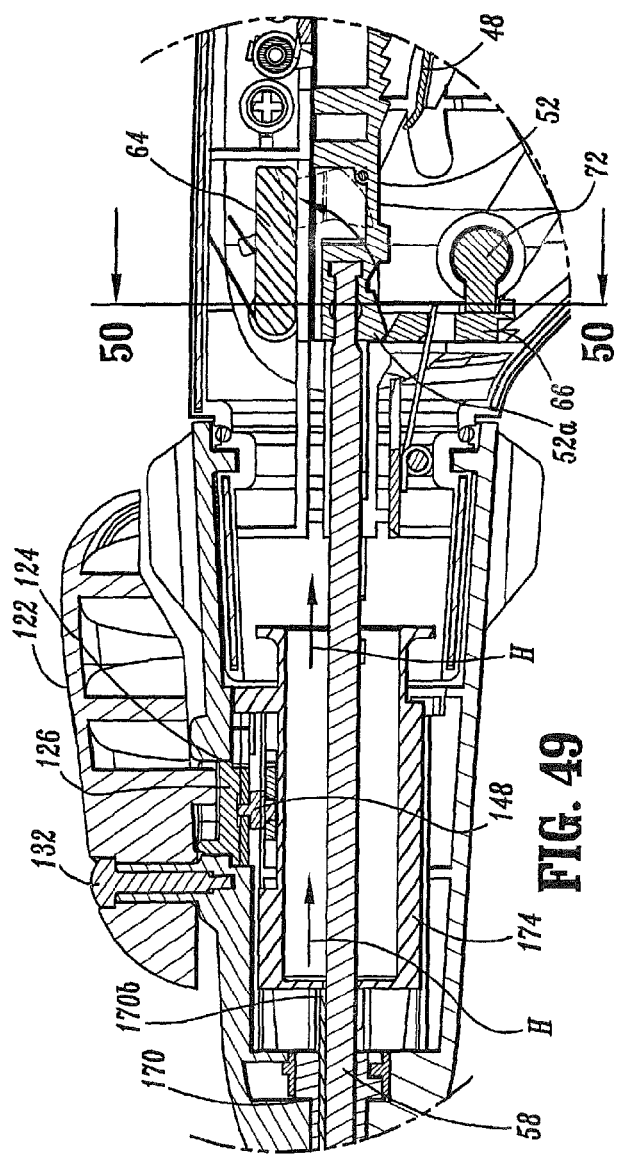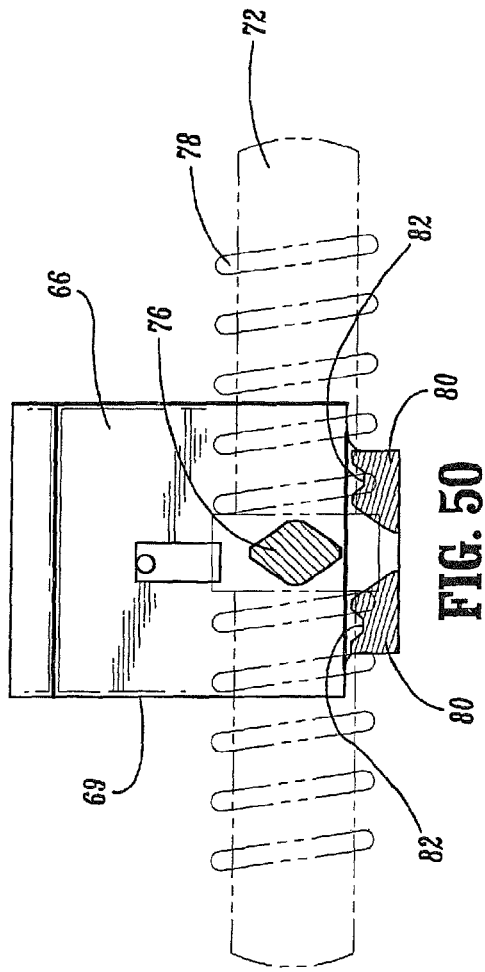

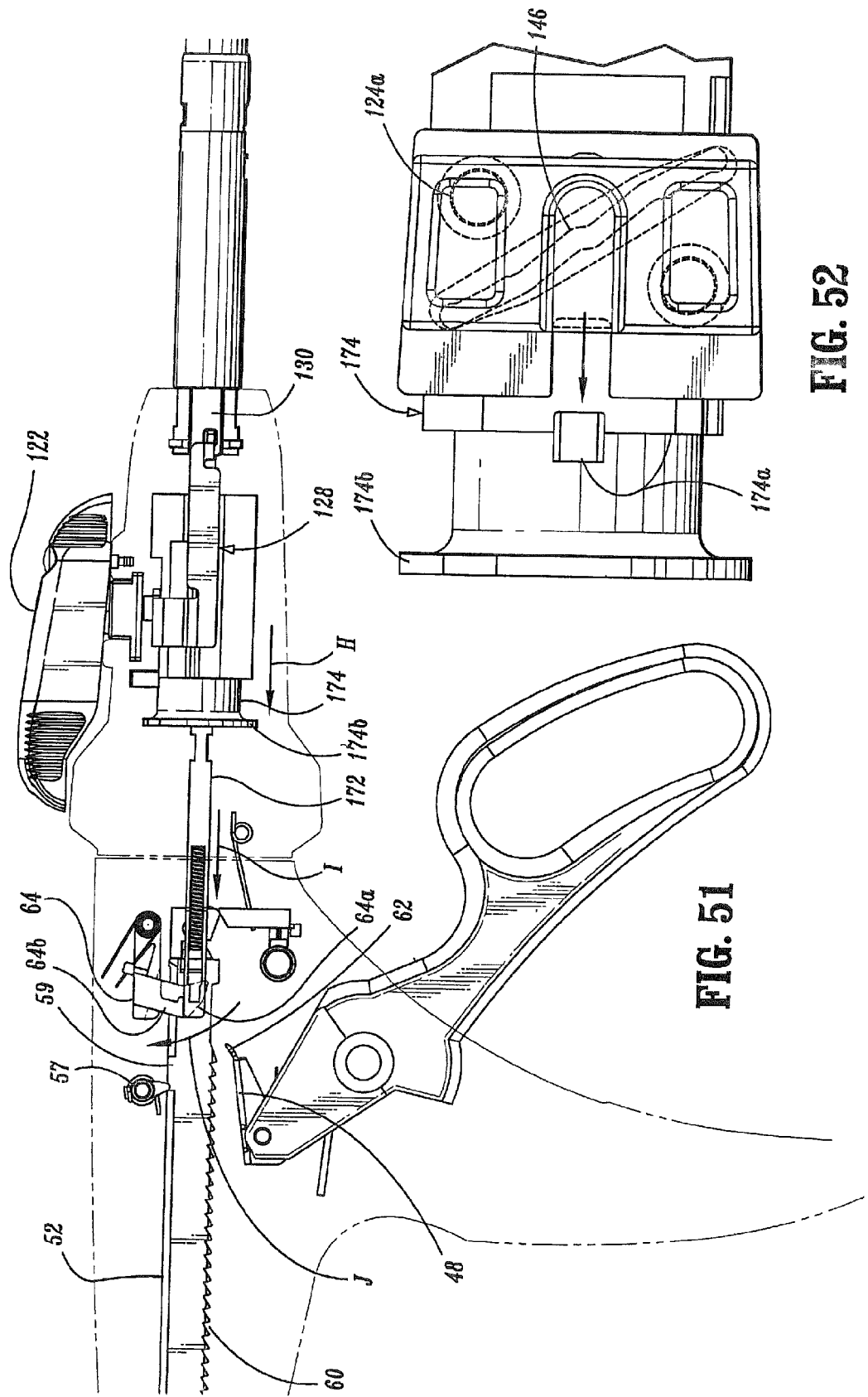

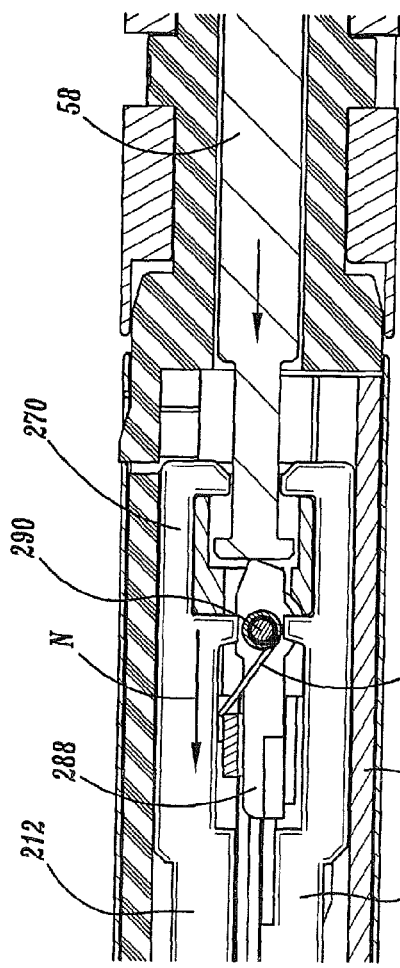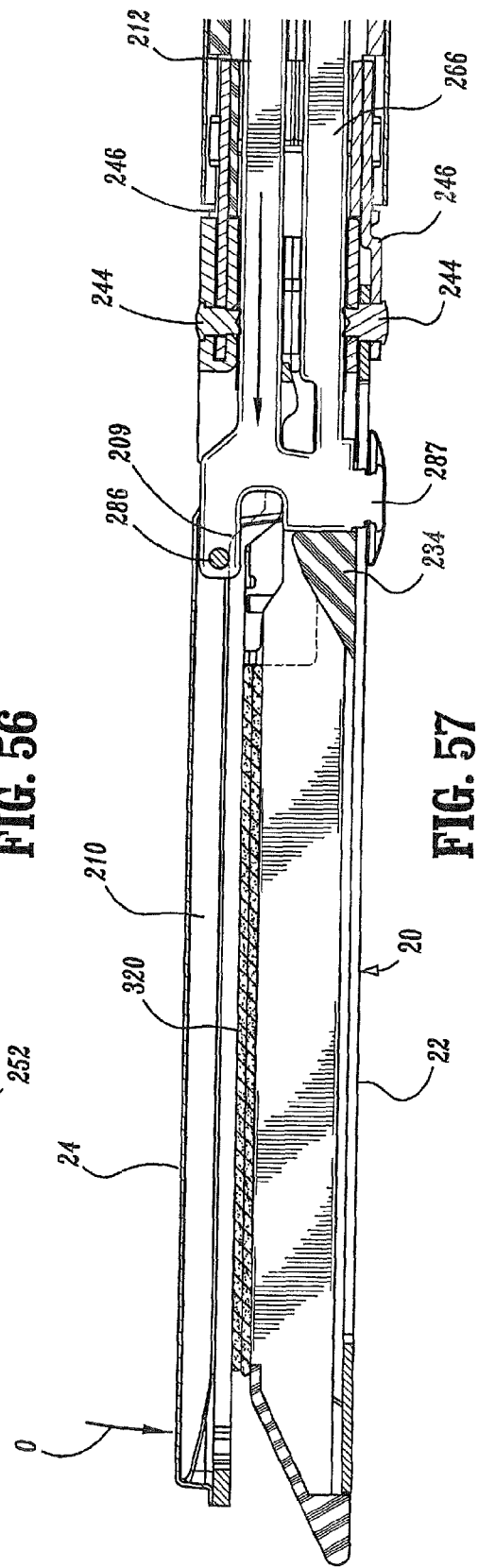

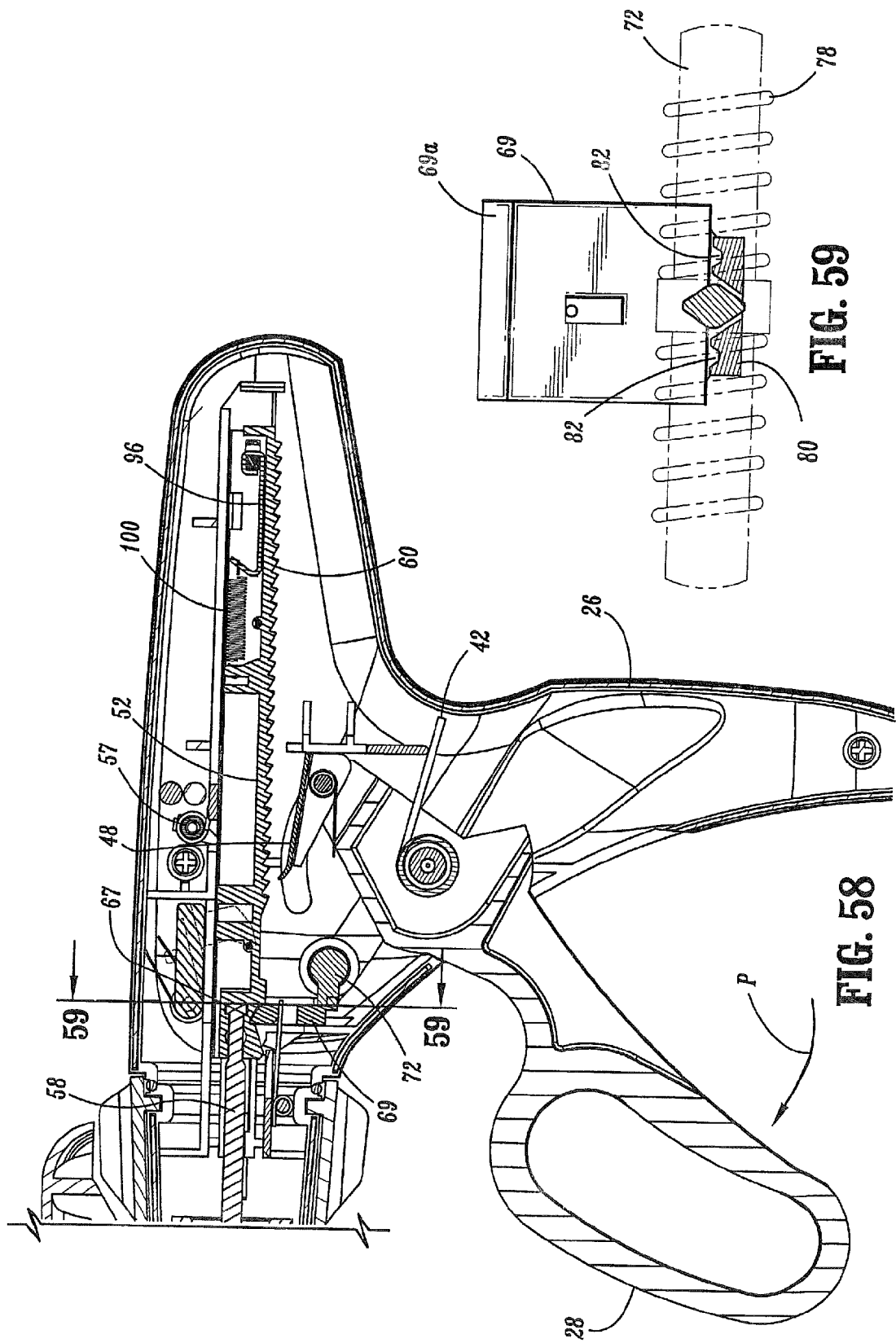

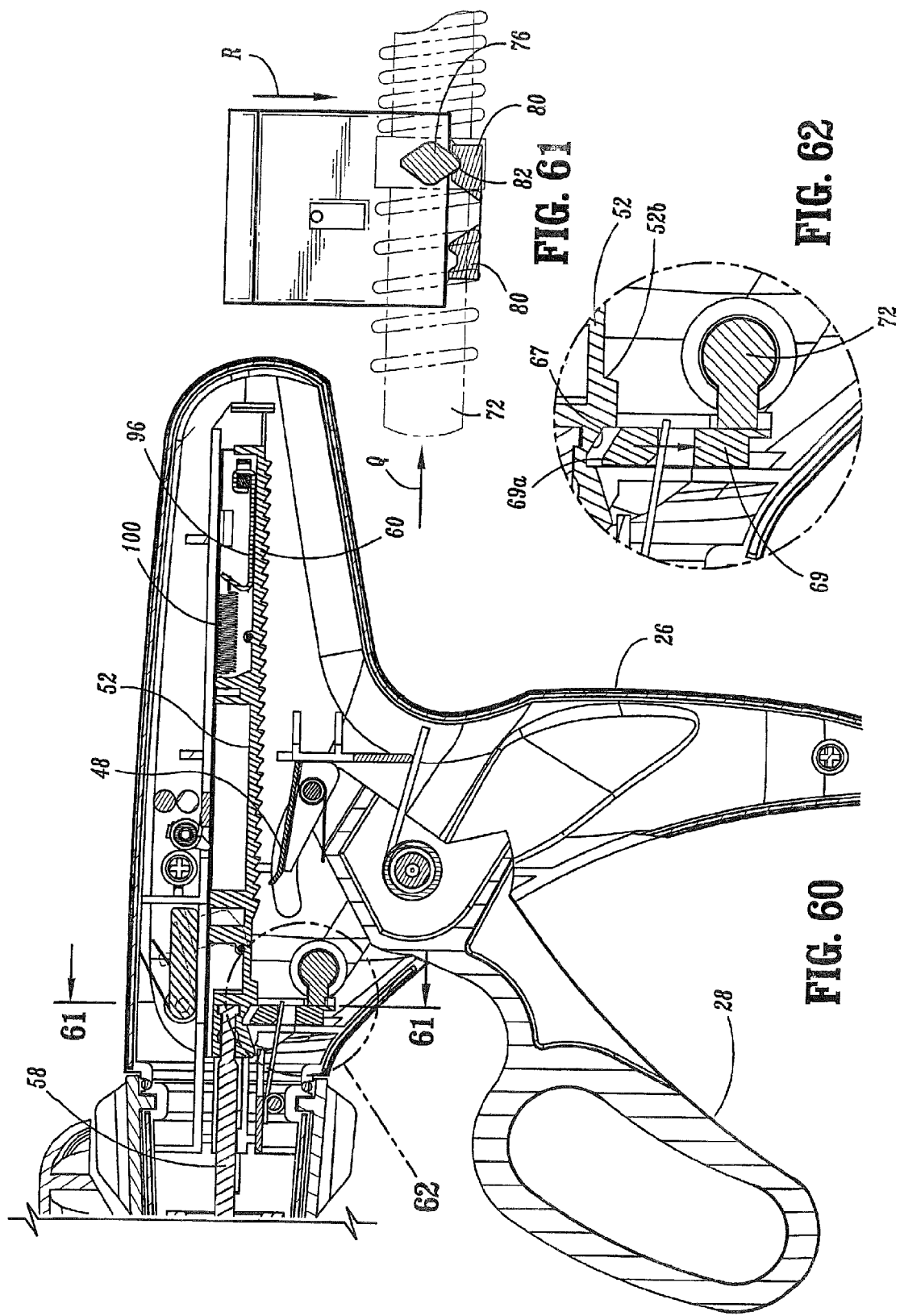

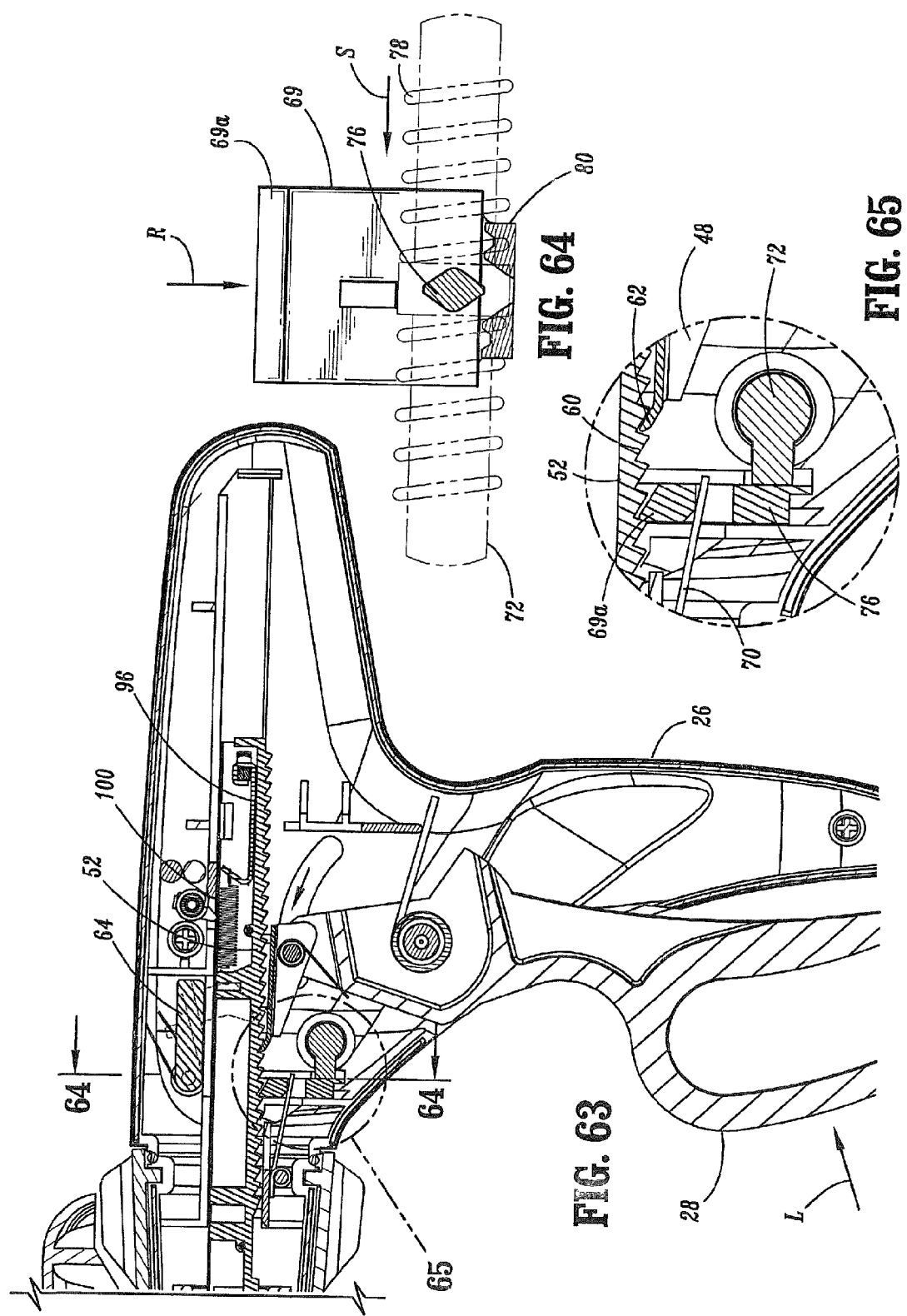

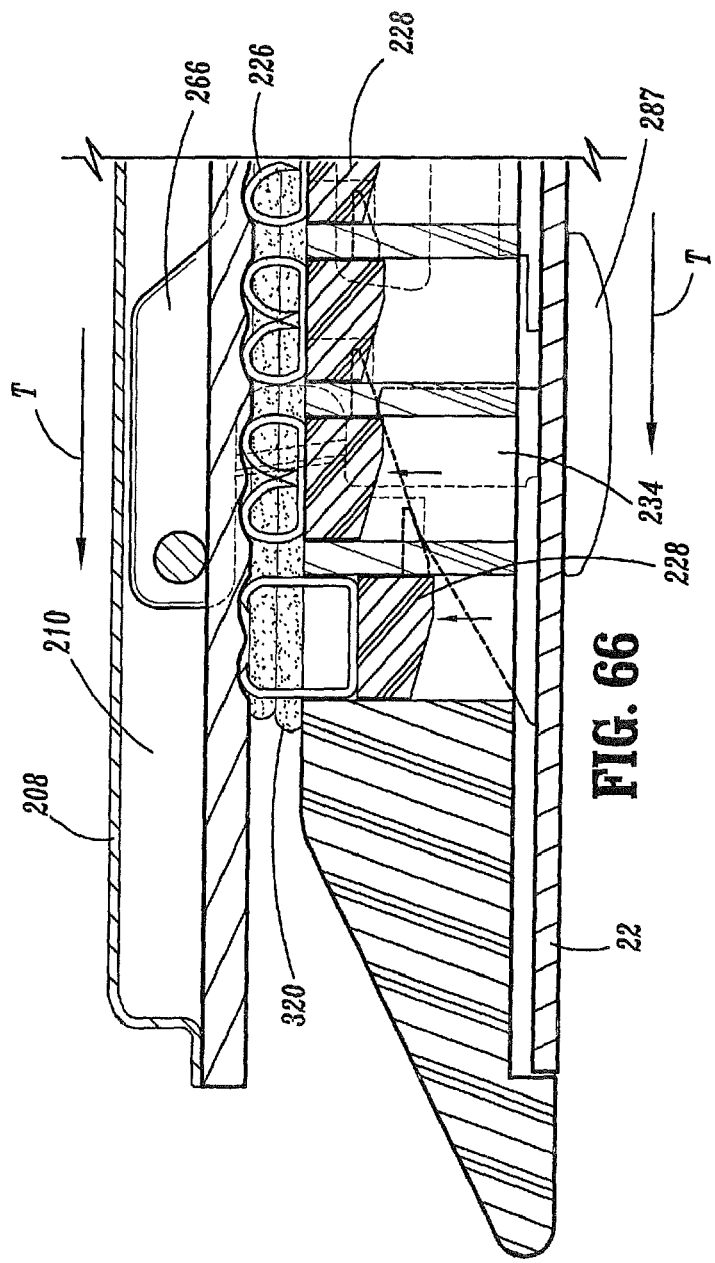
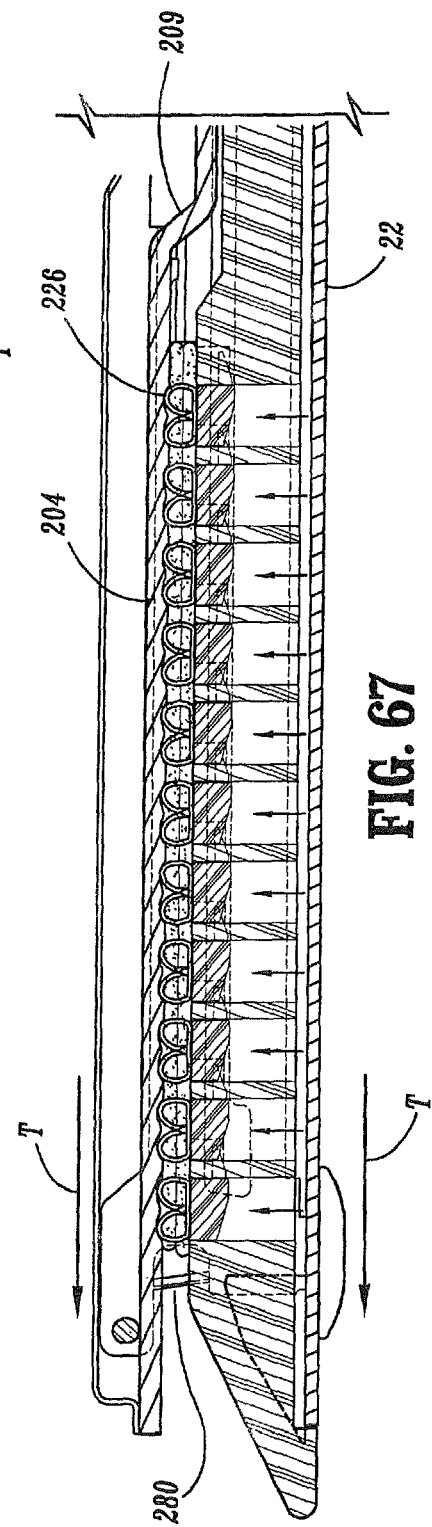

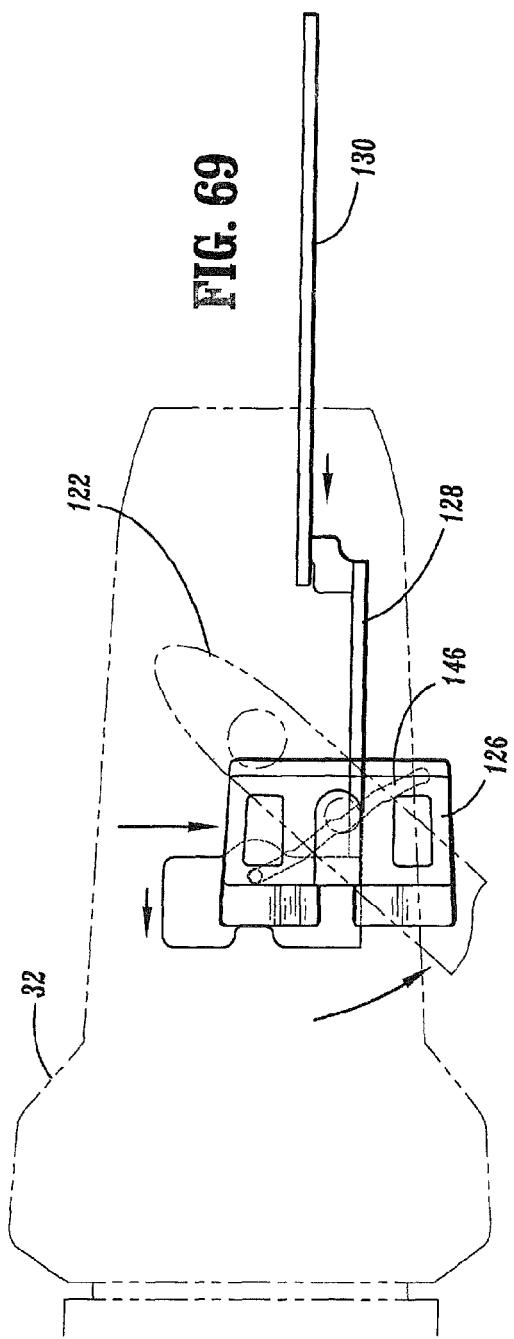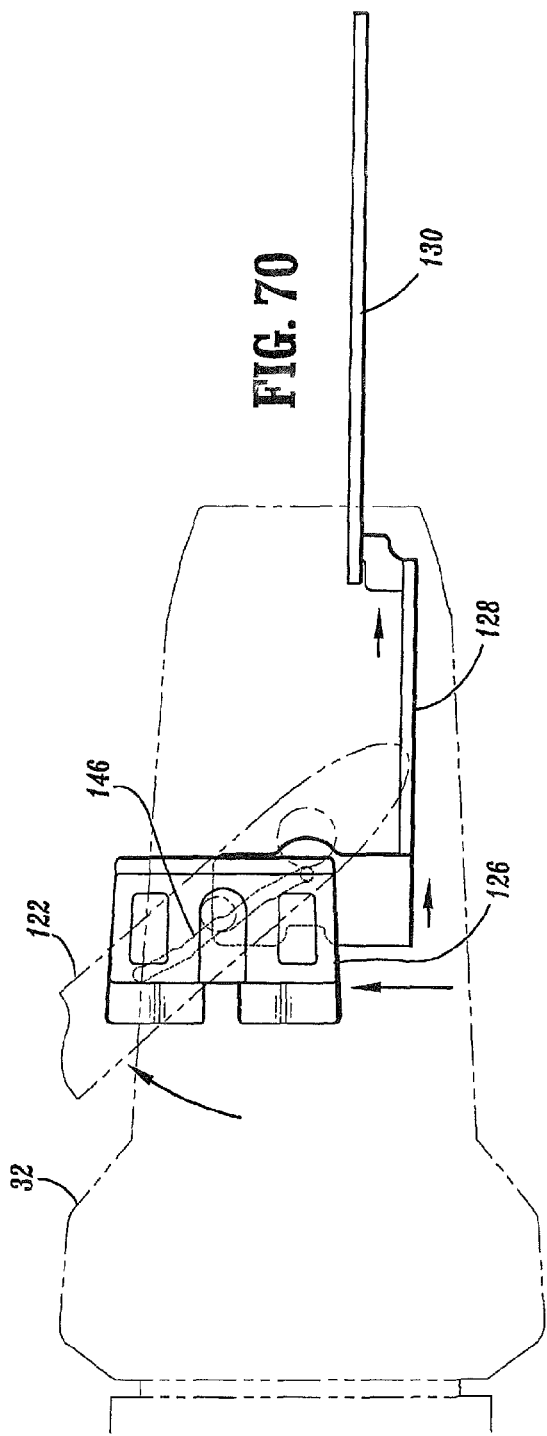

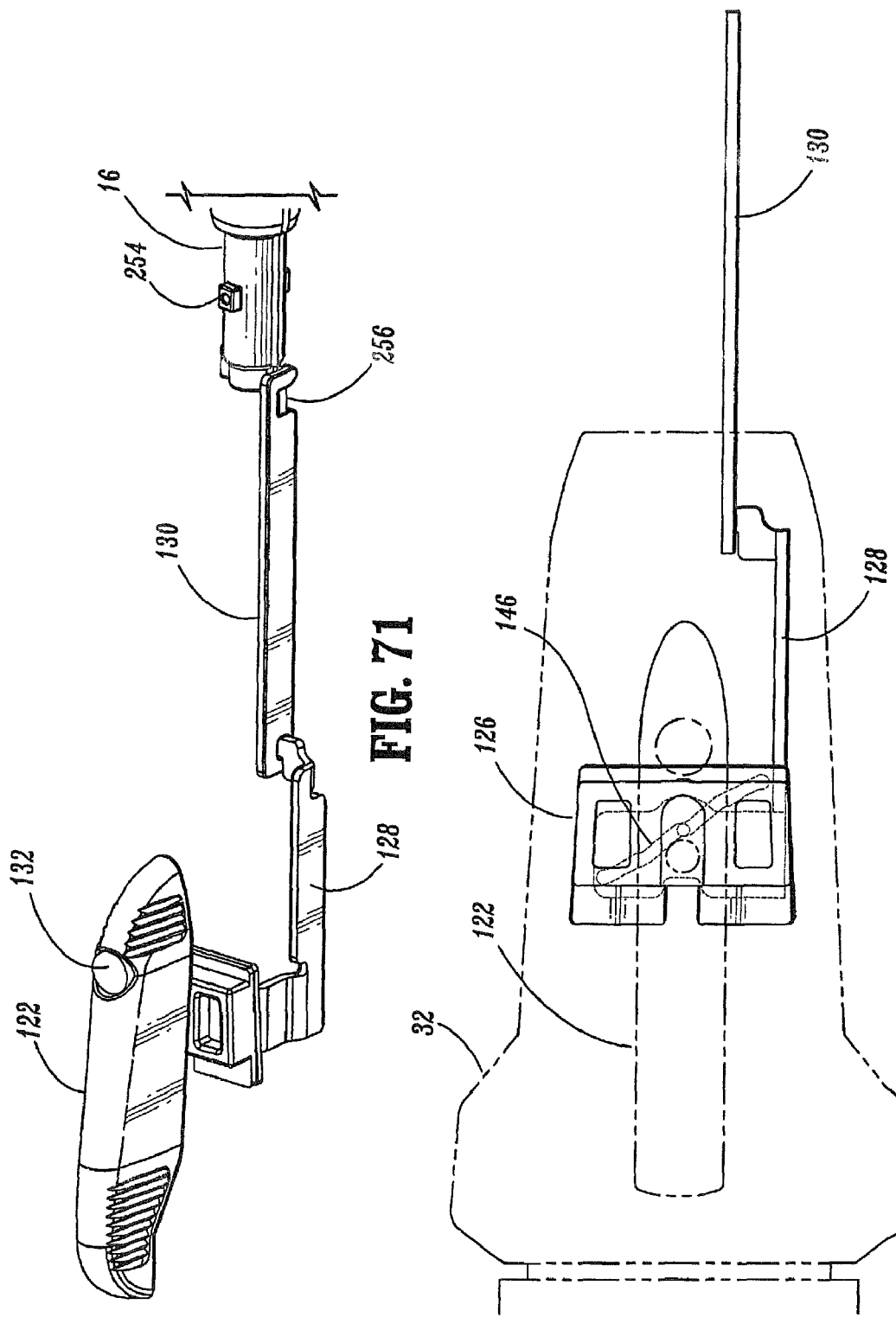

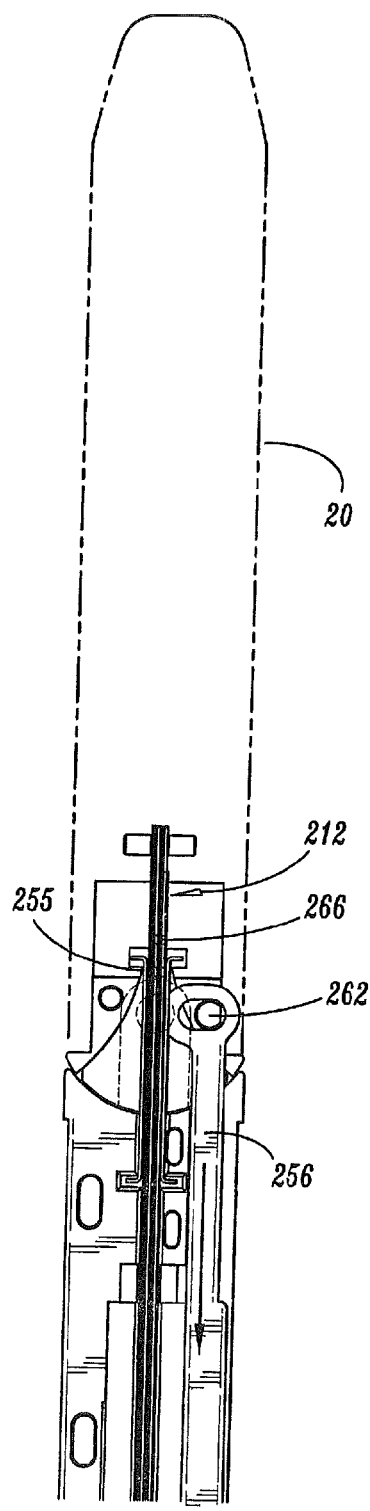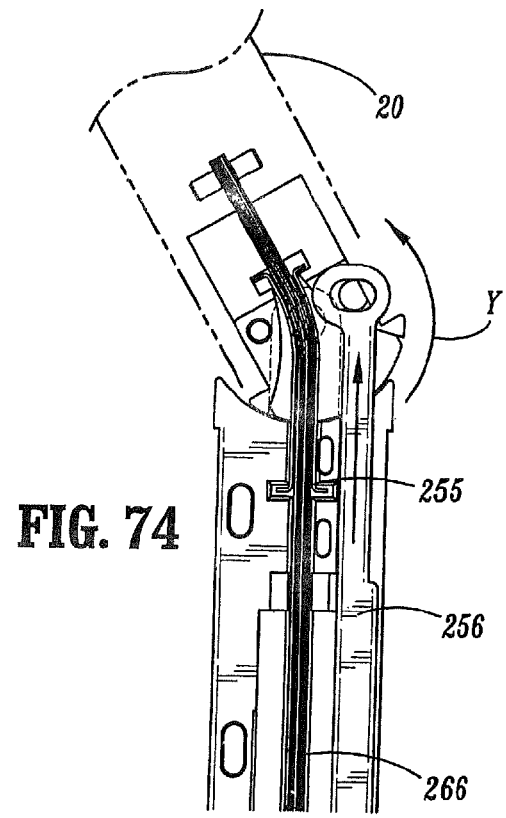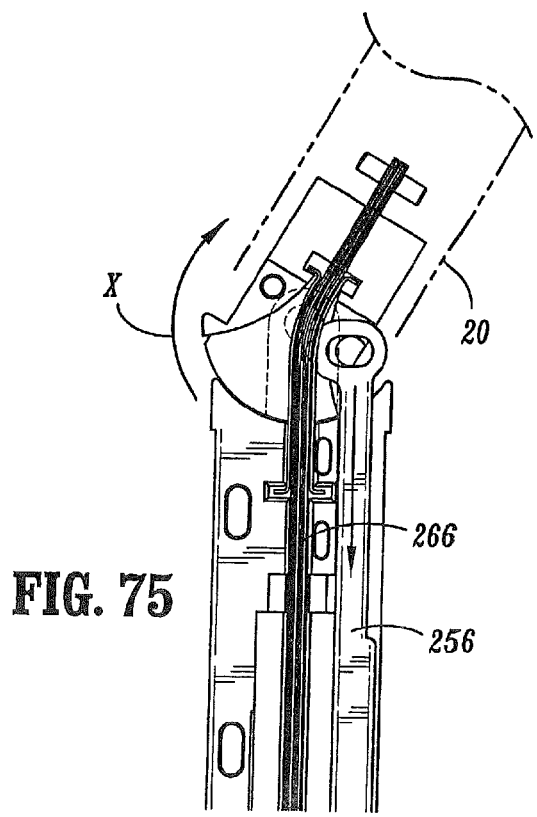
FIG. 73
FIG. 74
FIG. 75

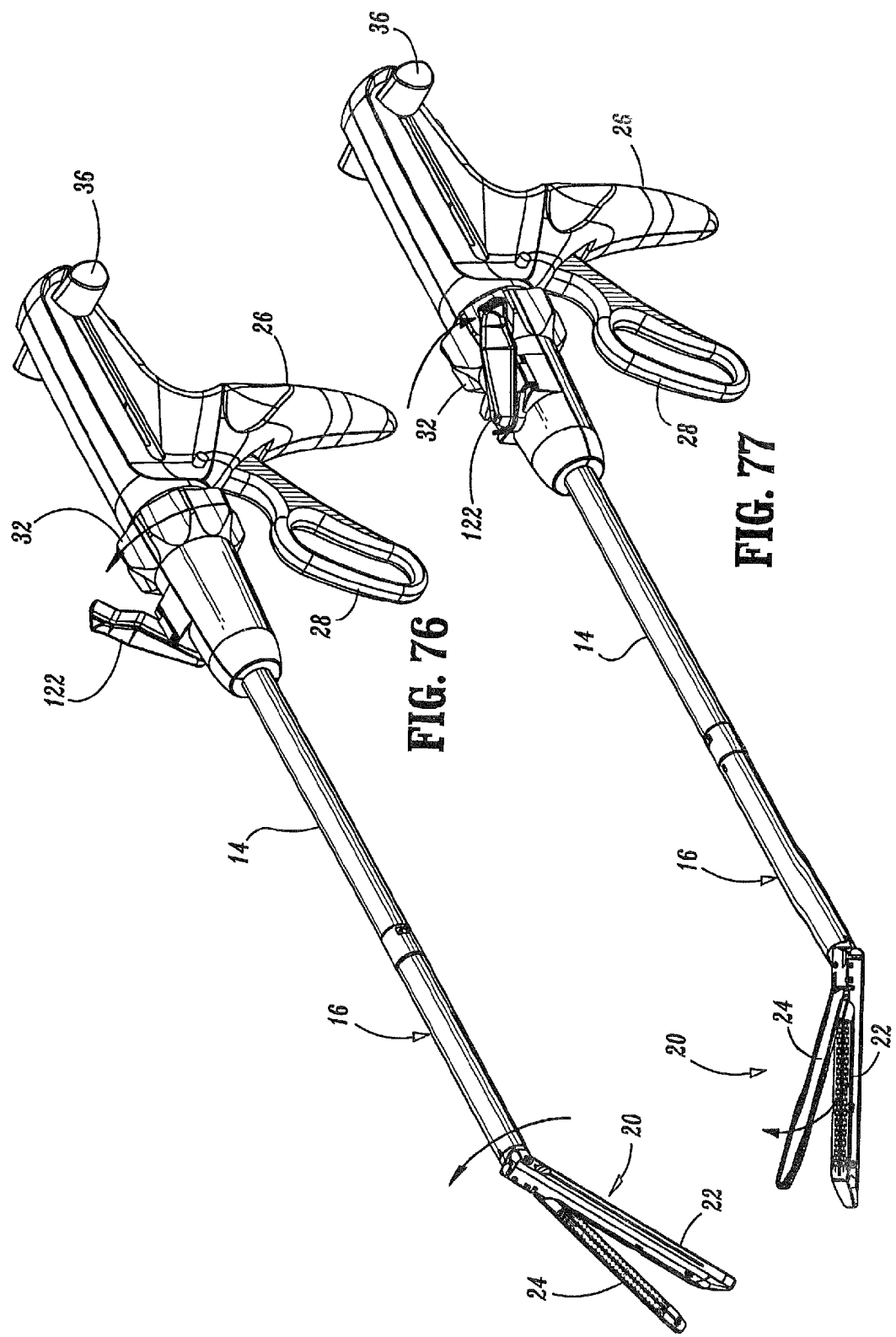

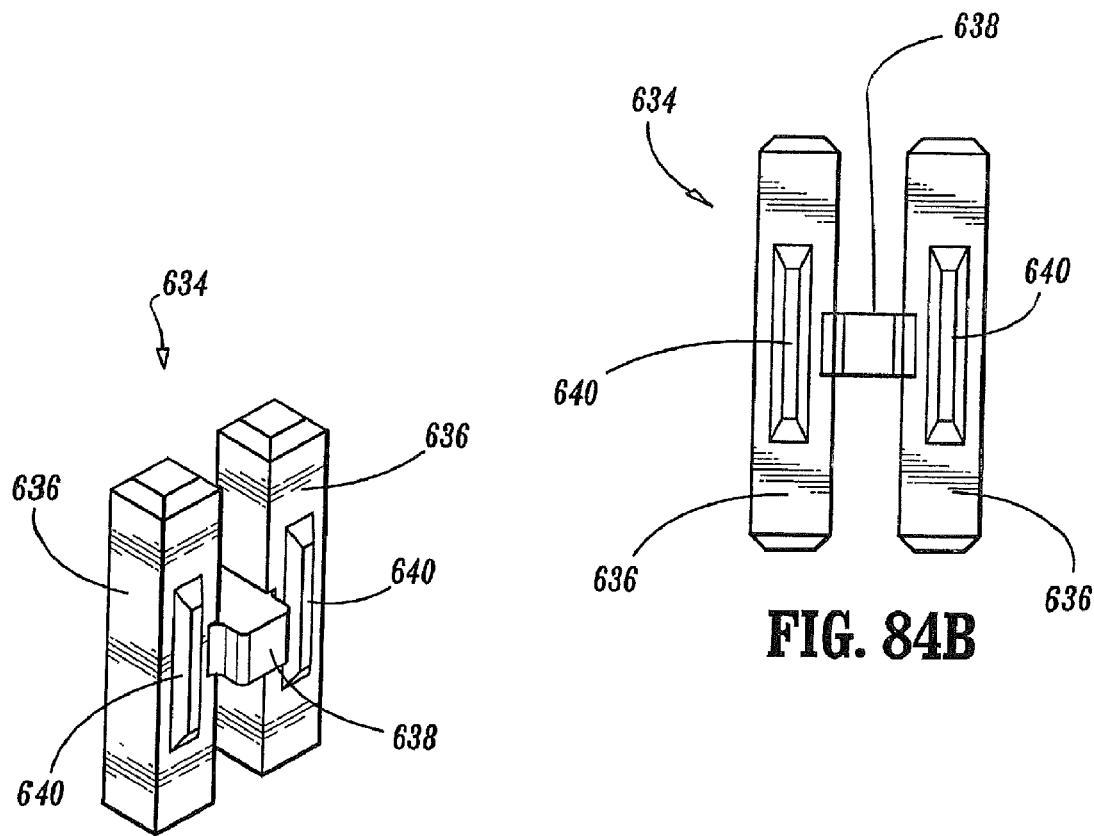
FIG. 84A
FIG. 84B
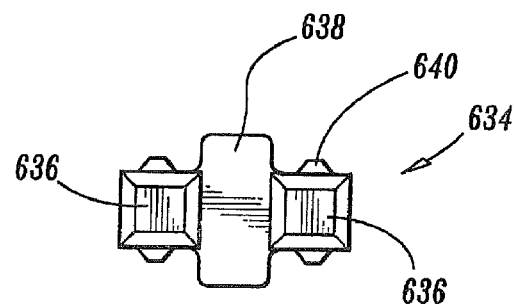
FIG. 84C

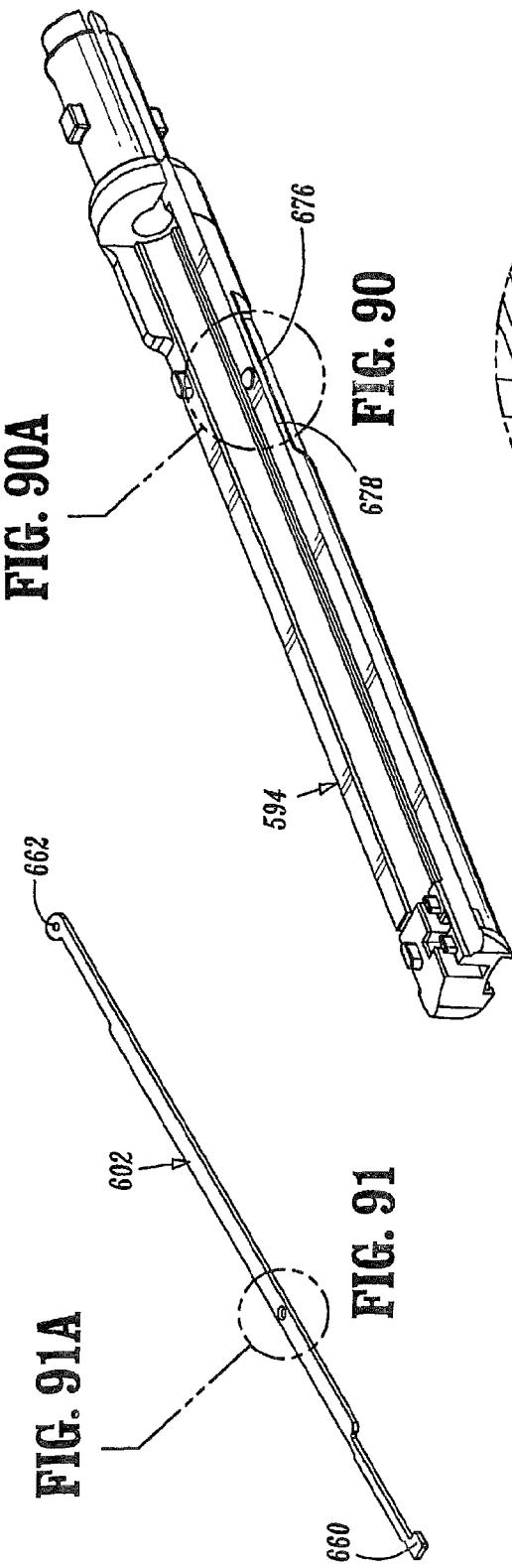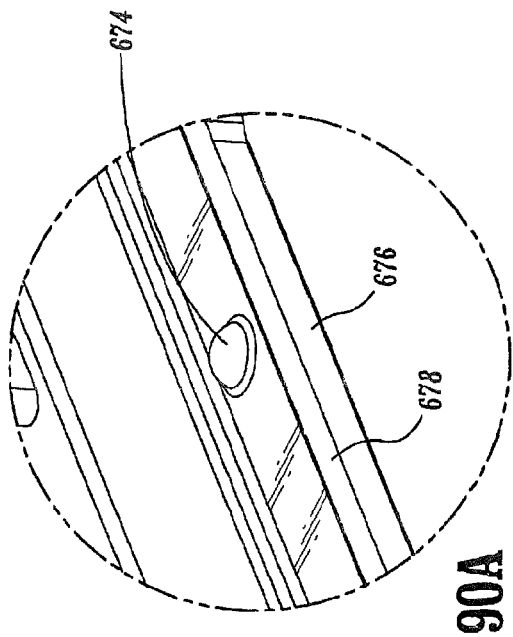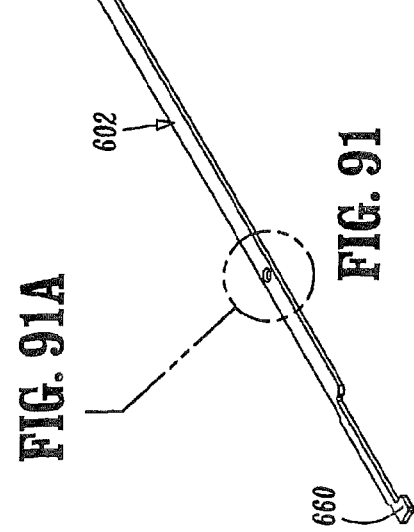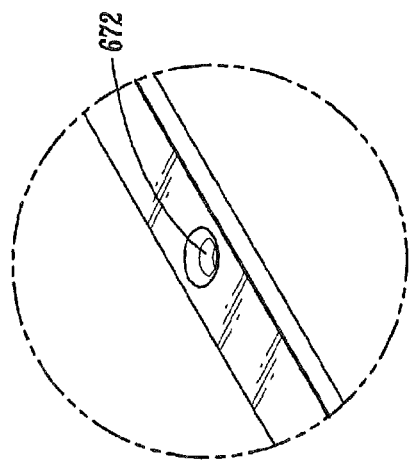

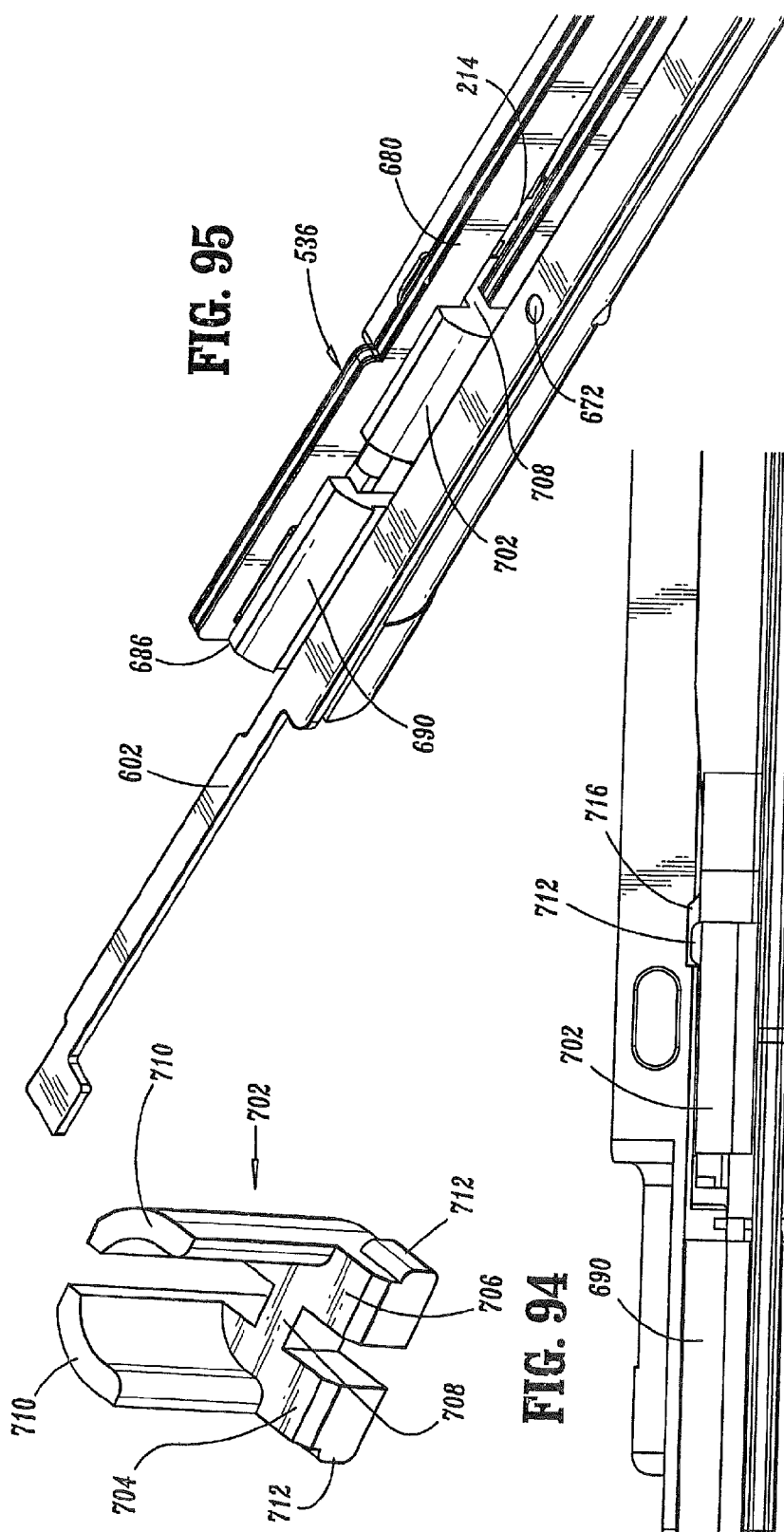
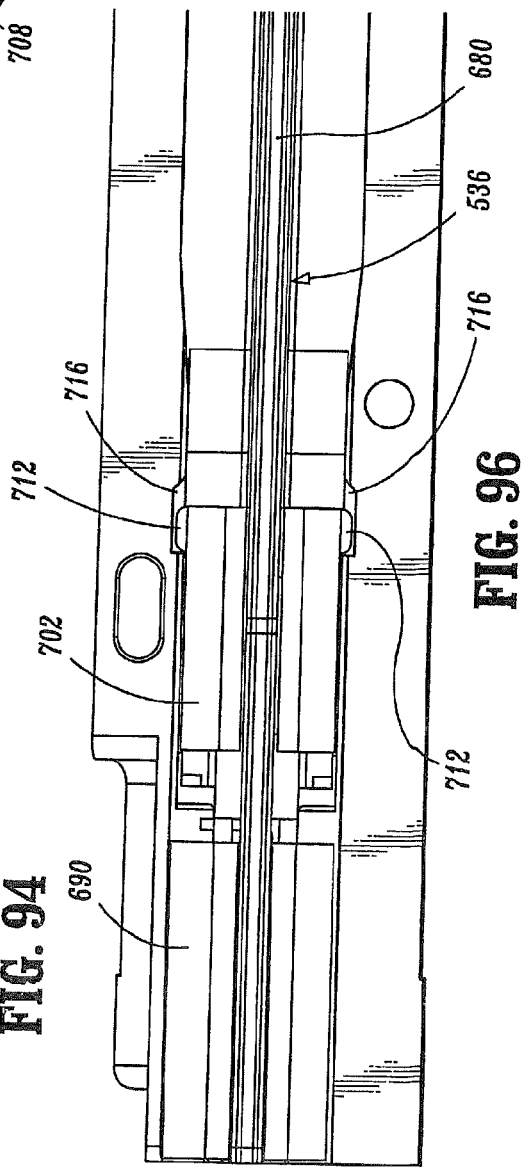

SURGICAL STAPLING DEVICE

CROSS-REFERENCE TO RELATED APPLICATIONS

This application is a continuation of U.S. application Ser. No. 12/732,366 filed Mar. 26, 2010 now U.S. Pat. No. 8,033,440, which is a continuation of U.S. application Ser. No. 12/500,062 filed Jul. 9, 2009 now U.S. Pat. No. 7,891,534, which is a continuation of U.S. application Ser. No. 12/036,659 filed Feb. 25, 2008 now U.S. Pat. No. 7,934,628, which is a continuation of U.S. application Ser. No. 10/490,790 filed Mar. 24, 2004, which is a National Stage Entry of International application No. PCT/US02/32031 filed on Oct. 4, 2002, which claims priority to U.S. Provisional application No. 60/363,502 filed Mar. 11, 2002, now expired, and U.S. Provisional application No. 60/363,487 filed Mar. 11, 2002, now expired, and U.S. Provisional application No. 60/327,527 filed Oct. 5, 2001, now expired, the entire disclosure of each of the above-identified applications are hereby incorporated by reference herein.

BACKGROUND

1. Technical Field

This application relates to a surgical stapling device for applying staples to tissue. More particularly, this application relates to a surgical stapling device having an articulatable tool member for applying linear rows of staples to tissue and concurrently incising the tissue between the linear rows of staples.

2. Background of Related Art

Surgical devices for grasping or clamping tissue between opposed jaw structure of a tool assembly and thereafter fastening the clamped tissue are well known in the art. These devices may include a knife for incising the fastened tissue. The fasteners are typically in the form of surgical staples but two part fasteners formed of a material suitable for surgical use are also well known.

Typically, the tool member includes a staple cartridge which houses a plurality of staples arranged in at least two laterally spaced rows and an anvil which includes a plurality of staple forming pockets for receiving and forming staple legs of the staples as the staples are driven from the cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples.

In laparoscopic and/or endoscopic surgical procedures, the surgical procedure is performed through a small incision or through a narrow cannula inserted through a small entrance wound in a patient. In conventional or open procedures, surgeons directly access an operative site. Because of reduced patient trauma, shortened patient recovery periods and substantial reduction in overall cost, laparoscopic procedures are preferred over open procedures. In order to address the specific needs of endoscopic and/or laparoscopic surgical procedures, endoscopic surgical stapling devices have been developed which provide a surgeon with easier access to the operative site. Typically, these stapling devices include an articulatable tool member which is supported adjacent to the distal end of the stapling device. The tool member can be selectively manipulated to allow a surgeon to manipulate a tool assembly in a confined space. Tyco Healthcare Group, LP has manufactured and marketed articulatable endoscopic stapling instruments such as the MULTIFIRE ENDO GIA *30, MULTIFIRE ENDO GIA 60 and ENDO GIA *Universal for several years. These instruments have provided significant clinical benefits to the field of endoscopic surgery. Nonetheless, improvements in the area of reducing cost and complexity of manufacture are desirable.

In making improvements or modifications to the current instruments, it would be highly desirable not to sacrifice any of the important benefits of the [MULTIFIRE ENDO GIA * 30 and 60] instruments as compared to other commercially available products. For example, any improvement should advantageously provide a fresh knife blade for each firing of the instrument and permit operation of the instrument with multiple size disposable loading units (DLU's).

SUMMARY

In accordance with the present disclosure, a surgical stapling device for sequentially applying a Plurality of fasteners to body tissue and simultaneously incising tissue is provided. The surgical stapling device is adapted to receive disposable loading. units having linear rows of staples having a length of between about 30 mm and 60 mm. The disposable loading units include an articulatable tool assembly which can be operated by manipulating an articulation lever located adjacent a handle assembly of the surgical stapling device.

In addition to the handle assembly, the surgical stapling device includes an elongated body defining the longitudinal axis of the device. The elongated body is operably connected to the handle assembly, for example, by a rotatable collar or knob which is rotatable to effect rotation of the elongated body about the longitudinal axis of the device. The handle assembly includes a movable handle and a stationary handle. The movable handle is movable through an actuation stroke to approximate a cartridge assembly and an anvil assembly, clamp tissue and eject staples from the cartridge assembly of the disposable loading unit.

The disposable loading unit includes a proximal body portion, a mounting assembly and a tool assembly. The mounting assembly is secured to the proximal end of the tool assembly and pivotally mounted about a pivot axis to the distal end of the proximal body portion. A support member or blow-out plate assembly is positioned on opposite sides of the pivot avis and extends between the proximal body portion and the mounting assembly. An axial drive assembly is slidably positioned between the support members and is translatable through the cartridge assembly to eject staples from the cartridge assembly. The support members prevent outward buckling of the is axial drive assembly during actuation especially when the tool assembly is articulated.

An articulation link is provided in the proximal body portion of the disposable loading unit. A first end of the articulation link is operably connected to an articulation assembly of the surgical stapling device. A second end of the articulation link is connected to the mounting assembly at a point offset from the pivot axis. The articulation link is movable to pivot the mounting assembly about the pivot axis to articulate the tool assembly. Preferably, a protrusion is provided in the proximal body portion of the disposable loading unit at a position to frictionally engage the articulation link. Engagement between the protrusion and articulation link retains the articulation link at an axially fixed position within the proximal body portion to maintain the tool assembly in a desired orientation until a predetermined axial force is applied to the articulation link. A recess or recesses may be provided on the articulation link at a position to receive the protrusion to selectively retain the tool assembly at a multiplicity of articulated positions. Alternately, recesses may be provided in the proximal body portion of the disposable loading unit and the protrusion may be provided on the articulation link.

The disposable loading unit preferably includes a locking member which is operably connected to the axial drive assembly. The locking member includes one or more extensions or protrusions which are configured to be received within recesses formed in the proximal body portion of the disposable loading unit. When the drive assembly is actuated to approximate the tool assembly, the protrusions are forced from the recesses to provide an audible and/or tactile indication that the device has been actuated. The locking member also prevents actuation or movement of the drive assembly during shipping.

BRIEF DESCRIPTION OF THE DRAWINGS

Various preferred embodiments of the presently disclosed surgical stapling device are described herein with reference to the drawings:

FIG. 1 is a perspective view of one preferred embodiment of the presently disclosed surgical stapling device;

FIG. 2 is a perspective view of another preferred embodiment of the presently disclosed surgical stapling device;

FIG. 3 is a side view of the surgical stapling device shown in FIG. 2;

FIG. 4 is a top view of the surgical stapling device shown in FIG. 2;

FIG. 15 is an exploded top perspective view of the articulation lever, cam cover and cam member assembly, and drive member of the surgical stapling device shown in FIG. 1;

FIG. 16 is an exploded top perspective view of the elongated body of the surgical stapling device shown in FIG. 2 illustrating the lock button and the plate and spring assembly;

FIG. 17 is a side perspective view of the elongated body of the surgical stapling device shown in FIG. 2 with the outer tube of the elongated body removed;

FIG. 26 is an enlarged perspective view of the actuation sled, the pushers and the fasteners of the surgical stapling device shown in FIG. 2;

FIG. 27 is a bottom perspective view of the staple cartridge shown in FIG. 22;

FIG. 28g is a vertical cross sectional view, with portions broken away, of the proximal end of the tool assembly and the distal end of the proximal body portion of the disposable loading unit of the surgical stapling device shown in FIG. 2;

FIG. 29 is an enlarged perspective view, with portions broken away, of the mounting assembly of the disposable loading unit shown in FIG. 21 mounted to a distal end portion of the proximal body portion;

FIG. 30 is a perspective view of the distal end of the proximal body portion and the mounting assembly of the disposable loading unit shown in FIG. 21 with the upper housing half section removed;

FIG. 31 is a perspective view of the proximal body portion and the mounting assembly of the disposable loading unit shown in FIG. 21 with the upper housing half section and outer tube removed;

FIG. 33 is an enlarged perspective view of the axial drive assembly shown in FIG. 32;

FIG. 34 is an enlarged perspective view of the distal end of the axial drive assembly shown in FIG. 33;

FIG. 35 is an enlarged perspective view of the distal end of the axial drive assembly shown in FIG. 32;

FIG. 38 is a top horizontal cross sectional view of the proximal end of the disposable loading unit shown in FIG. 21;

FIG. 39 is a side cross sectional view of the distal end of the proximal body portion, the mounting assembly and the proximal end of the tool assembly of the disposable loading unit shown in FIG. 21;

FIG. 40 is a perspective view of the distal end of the elongated body portion of the surgical stapling device shown in FIG. 2;

FIG. 41 is a perspective view of the proximal end of the disposable loading unit shown in FIG. 21;

FIG. 42 is a side view of the proximal end of the disposable loading unit shown in FIG. 21 and the distal end of the elongated body portion of the surgical stapling device shown in FIG. 2 prior to attachment of the disposable loading unit to the elongated body portion;

FIG. 43 is a side view of the proximal end of the disposable loading unit and the distal end of the elongated body portion during attachment of the disposable loading unit to the elongated body portion of the surgical stapling device shown in FIG. 2;

FIG. 44 is a side cross sectional view of the distal end of the elongated body portion of the surgical stapling device shown in FIG. 2 and the proximal end of the disposable loading unit shown in FIG. 21 during attachment of the disposable loading unit to the elongated body portion;

FIG. 45 is a side view of the proximal end of the disposable loading unit and the distal end of the elongated body portion during attachment of the disposable loading unit to the elongated body portion;

FIG. 46 is a perspective partial cut away view, with portions broken away, of the proximal end of the disposable loading unit and the distal end of the elongated body portion during attachment of the disposable loading unit to the elongated body portion;

FIG. 47 is a side cross-sectional view of the surgical stapling device shown in FIG. 2 in the unapproximated position;

FIG. 48 is an enlarged view of the indicated area of detail shown in FIG. 47;

FIG. 49 is an enlarged view of the indicated area of detail shown in FIG. 47;

FIG. 50 is a cross-sectional view taken along section lines 50-50 shown in FIG. 49;

FIG. 51 is a side view of the handle assembly of the surgical stapling device shown in FIG. 2 with the handle housing and the rotatable knob shown in phantom and illustrating the sequence of operation during attachment of a disposable loading unit to the surgical stapling device;

FIG. 52 is a top view, with portions broken away, of the cam cover and cam member assembly and sensor cap illustrating the sequence of operation during attachment of a disposable loading unit to the elongated body of the surgical stapling device;

FIG. 56 is a side cross-sectional view of the proximal end of the proximal body portion of the disposable loading unit of the surgical stapling device shown in FIG. 2 after the device has been approximated;

FIG. 57 is a side cross sectional view of the tool assembly of the disposable loading unit of the surgical stapling device shown in FIG. 2 in the approximated position;

FIG. 58 is a side cross sectional view of the handle assembly of the surgical stapling device shown in FIG, 2 in the approximated position with the handle in the non-compressed position;

FIG. 59 is a cross-sectional view taken along a portion of section lines 59-59 of FIG. 58;

FIG. 60 is a side cross sectional view of the handle assembly of the surgical stapling device shown in FIG. 2 with the plunger disengaged from the vertical pawl;

FIG. 61 is a cross-sectional view taken along a portion of section lines 61-61 of FIG. 60;

FIG. 62 is an enlarged view of the indicated area of detail shown in FIG. 60;

FIG. 63 is a side cross-sectional view of the handle assembly of the surgical stapling device shown in FIG. 2 during the firing stroke of the surgical stapling device;

FIG. 64 is a cross sectional view taken along a portion of section lines 64-64 of FIG. 63;

FIG. 65 is an enlarged view of the indicated area of detail shown in FIG. 63;

FIG. 66 is a cross-sectional view of the distal end of the tool assembly during the firing stroke of surgical stapling device;

FIG. 67 is a side cross-sectional view of the tool assembly of the surgical stapling device shown in FIG, 2 after completion of the firing stroke;

FIG. 69 is a top view of the rotatable knob and articulation mechanism of the surgical stapling device shown in FIG. 2 with the tool assembly articulated in a first direction with the rotatable knob and the articulation lever shown in phantom;

FIG. 70 is a top view of the rotatable knob and articulation mechanisms of the surgical stapling device shown in FIG. 2 with the tool assembly articulated in a second direction;

FIG. 71 is a side perspective view of the articulation mechanism of the surgical stapling device shown in FIG. 2;

FIG. 72 is a top view of the rotatable knob and articulation mechanism of surgical stapling device shown in FIG. 2 with the rotatable knob and articulation lever shown in phantom;

FIG. 73 is a top view of the distal end of the disposable loading unit prior to articulation of the tool assembly;

FIG. 74 is a top view of the distal end of the disposable loading unit during articulation of the tool assembly in a first direction;

FIG. 75 is a top view of the distal end of the disposable loading unit shown in FIG. 21 during articulation of the tool assembly in a second direction;

FIG. 76 is a side perspective view of the surgical stapling device shown in FIG. 2 with the tool assembly articulated in a first direction;

FIG. 77 is a side perspective view of the surgical stapling device shown in FIG. 2 with the tool assembly articulated in a second direction;

FIG. 84A is a top perspective view of the locking member of the blow out plate assembly of the disposable loading unit shown in FIG. 80;

FIG. 84B is a front elevational view of the locking member shown in FIG. 84A;

FIG. 84C is a top view of the locking member shown in FIG. 84A;

FIG. 90 is a perspective view of the upper housing half of the proximal body portion of the disposable loading unit shown in. FIG. 80;

FIG. 90A is an enlarged view of the indicated area of detail shown in FIG, 90;

FIG. 91 is a perspective view of the articulation link of the disposable loading unit shown in FIG. 80;

FIG. 91A is an enlarged view of the indicated area of detail shown in FIG. 91;

FIG. 94 is a perspective view of the locking member of the disposable loading unit shown in FIG. SO;

FIG. 95 is a perspective view of the proximal end of the proximal body portion of the disposable loading unit shown in FIG. 80; and FIG. 96 is a top view of the proximal end of the proximal body portion of the disposable loading unit shown in FIG. 80.

DETAILED DESCRIPTION OF PREFERRED EMBODIMENTS

Figure 5:
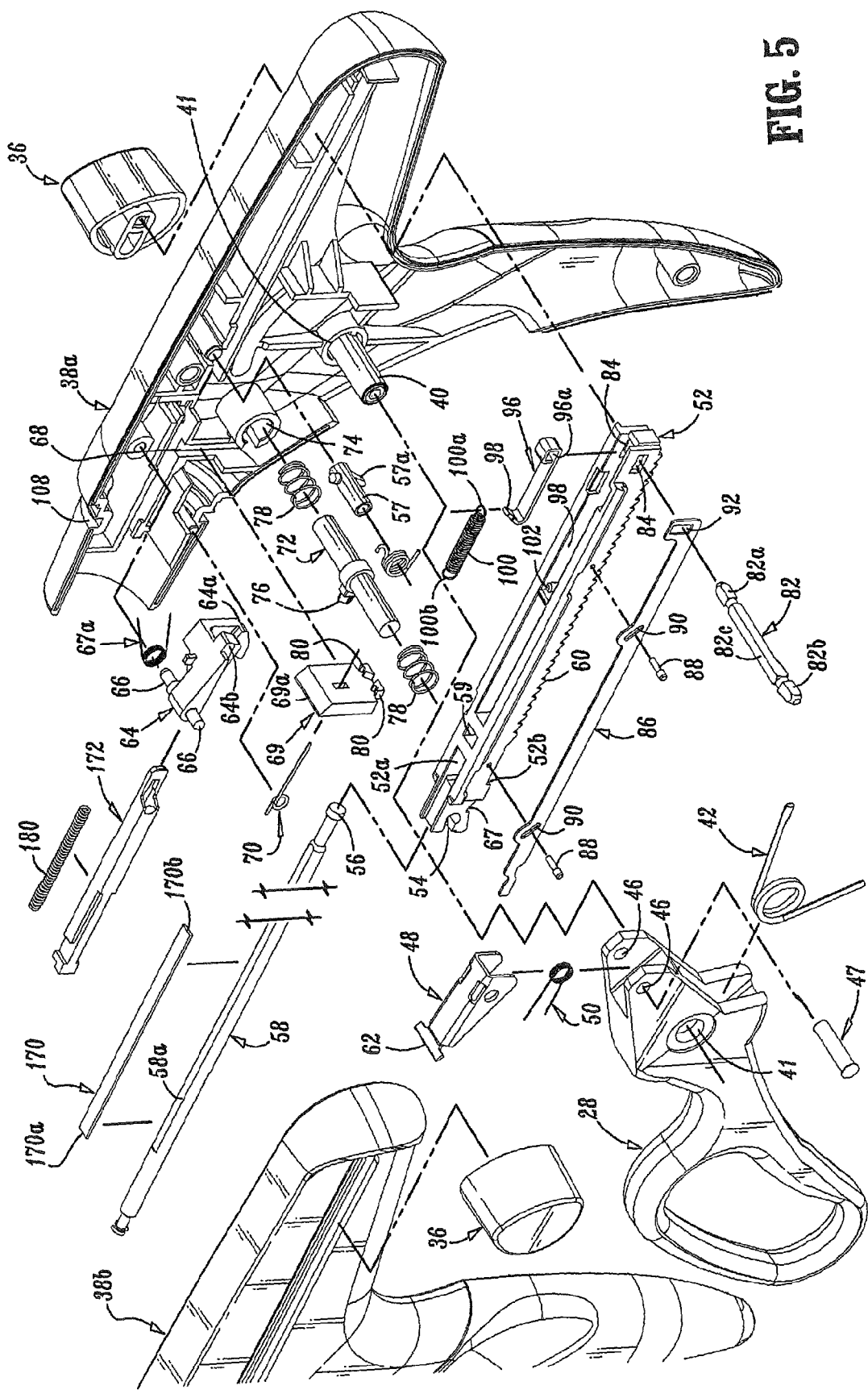
FIG. 5 is a perspective view with parts separated of the handle assembly of the surgical stapling device shown in FIG. 2.
Figure 6:
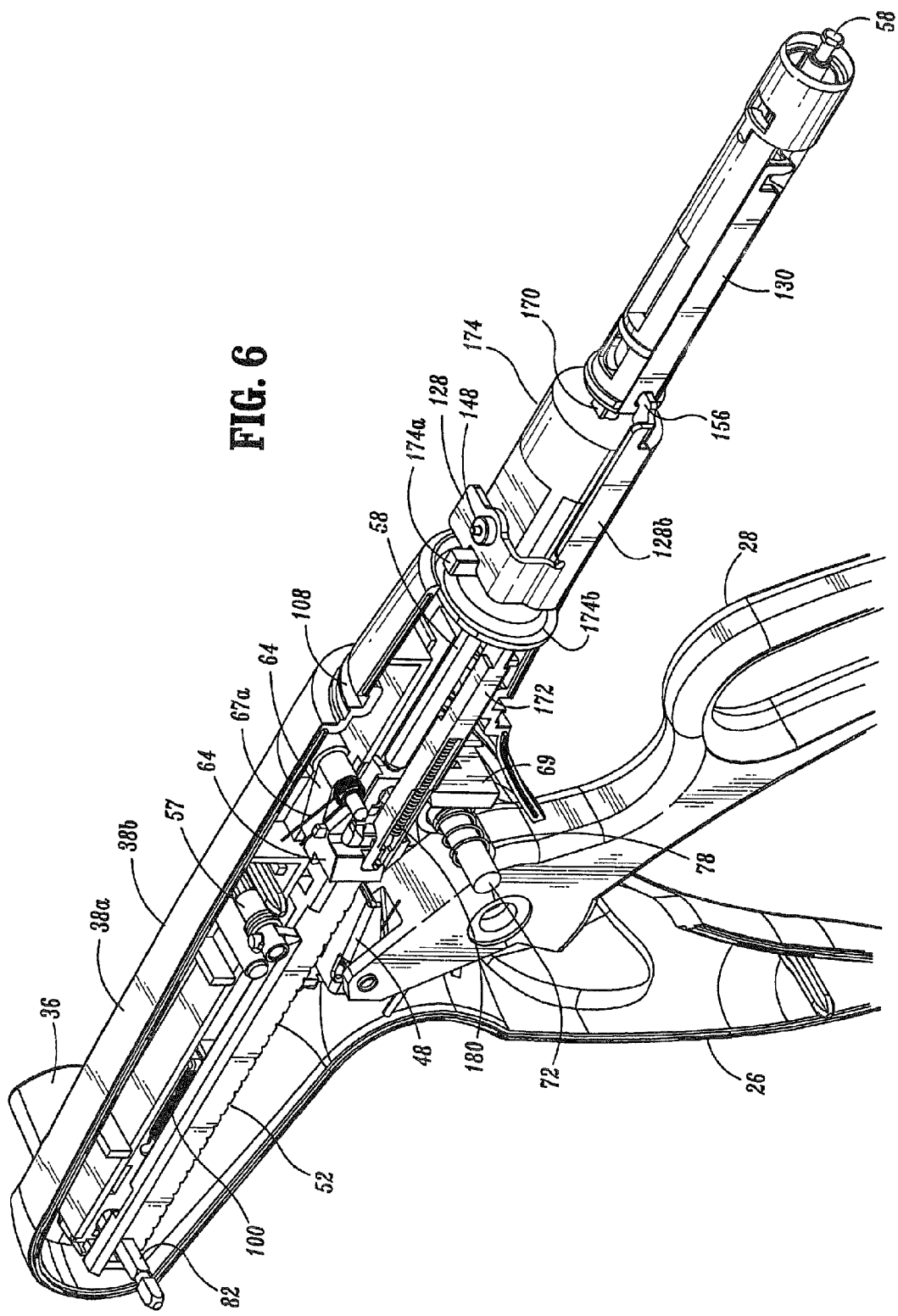
FIG. 6 is a front side perspective view of the surgical stapling device shown in FIG. 2 with a housing half section, the rotatable knob, and the outer tube of the elongated body removed.
Figure 7:
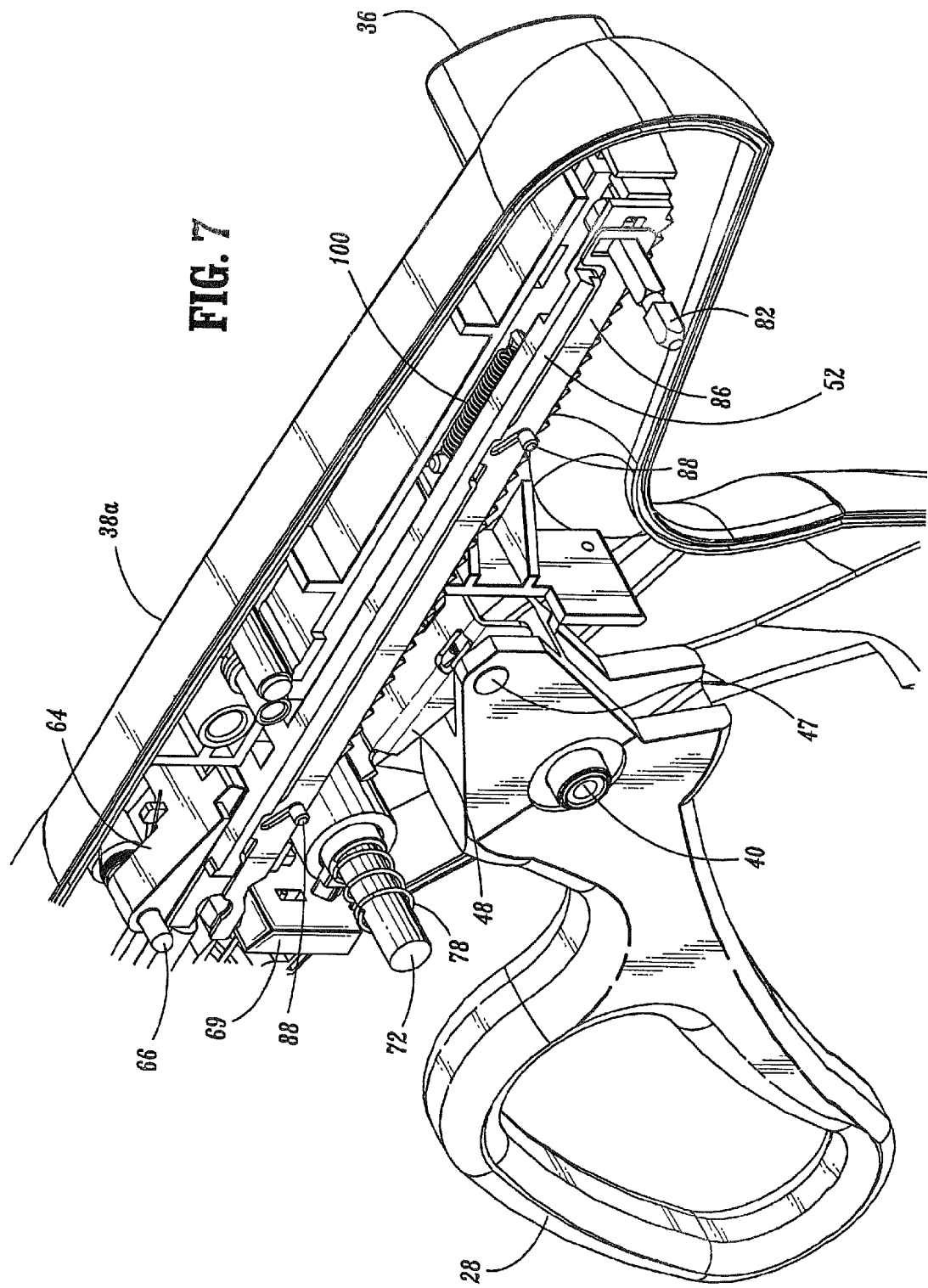
FIG. 7 is an enlarged side perspective view with portions broken away of the handle assembly of the surgical stapling device shown hi FIG. 2 with the housing half section removed.

Preferred embodiments of the presently disclosed surgical stapling device will now be described in detail with reference to the drawings in which like reference numerals designate identical or corresponding elements in each of the several views.

In the description that follows, the term "proximal", as is traditional, will refer to the end of the stapling device which is closest to the operator, while the term distal will refer to the end of the device which is furthest from the operator.

FIGS. 1-4 illustrate one preferred embodiment of the presently disclosed surgical stapling device shown generally as 10. Briefly, surgical stapling device 10 includes a handle assembly 12 and an elongated body 14. As illustrated in FIGS. 1 and 2, the length of elongated body 14 may vary to suit a particular surgical procedure. A disposable loading unit or DLU 16 is releasably secured to a distal end of elongated body 14. DLU 16 includes a proximal body portion 18, which forms an extension of elongated body 14, and a distal tool assembly 20 including a cartridge assembly 22 and an anvil assembly 24. Tool assembly 20 is pivotably connected to body 18 about an axis substantially perpendicular to the longitudinal axis of elongated body 14. Cartridge assembly 22 houses a plurality of staples. Anvil assembly 24 is movable in relation to cartridge assembly 22 between an open position spaced from cartridge assembly 22 and an approximated or clamped position in juxtaposed alignment with cartridge assembly 24. Preferably, the staples are housed in cartridge assembly 22 to apply linear rows of staples having a length measuring from about 30 mm to about 60 mm, although other staple configurations and lengths are envisioned.

Handle assembly 12 includes a stationary handle member 26, a movable handle or trigger 28 and a barrel portion 30. A rotatable member 32 is preferably rotatably mounted to the forward end of barrel portion 30 and secured to elongated body 14 to facilitate rotation of elongated body 14 in relation to handle assembly 12. An articulation lever 122 is supported on a distal portion of barrel portion 30 and is operable, in a manner to be described hereafter, to effect articulation of tool assembly 20 with respect to body portion 18 of DLU 16. A pair of return knobs 36 are movably supported along barrel portion 30 to effect movement of surgical stapling device 10 from an advanced position to a retracted position, as will be described in detail below.

Referring to FIGS. 5-8, handle assembly 12 includes a housing 38, which is preferably formed from plastic molded housing half-sections 38a and 38b. Alternately, other materials may, be used to form the housing including metals, e.g., stainless steel. Housing 38 forms stationary handle 26 and barrel portion 30 of handle assembly 12 (see FIG. 1). Movable handle 28 is rotatably supported between housing half-sections 38a and 38b about a cylindrical member 40 which is received within an opening 41 in movable handle 28. A biasing member 42, which is preferably a torsion spring, urges movable handle 28 away from stationary handle 26 to a non-compressed position. Movable handle 28 includes a pair of throughbores 46 dimensioned to receive a pivot member 47. A pawl 48 is rotatably supported on pivot member 47 and is biased by a spring 50 towards actuation shaft 52.

Actuation shaft 52 is slidably supported between retracted and advanced positions within barrel portion 30 of housing 38 and includes a distal end defining a recess 54 configured to rotatably receive the proximal end 56 of firing rod 58. A spring biased retract arm 57 is rotatably mounted between housing half-sections 38a and 38b and includes an extension 57a. Extension 57a is positioned within a slot 59 (FIG. 5) formed in actuation shaft 52 to urge actuation shaft 52 to a fully retracted position. Actuation shaft 52 includes a toothed rack 60. Pawl 48 has an engagement finger 62 which is biased by spring 50 towards toothed rack 60 of actuation shaft 52. When movable handle 28 is actuated, i.e., is compressed towards stationary handle 26 against the bias of spring 42, engagement finger 62 of pawl 48 engages toothed rack 60 of actuation shaft 52 to advance actuation shaft 52 and firing rod 58 distally. Firing rod 58 preferably includes a distal end which is formed from stainless steel and the remaining portion (approximately 90%) formed from aluminum. The two parts may be press fit together. Alternately, firing rod 58 may be formed from a single material or any material or materials having the requisite strength requirements.

Figure 13:
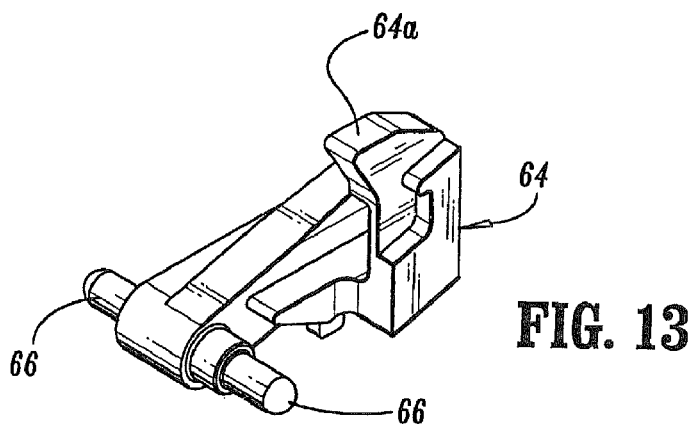
FIG. 13 is a side perspective view of the rack lock of the surgical stapling device shown in FIG. 1.
Figure 14:
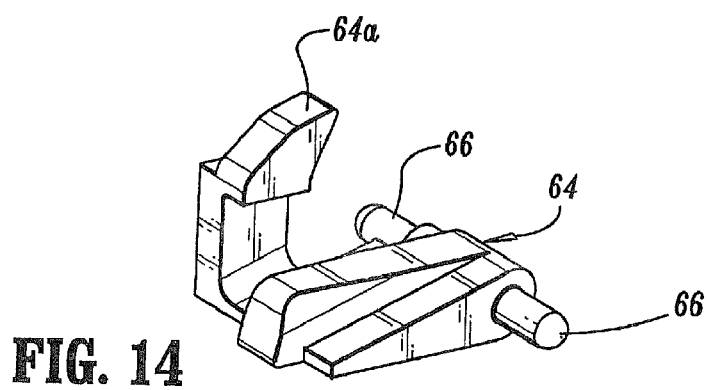
FIG. 14 is a bottom perspective view of the rack lock shown in FIG. 13.
Figure 18:
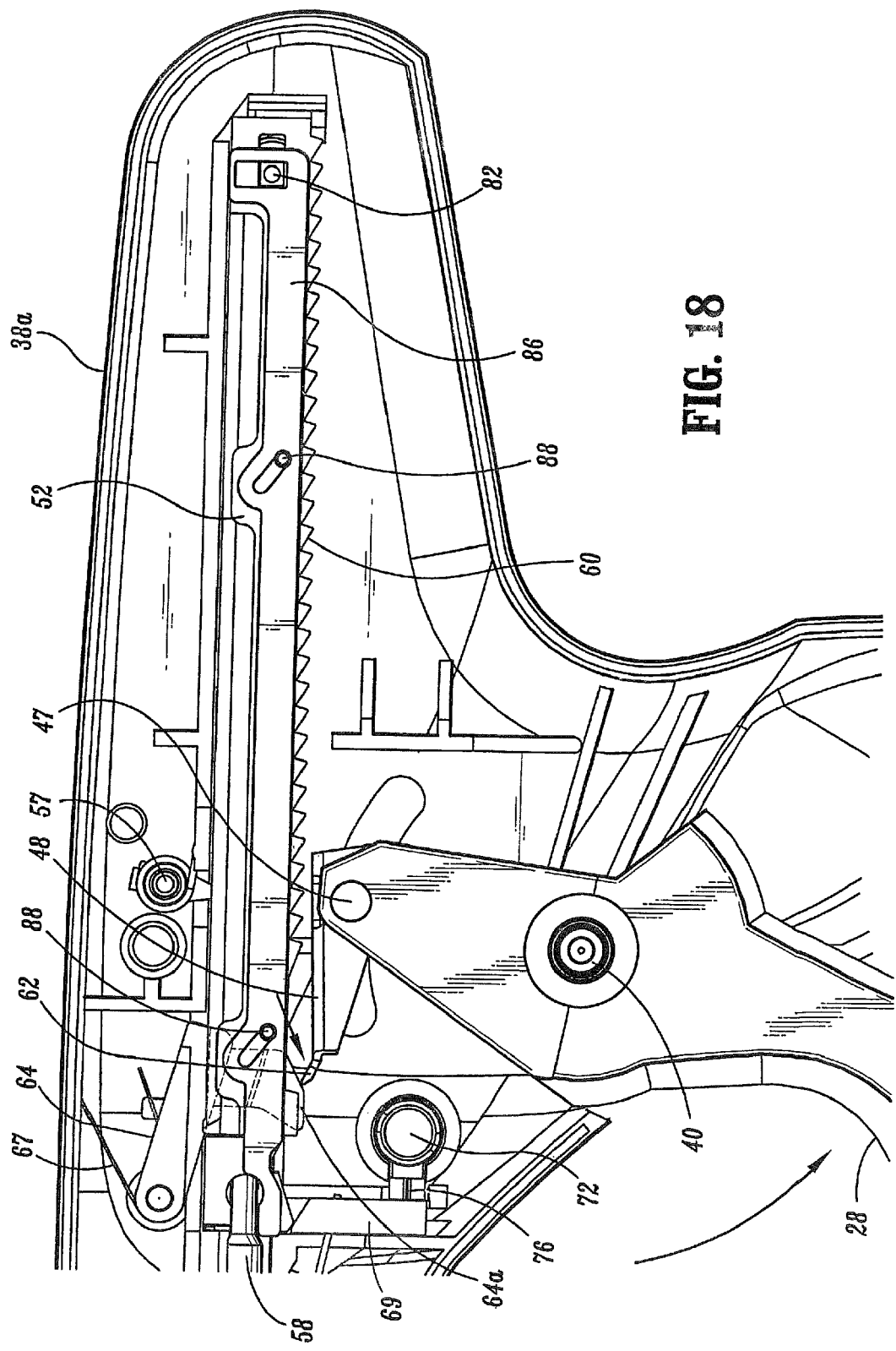
FIG. 18 is an enlarged side view, with portions broken away, of the handle assembly of the surgical stapling device shown in FIG. 2 with a housing half section removed and the pawl engaging the lock rack.

Referring to FIGS. 5, 13 and 14, rack lock 64 including pivot members 66 is pivotably supported about pivot members 66 between housing half-sections 38a and 38b. A biasing member 67a, which is preferably a torsion spring, is positioned to urge rack lock 64 in a clockwise direction as viewed in FIG, 5. Rack lock 64 includes blocking portion 64a which is positioned within housing 38 to prevent engagement between engagement finger 62 of pawl 48 and toothed rack 60 of actuation shaft 52 when a DLU 16 is not attached to stapling device 10 and movable handle 28 is compressed (See FIG. 18). When a DLU is attached to device 10, rack lock 64 is pivoted, in a manner to be described below, to move blocking portion 64a of rack lock 64 to a non-blocking position in which finger 62 of pawl 48 is free to engage toothed rack 60 of actuation shaft 52. Rack lock 64 also includes a locking portion 64b which is positioned Within a recess 52a of actuation shaft 52 to prevent axial movement of actuation shaft 52 until after a DLU 16 (FIG. 1) has been attached to the device.

Figure 19:
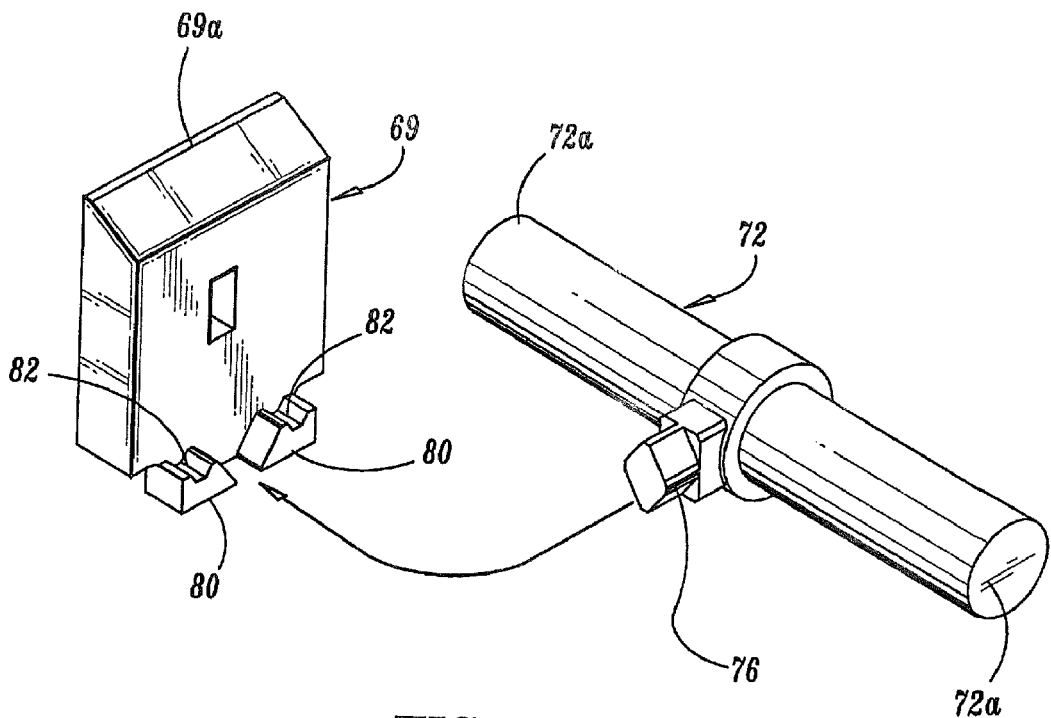
FIG. 19 is a top perspective view of the pawl and plunger mechanism of the surgical stapling device shown in FIG. 2.

Referring to FIGS. 5 and 19, a vertical pawl 69 is slidably positioned in a slot 68 defined between housing half-sections 38a and 38b. Vertical pawl 69 is movable from an extended or upward position in which the tip 69a of pawl 69 engages a notch 67 formed in the distal end of actuation shaft 52, to a retracted or downward position in which tip 69a of pawl 69 is spaced from actuation shaft 52. A spring 70 supported between housing half-sections 38a and 38b is positioned to urge pawl 69 to the extended position. In the extended position, pawl 69 prevents advancement of actuation shaft 52 to prevent firing of stapling device 10.

A plunger 72 is reciprocably supported between spaced cylindrical channels 74 formed in housing half-sections 38a and 38b. Plunger 72 includes a cam member 76. A spring 78 is positioned on each end of plunger 72 within cylindrical channels 74. Springs 78 urge plunger 72 to a position wherein cam member 76 is centrally positioned between a pair of cam surfaces 80 formed on vertical pawl 69. Each cam surface 80 has a recess 82a (FIG. 19) formed therein for releasably receiving cam member 76 of plunger 72.

Each end 72a (FIG. 1) of plunger 72 extends through stationary handle 26 and can be pressed against the bias of one of springs 78 to force cam member 76 into engagement with a respective one of cam surfaces 80 on vertical pawl 66. When cam member 76 is moved into engagement with one of cam surfaces 80, vertical pawl 69 is urged from the extended position to the retracted position to move tip 69a of vertical pawl 69 out of notch 67 of actuator shaft 52. See FIGS. 61 and 62. Stapling device 10 is now in a fire-ready position. The positioning of tip 76a of cam member 76 in recess 80a of a respective cam surface 80 retains vertical pawl in the retracted position to maintain device 10 in the fire-ready position.

Retraction Mechanism

A retraction mechanism which includes return knobs 36 (FIG. 1) is connected to the proximal end of actuation shaft 52 by a coupling rod 82. Coupling rod 82 has right and left engagement portions 82a and 82b which extend through elongated slots 83 (FIG. 1) formed in housing half-sections 38a and 38b and are configured to receive return knobs 36. A central portion 82c of coupling rod 82 is dimensioned to be slidably received within slots 84 formed in the proximal end of actuation shaft 52. A release plate 86 is supported on one side of actuation shaft 52 by a pair of pins 88. Pins 88 are positioned within angled cam slots 90 formed through release plate 86. Coupling rod 82 extends through an opening 92 formed in the proximal end of release plate 86.

In use, when knobs 36 are pulled rearwardly by a surgeon, coupling rod 82 initially moves release plate 86 rearwardly in relation to actuation shaft 52 as rod 82 slides in slots 84 of actuation shaft 52. As this occurs, pins 88 cam release plate 86 downwardly to a position covering toothed rack 60 of actuation shaft 52 to disengage finger 62 of pawl 48 from toothed rack 60. When coupling rod 82 is pulled rearwardly to a position at which it engages the back end 84a of slots 84, additional rearward movement knobs 36 effect proximal movement of actuation shaft 52 and firing rod 58.

Figure 8:
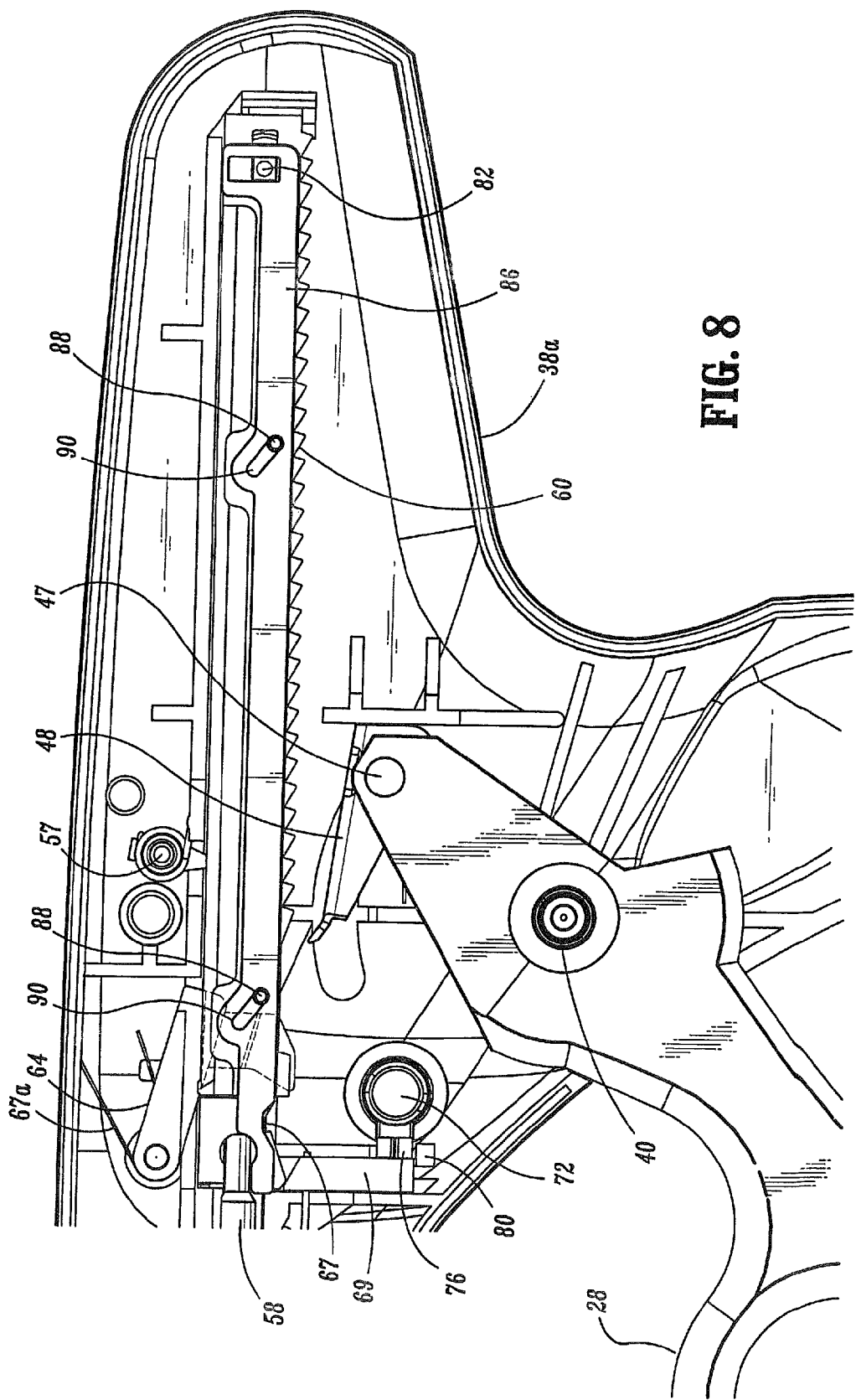
FIG. 8 is an enlarged side view of the handle assembly with portions broken away of the surgical stapling device shown in FIG. 2 with the housing half section removed.
Figure 9:
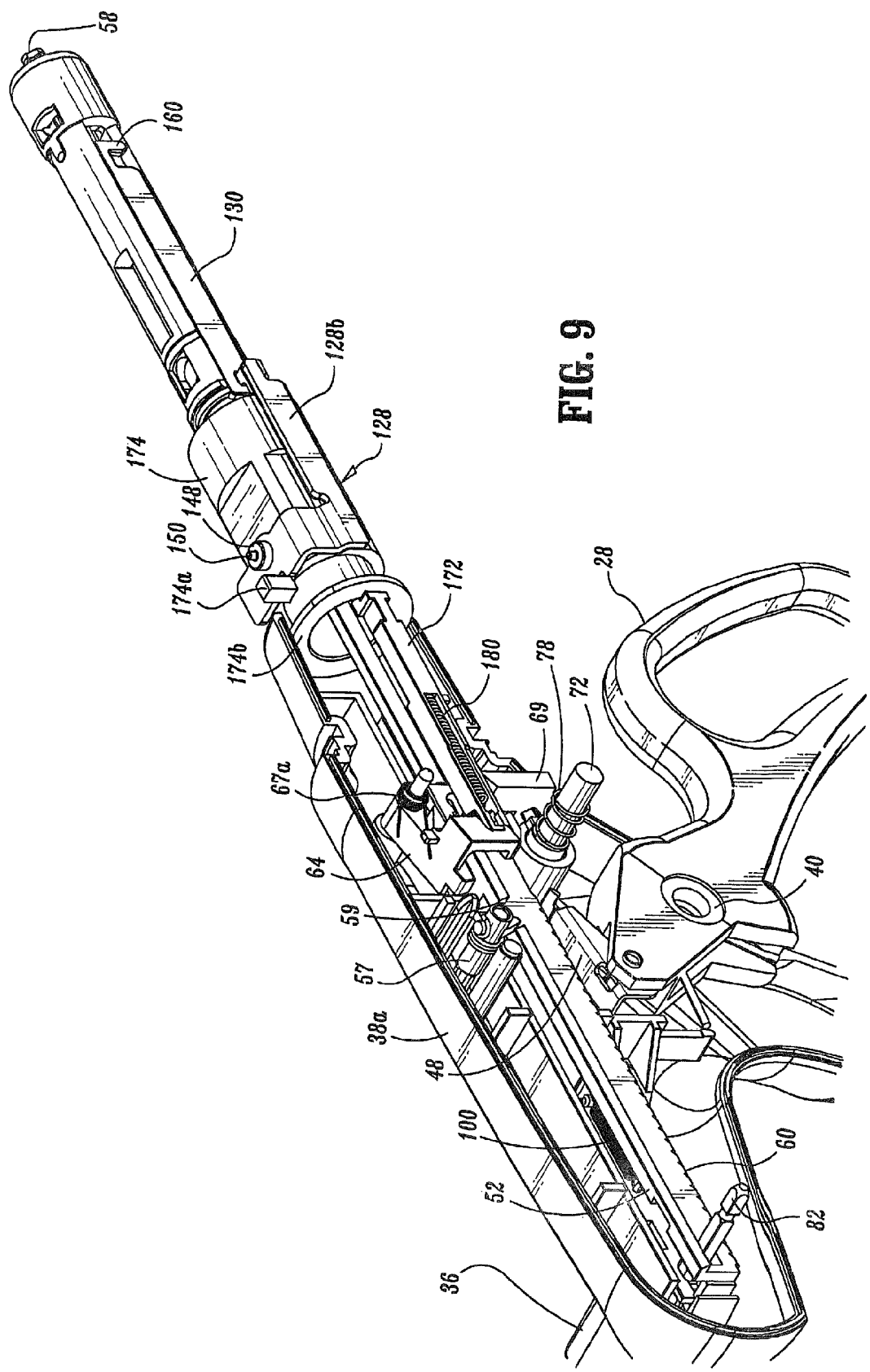
FIG. 9 is a rear side perspective view of the surgical stapling device shown in FIG. 2 with the housing half section, the rotatable knob, and the outer tube of the elongated body of the instrument removed.
Figure 10:
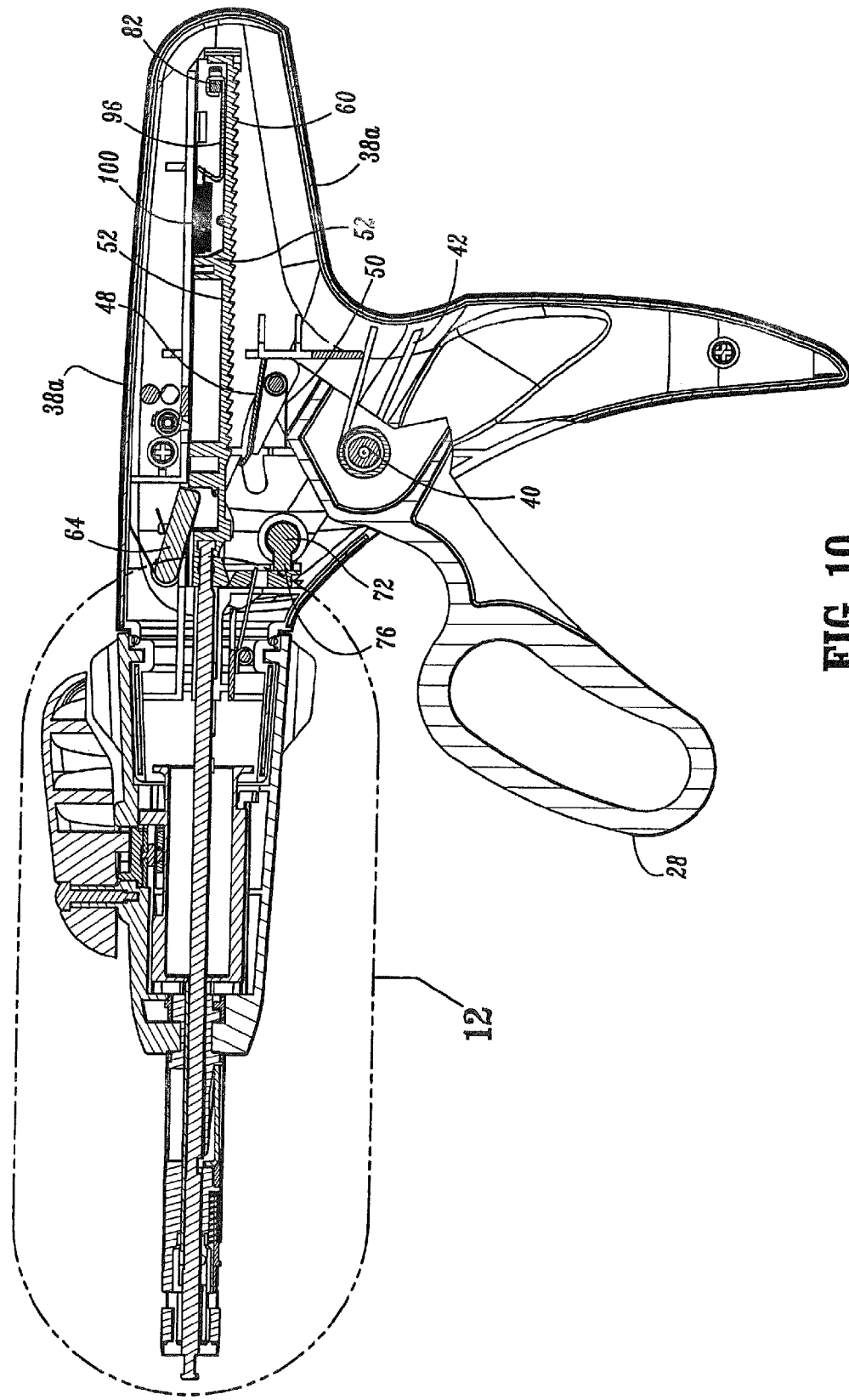
FIG. 10 is a side vertical cross sectional view of the surgical stapling device shown in FIG. 2.

A hook 96 is supported in a slot 98 formed in a top surface of actuation shaft 52. Hook 96 includes a throughbore 96a dimensioned to receive coupling rod 82. A forward end of hook 96 includes an upturned portion 98 configured to receive one looped end 100a of spring 100. The opposite end of spring 100 includes a loop 100b dimensioned to receive a post 102 formed on, actuation shaft 52. Spring 100 is maintained in tension to urge coupling rod 82 towards the forward end of slots 84 in actuation shaft 52. When coupling rod 82 is positioned at the forward end of slots 84 of actuation shaft 52, release plate 86 is held or caromed in a raised position above toothed rack 60 of actuation shaft 52 (FIG. 8).

Rotation Assembly

Referring to FIGS. 5 and 10-12, rotatable knob 32 is preferably formed from molded plastic half-sections 32a and 32b, although other materials, e.g., metals, and manufacturing methods are envisioned. The inner surface of the proximal end of rotatable knob 32 includes an annular ring 106 dimensioned to be received within an annular slot 108 formed in the forward end of barrel portion 30 of handle assembly 12 to rotatably attach knob 32 to handle assembly 12. An O-ring 107 is positioned between annular ring 106 and handle assembly 12 to create a friction drag between knob 32 and handle assembly 12. The friction drag prevents free rotation of knob 32 in relation to handle assembly 12. The outer surface of the proximal end of rotatable knob 32 includes a scalloped configuration 110 to facilitate gripping of rotatable knob 32. The inner surface of the distal end of rotatable knob 32 defines an opening 112 and includes a protrusion 114 configured to be received within openings 116 formed in the proximal end of elongated body 14. The central portion of rotatable knob 32 includes a post 118 and defines a transverse channel 120 configured to operably receive the articulation mechanism of the stapling device 10 as will be described in detail below.

Articulation Mechanism

Figure 11:
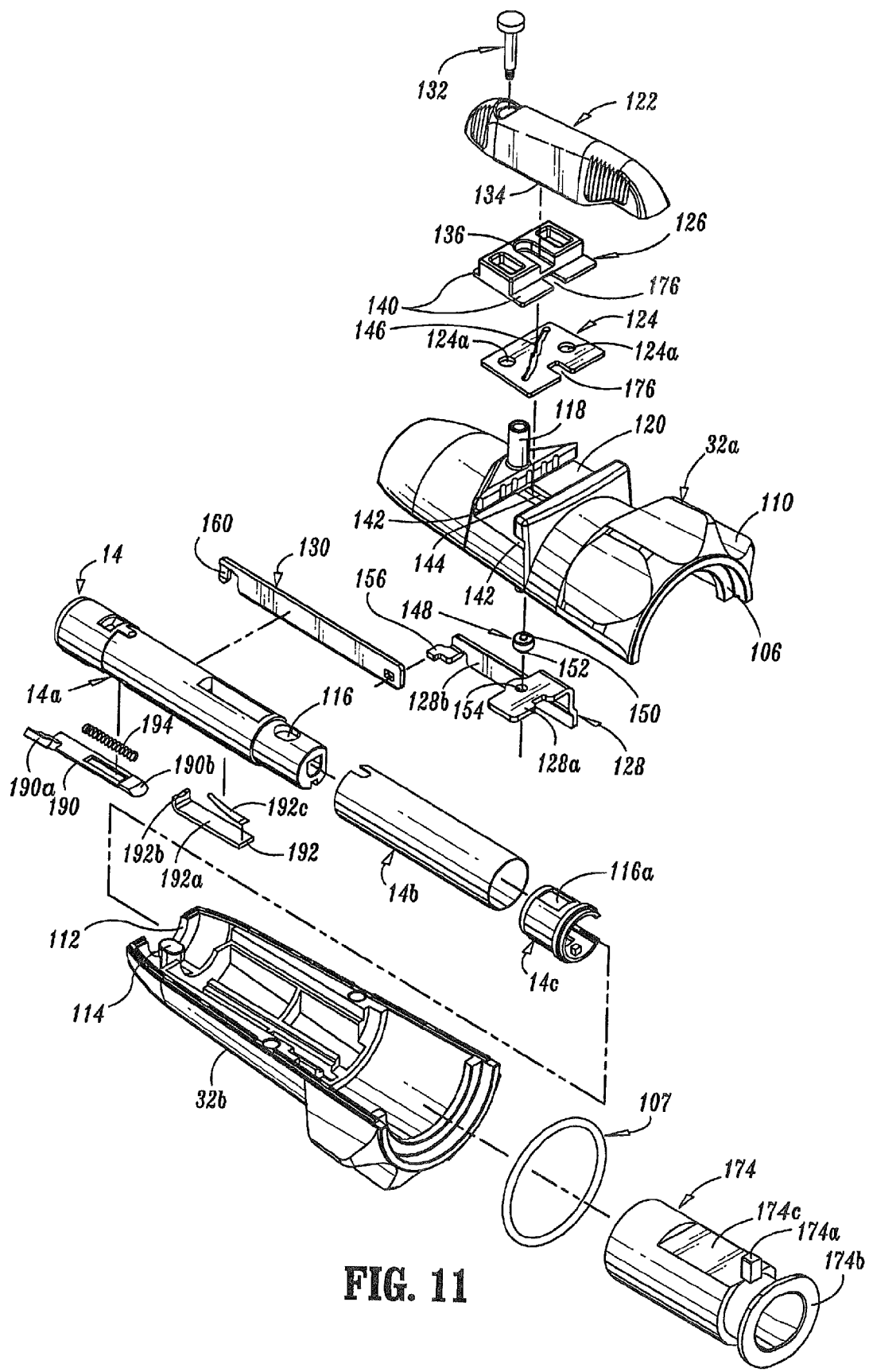
FIG. 11 is an exploded side perspective view of the rotatable knob and articulation assembly of the surgical stapling device shown in FIG. 2.

Referring also to FIG. 15, the articulation mechanism of the presently disclosed stapling device 10 includes an articulation lever 122, a cam member 124, a cam cover 126, a drive member 128 and an articulation member or link 130 (FIG. 11). Articulation lever 122 is rotatably secured to post 118 of rotatable knob 32 by a lever pin 132. Although lever pin 132 is shown as a separate element from lever 122, it is envisioned that pin 132 may be integrally formed with lever 122. A projection 134 (FIG. 12) extends downwardly from a bottom surface of lever 122 and is received within an elongated slot 136 formed in cam cover 126. Cam member 124 is fixedly secured to the base of cam cover 126 by a pair of press-fit projections 126a (FIG. 15) which are received within openings 124a formed in cam member 124. Alternately, other known fastening techniques including screws, snap-fit connectors, welding; interlocking members, etc., may be used to secure cam cover 126 to cam member 124. Cam cover 126 and cam member 124 define an assembly having front and rear ledges 140. The assembly is dimensioned to be slidably positioned in transverse channel 120. Ledges 140 are received within recesses 142 formed in channel 120 to prevent separation of the cam cover and cam member assembly from channel 120 and to limit the cam cover and cam member to linear movement. Preferably, cam cover 126 is formed of plastic and cam member 124 is formed of a metal, e.g., stainless steel. Alternately, other materials of construction are envisioned.

Transverse channel 120 of rotatable knob 32 includes a longitudinal slot 144 extending therethrough. Cam member 124 has a stepped cam slot 146 formed therethrough. A cam pin 148 includes a first projection 150 which extends upwardly as viewed in FIG. 12 through longitudinal slot 144 and is received within stepped cam slot 146 of cam member 124. Cam pin 148 also includes a second projection 152 which extends downwardly as viewed in FIG. 12 into an opening 154 formed in drive member 128.

Drive member 128 includes a body portion 128a including opening 154 and a longitudinal extension 128b. An engagement member 156 is formed at the distal end of longitudinal extension 128b. Engagement member 156 is configured to be received within an opening 158 formed in the proximal end of articulation link 130. The distal end of articulation link 130 also includes engagement structure 160 for engaging an articulation link positioned within a DLU 16 (FIG. 1) as will be described in detail below.

In operation, when articulation lever 122 is rotated about lever pin 132, projection 134 causes the cam cover 126 and cam member 124 assembly to move across transverse channel 120. Movement of cam member 124 across transverse channel 124 causes stepped cam slot 146 to move in relation to first projection 150 of cam pin 148, thus causing cam pin 148 to move through longitudinal slot 144. Longitudinal movement of cam pin 148 effects corresponding longitudinal movement of drive member 128 and articulation link 130. The interconnection of articulation link 130 and the articulation structure within DLU 16 will be described in detail below.

DLU Sensor Mechanism

Referring to FIGS. 5-12, surgical stapling device 10 includes a sensor mechanism for determining if a DLU 16 has been attached to elongated body 14. The sensor mechanism includes a sensor plate 170 (FIG. 5), a rack lock release member 172 and a sensor cap 174 (FIG. 11). When elongated body 14 is of an extended length, a sensor tube (not shown) may be positioned between sensor plate 170 and sensor cap 174 to translate movement of sensor plate 170 to sensor cap 174. Sensor plate 170 is slidably positioned along a flat 58a formed on firing rod 58 and includes a distal end 170a and a proximal end 170b. In an alternate embodiment, a shim or spacer 170c (FIG. 12A) may be positioned on sensor plate 170 between an inner wall of elongated body 14. Shim 170c functions to maintain sensor plate 170 in slidable contact with firing rod 58 and in alignment with sensor cap 174, thus preventing sensor plate 170 from overriding and losing axial contact with sensor cap 174. Although shown as being a separate element from sensor plate 170, shim 170c may be integrally or monolithically formed with sensor plate 170. Sensor cap 174 is slidably positioned within rotatable knob 32 between advanced and retracted positions and includes an articulation locking tab 174a, a proximal flange 174b, and an upper flat surface 174c. (See FIG. 11.) Upper flat surface 174c is positioned within rotatable knob 32 beneath transverse channel 120 such that tab 174a extends upwardly through an opening in knob 32 into a cutout 176 formed in cam cover 126 and cam member 124. When sensor cap 174 is in the advanced position, tab 174a is positioned within cutout 176 to prevent movement of cam member 124 along transverse channel 120 to prevent articulation of surgical stapling device 10. When sensor cap 174 is moved to the retracted position, in a manner to be described below, tab 174a is moved proximally from cutout 176 to permit movement of cam member 124 along transverse channel 120 and thus, permit articulation of surgical stapling device 10.

Rack lock release member 172 includes a distal end 172a configured to engage flange 174b of sensor cap 174 and a proximal end 172b positioned adjacent rack lock 64. A biasing member 180, preferably a coil spring, is positioned within a slot 172c formed in rack lock release member 172 between one end of slot 172c and a finger (not shown) extending into slot 172c from housing assembly 12 to urge lock rack release member 172 distally and thus urge sensor cap 174 and sensor plate 170 distally to the advanced position.

In operation, when a DLU is not attached to surgical stapling device 10, biasing member 180 maintains lock rack release member 172, sensor cap 174 and sensor plate 170 in their advanced positions. As discussed above, in the advanced position, sensor cap locking tab 174a is positioned within cam member cutout 176 to prevent articulation of surgical stapling device 10. In the advanced position, lock rack release member 172 is also spaced from rack look 64 such that locking portion 64b of rack lock 64 is positioned within a recess 52a formed in actuation shaft 52 to lock actuation shaft 52 in a fixed retracted position and blocking portion 64a of rack lock 64 is positioned to prevent engagement of pawl 48 and toothed rack 60 of actuation shaft 52. When a DLU 16 is secured to the distal end of elongated body 14, the proximal end of the DLU engages distal end 170a of sensor plate 170 to move sensor plate 170 proximally. Proximal movement of sensor plate 170 effects corresponding proximal movement of sensor cap 174 and lock rack release member 172. Proximal movement of sensor cap 174 to the retracted position removes locking tab 174a from cam member cutout 176 to permit selective articulation of stapling device 10. When lock rack release member 172 is moved proximally, the proximal end 172b of member 172 abuts against a bottom surface of rack lock 64 to pivot locking portion 64b of rack lock 64 upwardly out of recess 52a of actuation shaft 52 to facilitate advancement of actuation shaft 52 and to pivot blocking portion 64a of rack lock 64 to a position not obstructing engagement between engagement finger 62 of pawl 48 and toothed rack 60 of actuation shaft 52.

Referring to FIGS. 11, 12, 16 and 17, elongated body 14 includes a body portion 14a, a body cover 14b and an end cap 14c. Body cover 14b is positioned about body portion 14a and end cap 14c is secured to the proximal end of body portion 14a. Elongated body 14, as discussed above, is secured between rotatable knob half-sections 32a and 32b via protrusions 114 formed on half-sections 32a and 32b positioned within openings 116 formed in the proximal end of body portion 14a (openings 116a are also formed through end cap 14c). Elongated body 14 defines a longitudinal throughbore through which firing rod 58, sensor plate 170, and articulation link 130 extend. As discussed above, when elongated body 14 is of an extended length, a sensor tube may also be provided within elongated body 14.

Figure 12:
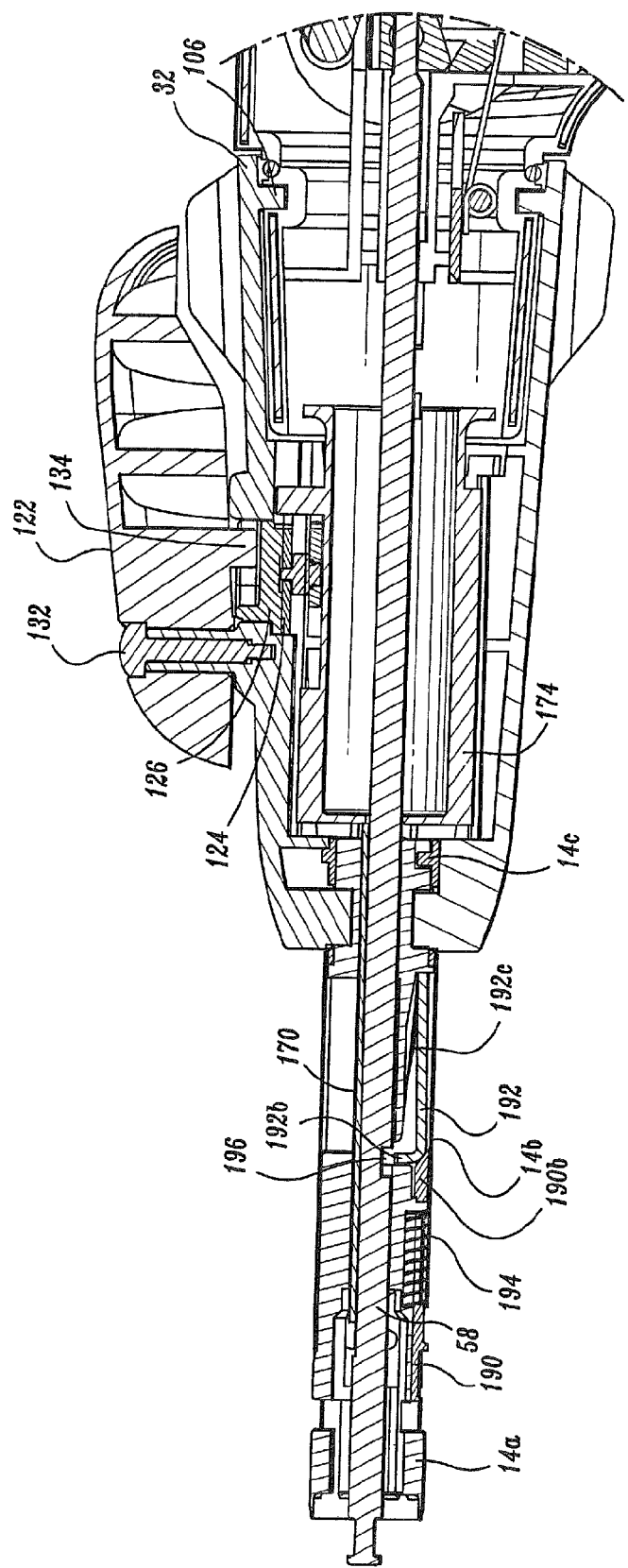
FIG. 12 is a side cross sectional view of the rotatable knob, articulation assembly and elongated body of the surgical stapling device shown in FIG. 1.
Figure 12A:
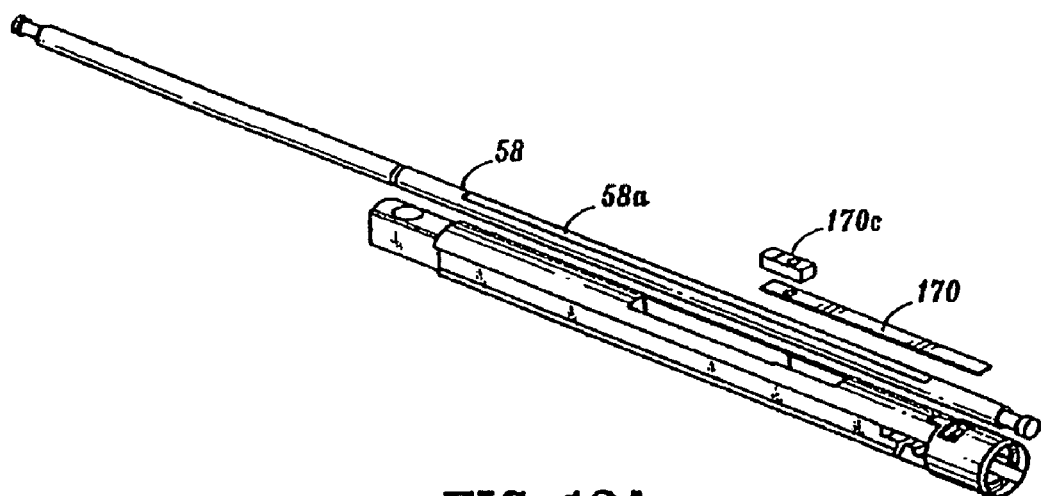
FIG. 12A is an exploded side perspective view of the elongated body; firing rod, sensor plate and shim of the surgical stapling device shown in FIG. 1.

A lock button 190 and a plate and spring assembly 192 are supported in recesses formed in elongated body 14. Lock button 190 is slidably positioned distally of spring assembly 192 (See FIG. 12) adjacent the distal end of elongated body 14 and includes a distal engagement finger 190a and a proximal tapered abutment surface 190b. Finger 190a is positioned to engage the proximal end of a DLU 16 (FIG. 1) during attachment of the DLU 16 to elongated body 14. A biasing member 194 is provided to urge lock button 190 in a distal direction. Plate and spring assembly 192 includes a plate 192a having a blocking portion 192b and a spring member 192c. Spring member 192c is preferably a leaf spring which is secured directly to plate 192a. Alternately, other configurations are envisioned, e.g., the plate and the spring member are separate elements. Blocking portion 192b is positioned adjacent to a notch 196 formed in firing rod 58 (FIG. 12).

When a DLU is attached to the distal end of elongated body 14, as will be described in further detail below, the DLU is inserted into elongated body 14 and rotated in relation to elongated body 14 to lock DLU 16 thereon. During insertion of DLU 16 into elongated body 14, the proximal end of DLU 16 engages finger 190a of look button 190 and forces lock button 190 proximally against the bias of spring 194 such that abutment surface 190b of lock button 190 engages plate 192a of assembly 192. Engagement between abutment surface 190b and plate 192a moves blocking portion 192b, against the bias of spring member 192c, into notch 196 of firing rod 58 to lock firing rod 58 in an axially fixed position to prevent firing of the device until the DLU has been rotated to the locked position. When the DLU is rotated to the locked position, spring 194 returns lock button 190 to its distal position spaced from plate 192a and spring member 192c urges blocking portion 192b from notch 196 of firing rod 58 to permit axial movement of firing rod 58. Preferably, movement of lock button 190 to its distal position provides an audible indication that the DLU is locked on elongated body 14.

Figure 20:
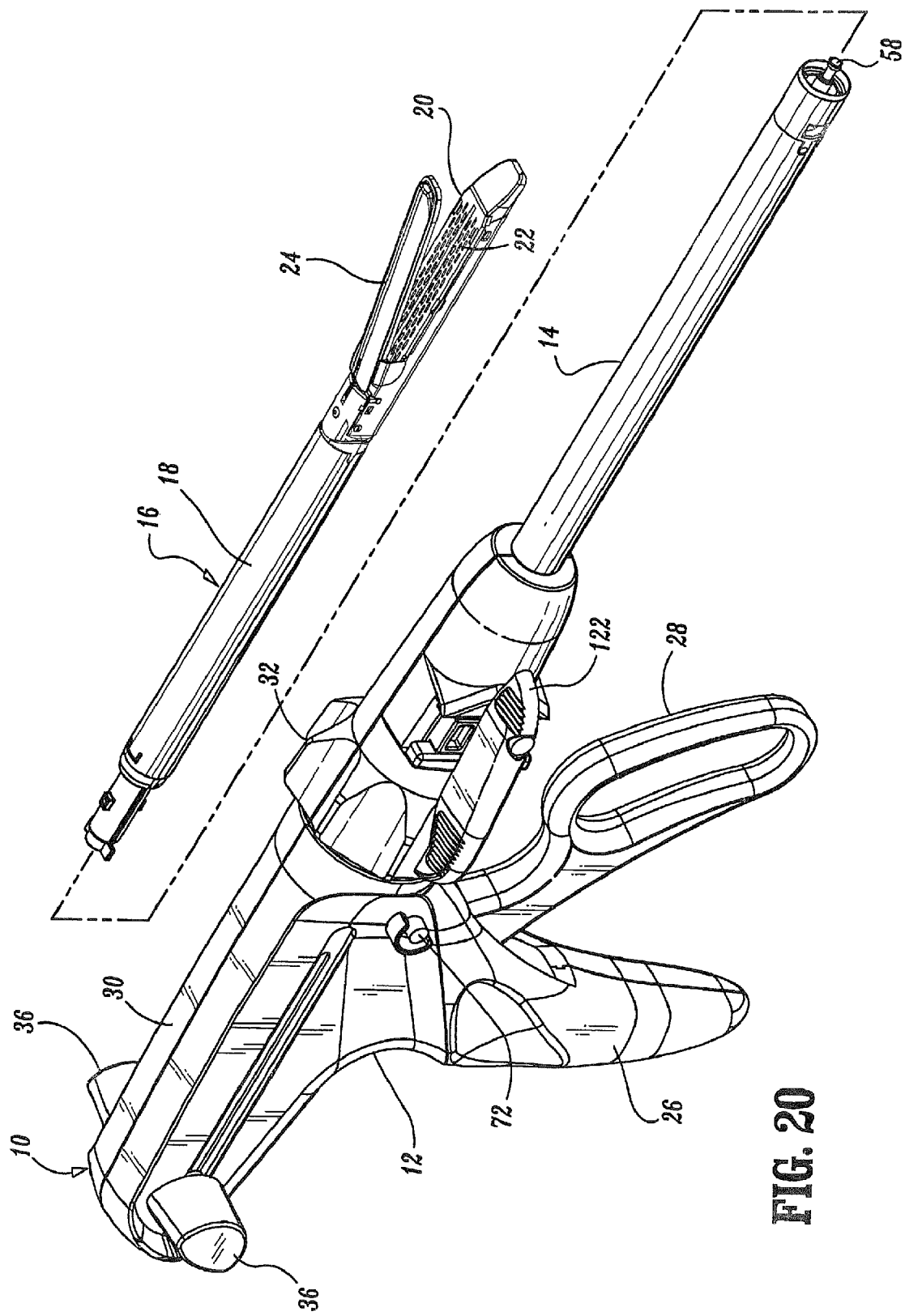
FIG. 20 is a top front perspective view of the surgical stapling device shown in FIG. 2 with the disposable loading unit detached from the elongated body.

FIG. 20 illustrates surgical stapling device 10 and a DLU 16 prior to attachment of the DLU to elongated body 14 of device 10. As discussed above, prior to attachment of DLU 16 to device 10, movable handle 16 is rendered inoperable by rack lock 64 which prevents pawl 48 from engaging toothed rack 60 of actuation shaft 52 and locks actuation shaft 52 in a fixed axial position.

Figure 21:
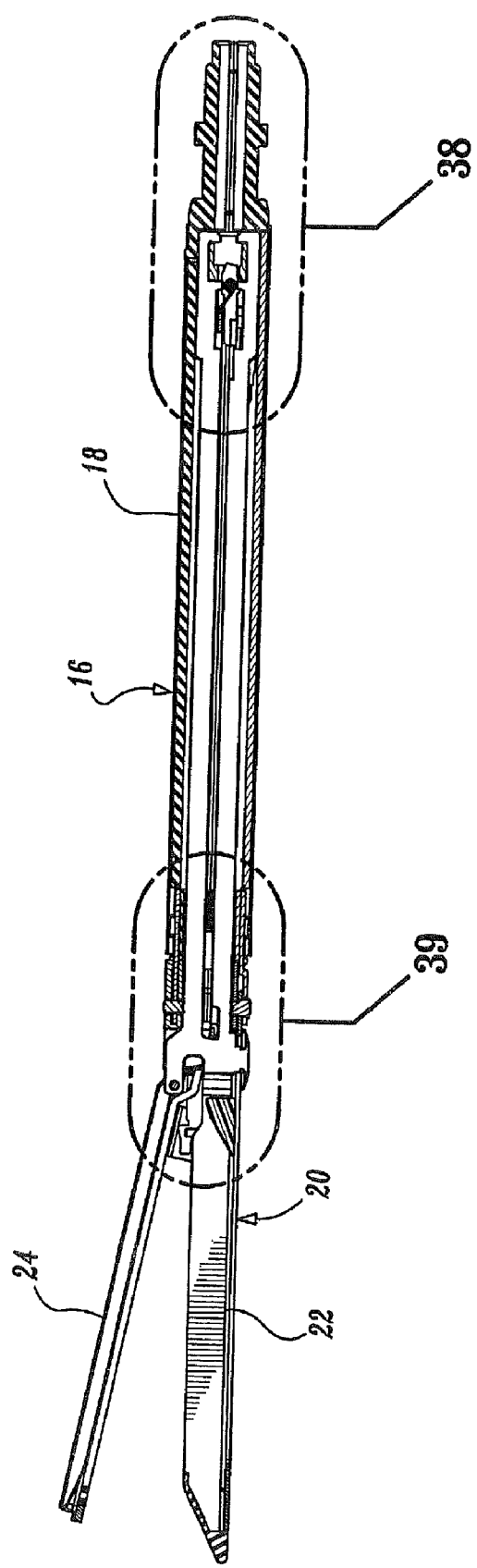
FIG. 21 is a side cross sectional view of the disposable loading unit of the surgical stapling device shown in FIG. 2.
Figure 28:
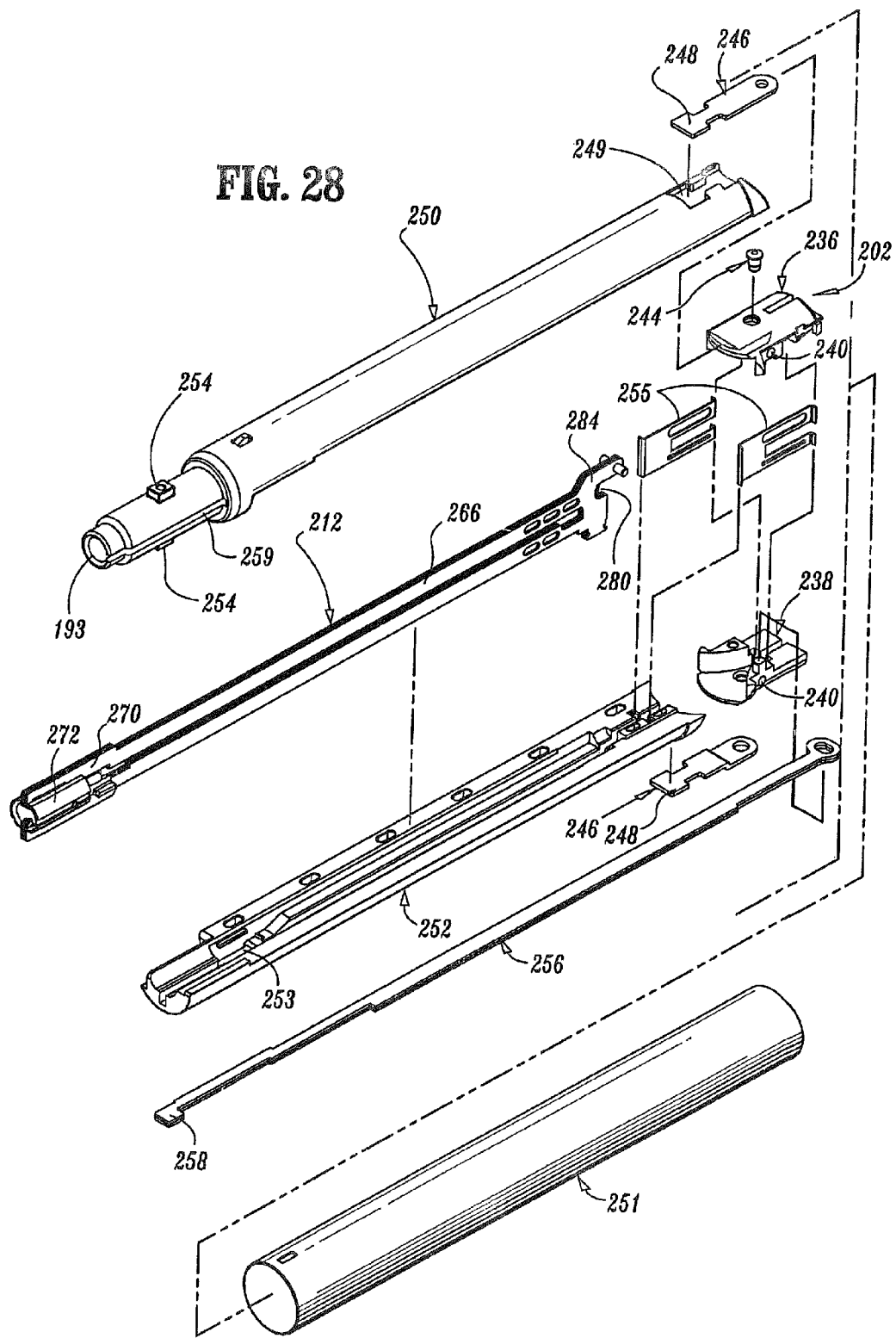
FIG. 28 is an enlarged exploded top perspective view of the proximal body portion and mounting assembly of the disposable loading unit shown in FIG. 21.
Figure 28A:
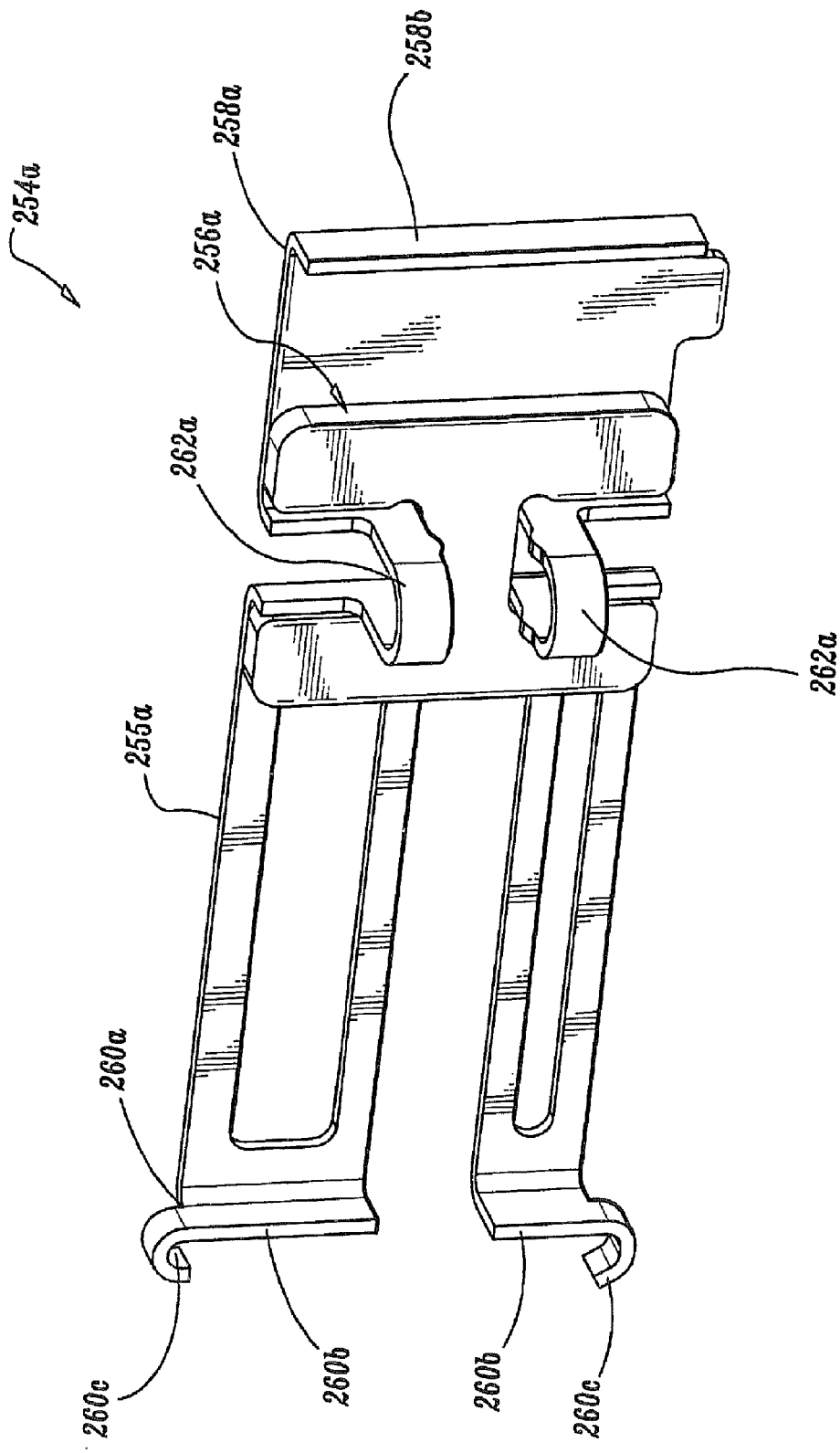
FIG. 28a is an enlarged side perspective view of the blow out plate assembly of the surgical stapling device shown in FIG. 2.

Referring also to FIG. 21, disposable loading unit 16 includes proximal body portion 18 which is configured to releasably engage the distal end of elongated body 14, and distal tool assembly 20 which is pivotally secured to the distal end of body portion 18 by a mounting assembly 202 (FIG. 28).

Figure 22:
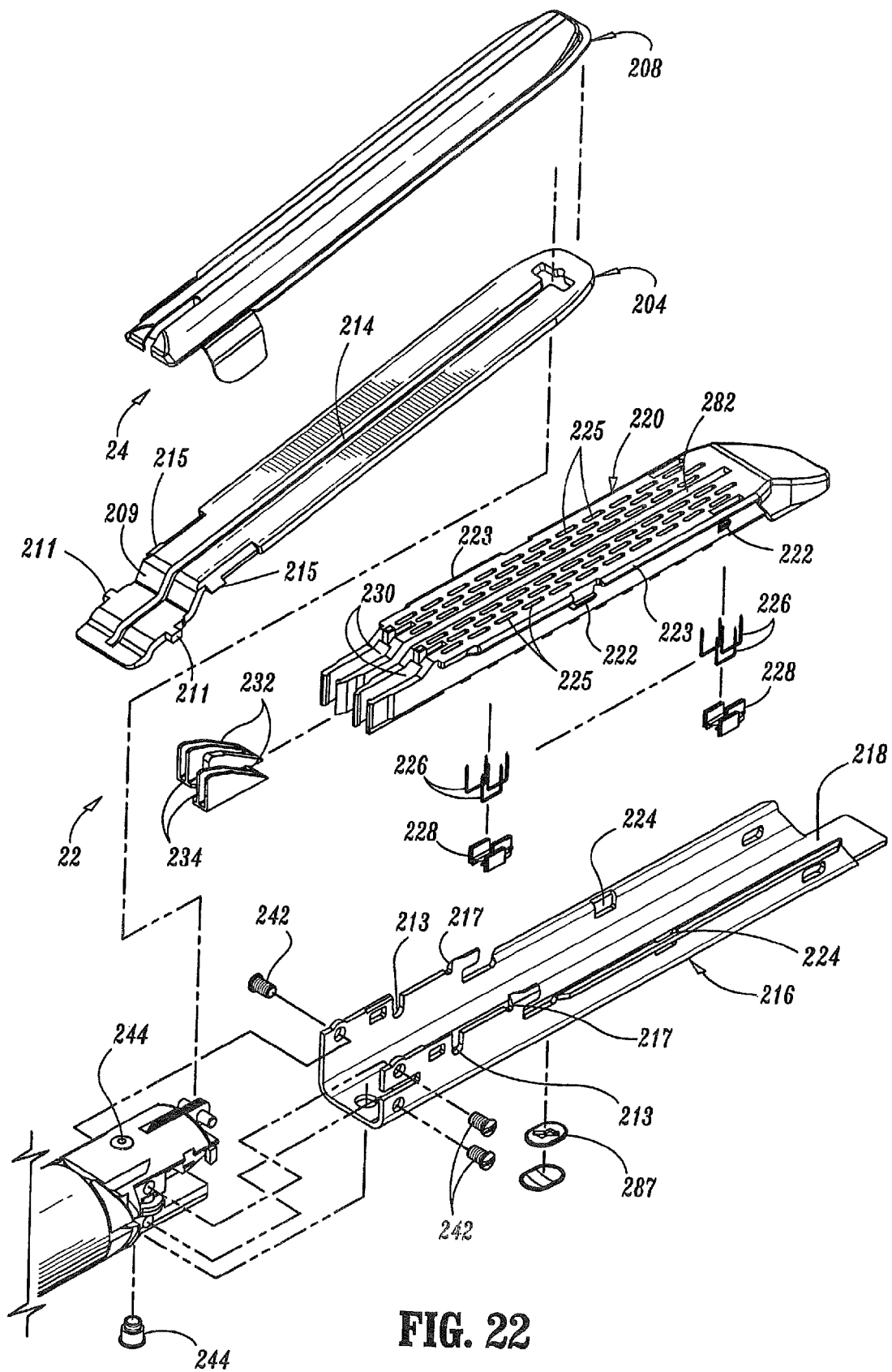
FIG. 22 is an exploded top perspective view of the tool assembly of the disposable loading unit shown in FIG. 21.
Figure 23:
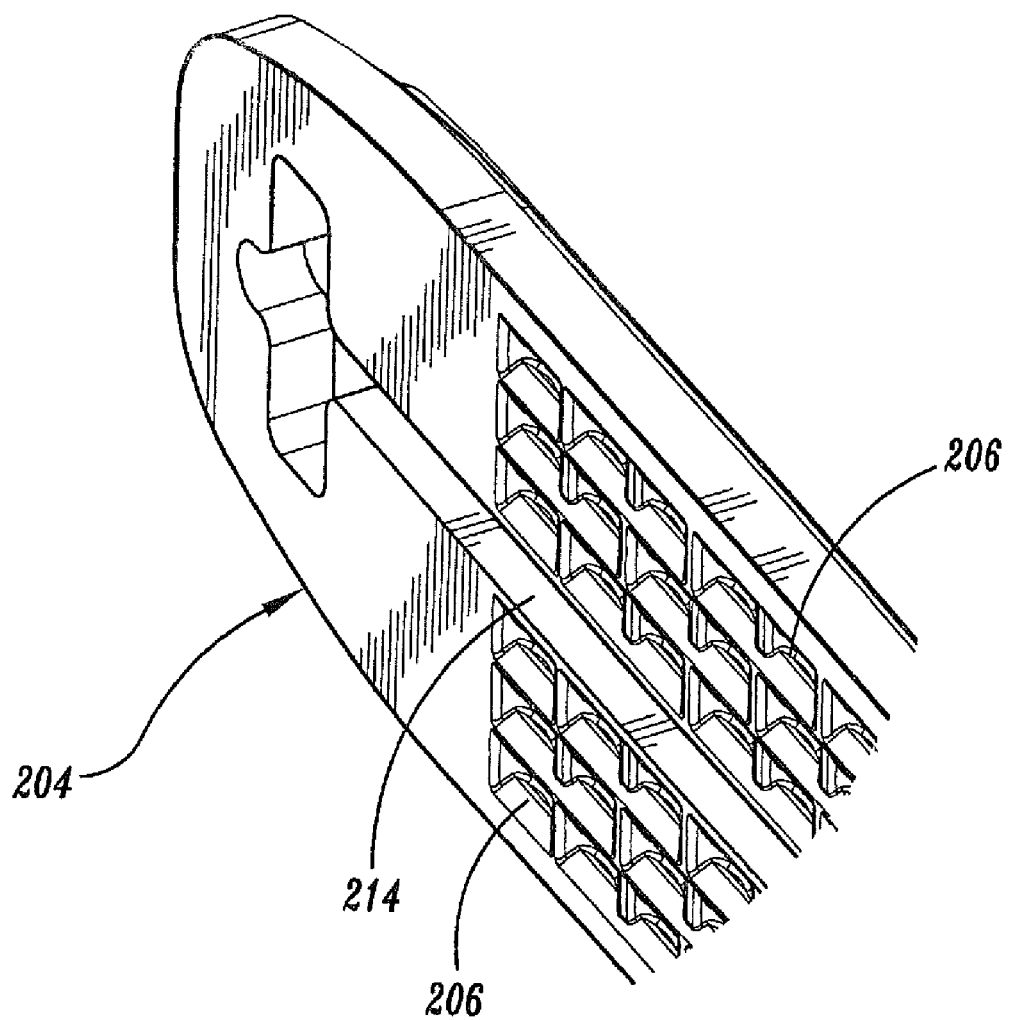
FIG. 23 is an enlarged perspective view, with portions broken away, of the distal end of the anvil assembly of the surgical stapling device shown in FIG. 2 showing a plurality of staple forting cavities.
Figure 24:
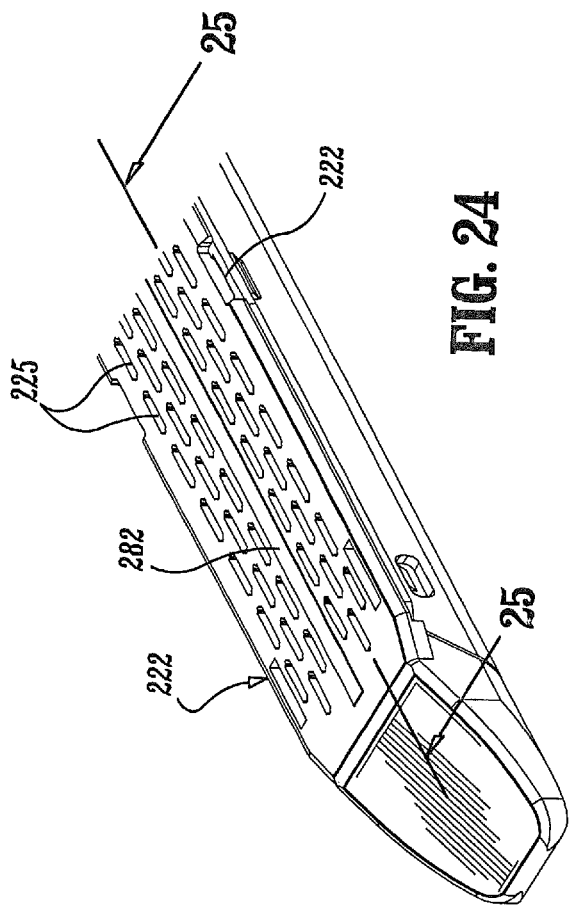
FIG. 24 is an enlarged top perspective view of the distal end of the staple cartridge of the surgical stapling device shown in FIG. 2.
Figure 25:
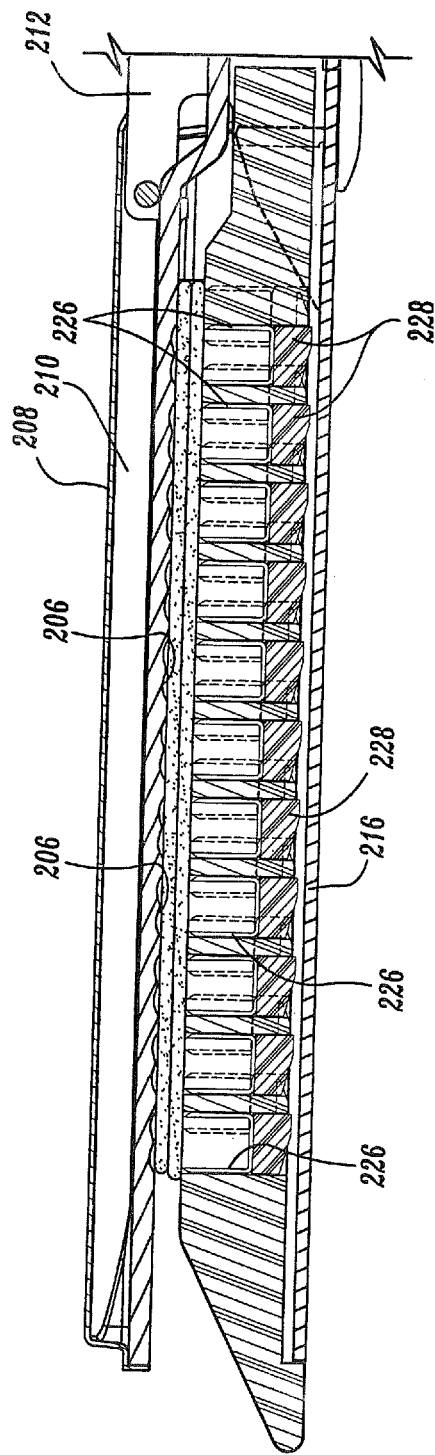
FIG. 25 is a side cross sectional view taken along a portion of section lines 25-25 of FIG. 24.

Referring also to FIGS. 22-28, tool assembly 20 includes anvil assembly 24 and cartridge assembly 22 (FIG. 22). Anvil assembly 24 has anvil portion 204 having a plurality of staple deforming concavities 206 (FIG. 23) and a cover plate 208 secured to a top surface of anvil portion 204 to define a cavity 210 (FIG. 25) therebetween. Cover plate 208 is provided to prevent pinching of tissue during approximation and firing of stapling device 10. Cavity 210 is dimensioned to slidably receive a distal end of an axial drive assembly 212 (See FIG. 28). A longitudinal slot 214 extends through anvil portion 204 to facilitate passage of retention flange 284 (FIG. 28) of axial drive assembly 212 through anvil cavity 210. A camming surface 209 formed on anvil portion 204 is positioned to be engaged by axial drive assembly 212 to facilitate approximation of the anvil and cartridge assemblies and clamping of tissue 198 (FIG. 25). A pair of pivot members 211 formed on anvil portion 204 are positioned within slots 213 formed in carrier 216 to guide the anvil portion between the spaced and approximated positions. A pair of stabilizing members 215 engage a respective shoulder 217 formed on carrier 216 to prevent anvil portion 204 from sliding axially relative to staple cartridge 220 as camming surface 209 is pivoted about pivot members 211.

Cartridge assembly 22 includes carrier 216 which defines an elongated support channel 218. Elongated support channel 218 is dimensioned and configured to receive a staple cartridge 220. Corresponding tabs 222 and slots 224 formed along staple cartridge 220 and elongated support channel 218, respectively, function to retain staple cartridge 220 at a fixed location within support channel 218. A pair of support struts 223 formed on staple cartridge 220 are positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280 (FIG. 28). During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Referring to FIGS. 28 and 29, mounting assembly 202 includes upper and lower mounting portions 236 and 238. Each mounting portion includes a threaded bore 240 on each side thereof dimensioned to receive threaded bolts 242 (See FIG. 22) for securing the proximal end of carrier 216 thereto. A pair of centrally located pivot members 244 extends between upper and lower mounting portions 236 and 238 through a pair of coupling members 246 which engage the distal end of body portion 18. Coupling/members 246 each include an interlocking proximal portion 248 configured to be received in grooves 249 formed in the proximal end of body portion 18 to retain mounting assembly 202 and body portion 18 in a longitudinally fixed position in relation thereto, Body portion 18 of disposable loading unit 16 includes an upper housing half 250 and a lower housing half 252 contained within an outer casing 251. The proximal end of housing half 250 includes engagement lugs 254 for releasably engaging elongated body 14 in a bayonet coupling type fashion. The proximal end of housing half 250 also includes as insertion tip 193 which will be discussed in further detail below. Housing halves 250 and 252 define a channel 253 for slidably receiving axial drive assembly 212. A second articulation link 256 is dimensioned to be slidably positioned within a slot 258 formed between housing halves 250 and 252. A pair of blow out plates 255 are positioned adjacent the distal end of body portion 18 adjacent the distal end of axial drive assembly 212 to prevent outward bulging of drive assembly 212 during articulation and firing of tool assembly 20.

Figure 28B:
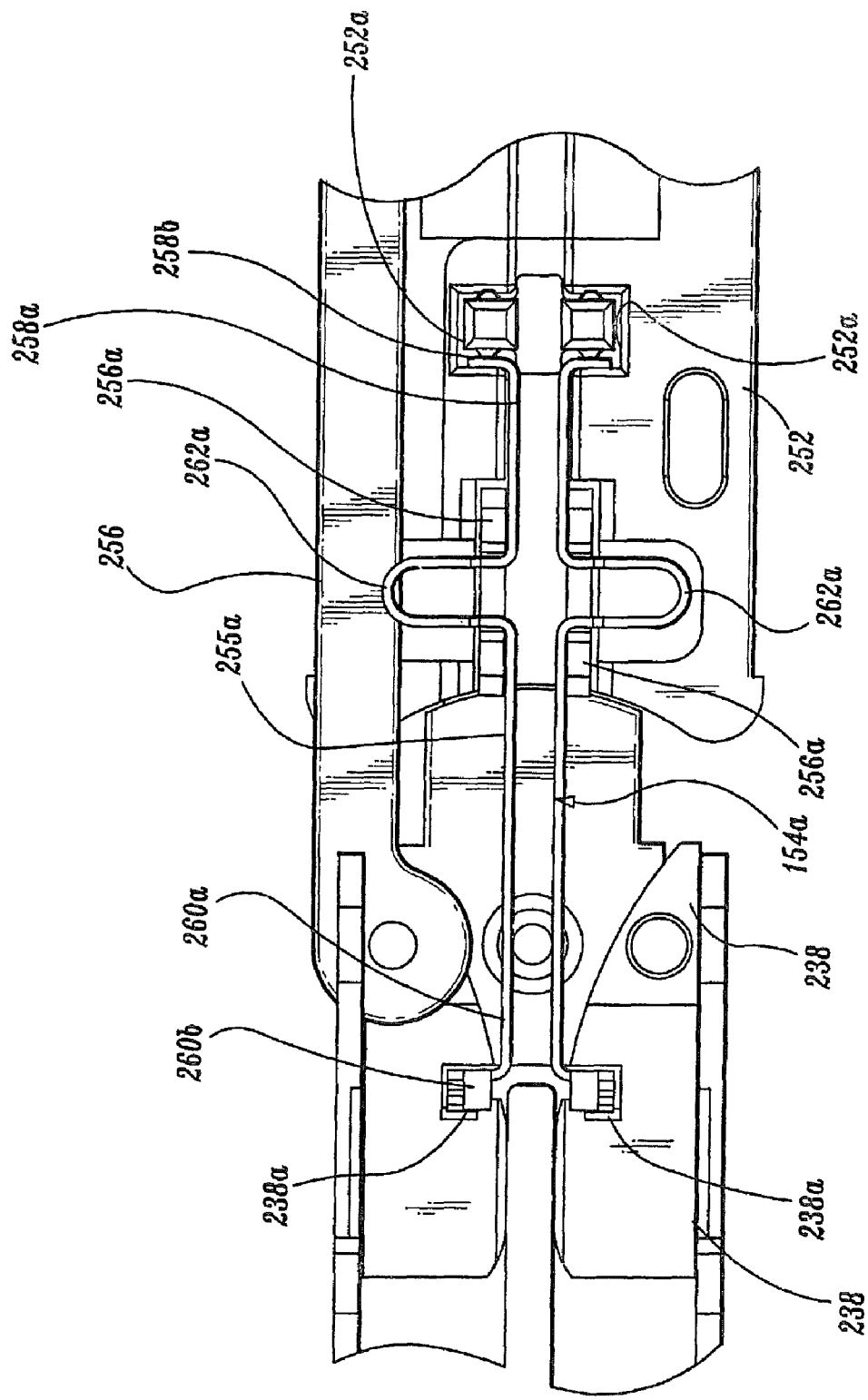
FIG. 28b is a top view, with portions broken away, of the proximal end of the tool assembly and the distal end of the proximal body portion of the disposable loading unit with the top housing half of the disposable loading unit removed.
Figure 28C:
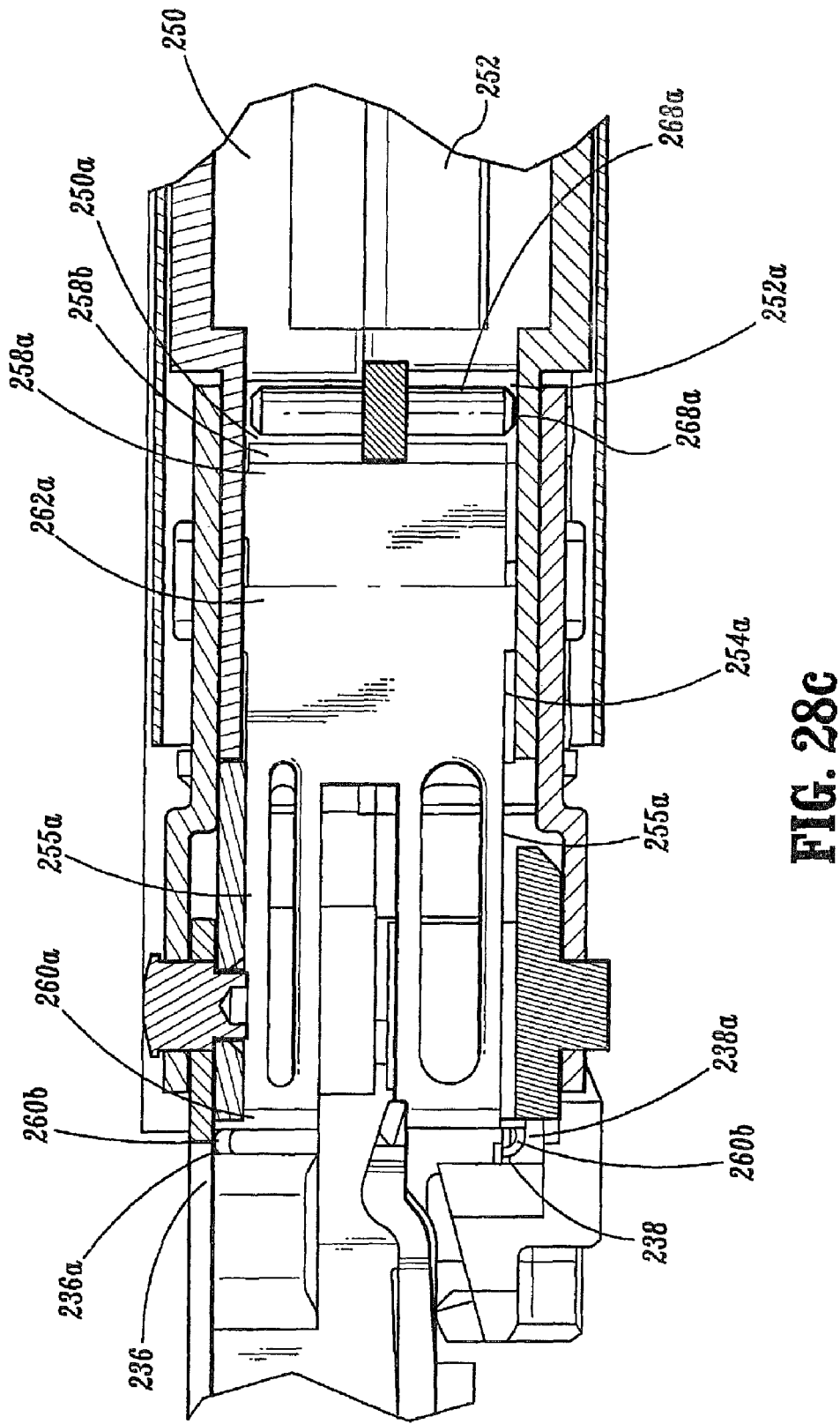
FIG. 28c is a side vertical cross sectional view of the proximal end of the tool assembly and the distal end of the proximal body portion of the disposable loading unit of the surgical stapling device shown in FIG. 2.
Figure 28F:
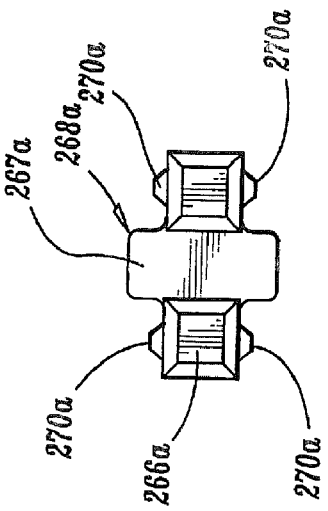
FIG. 28f is a top view, with portions broken away, of the locking member shown in FIG. 28d.
Figure 28E:
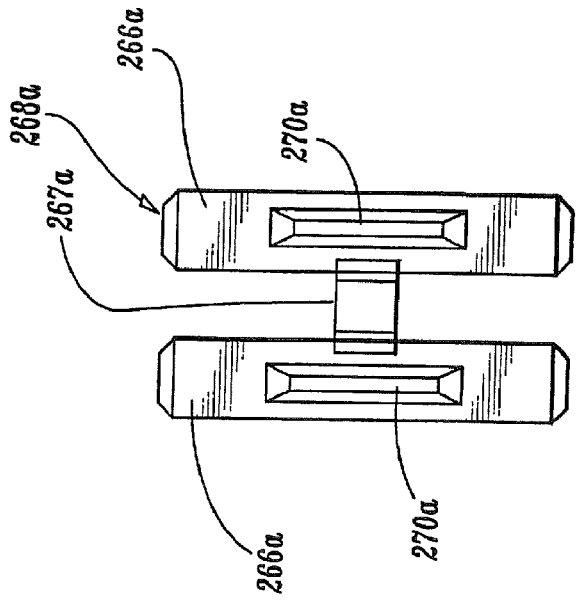
FIG. 28e is a front elevational view of the locking member shown in FIG. 28d.
Figure 28D:
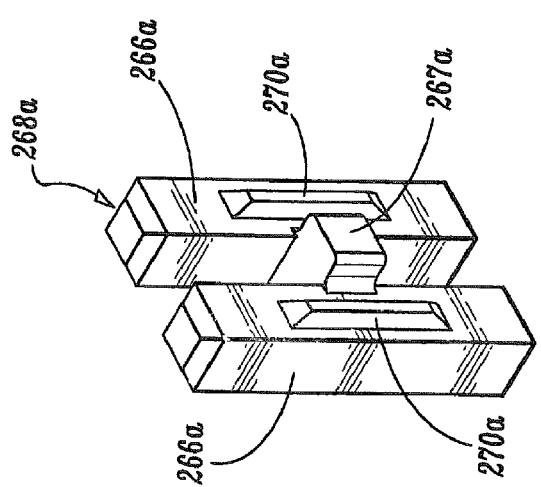
FIG. 28d is a top perspective view of the locking member of the blow out plate assembly of the surgical stapling device shown in FIG. 2.
Figure 28H:
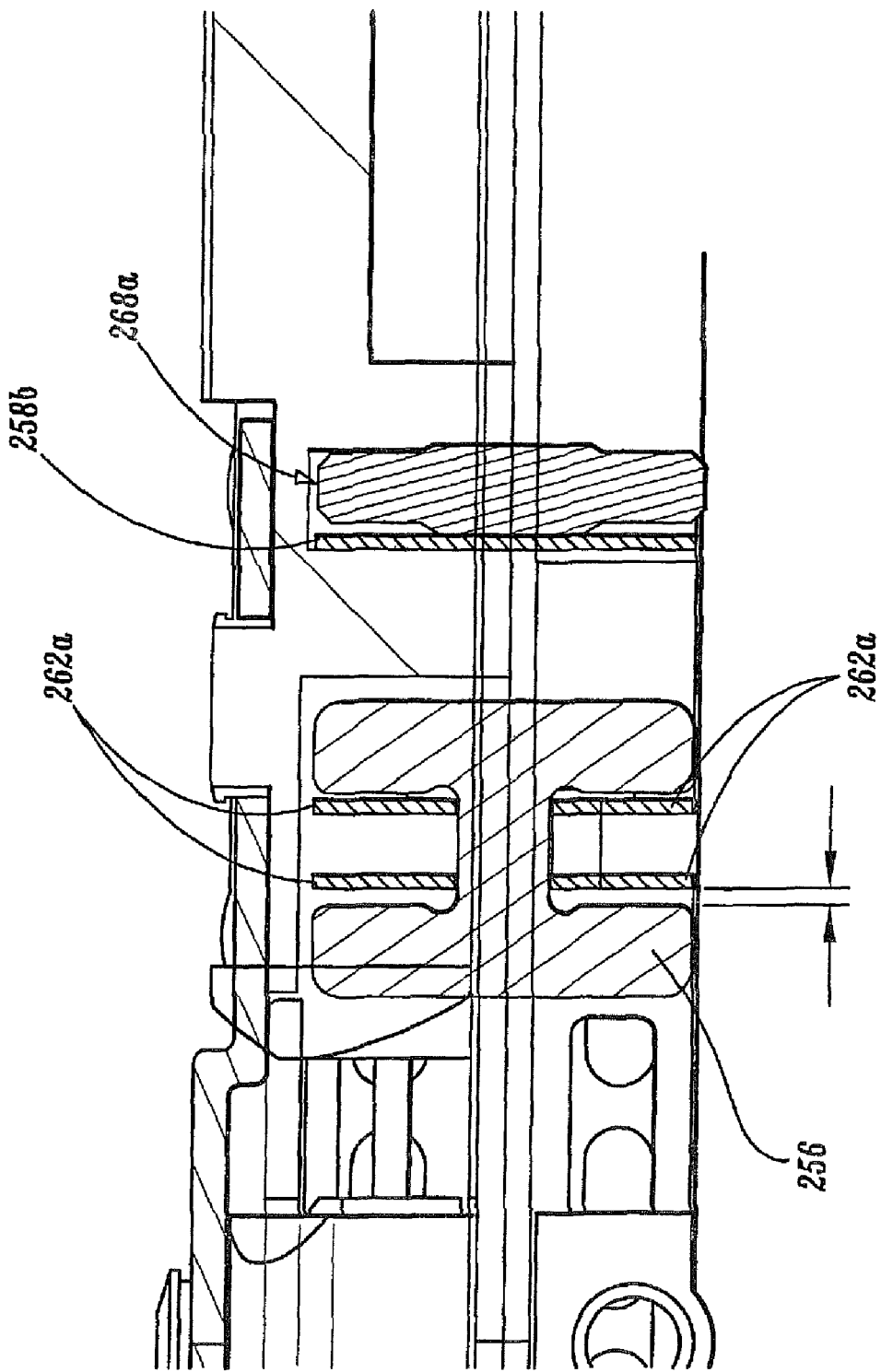
FIG. 28h is a transverse cross sectional view, with portions broken away, of the proximal end of the tool assembly and the distal end of the proximal body portion of the disposable loading unit of the surgical stapling device shown in FIG. 2.
Figure 32:
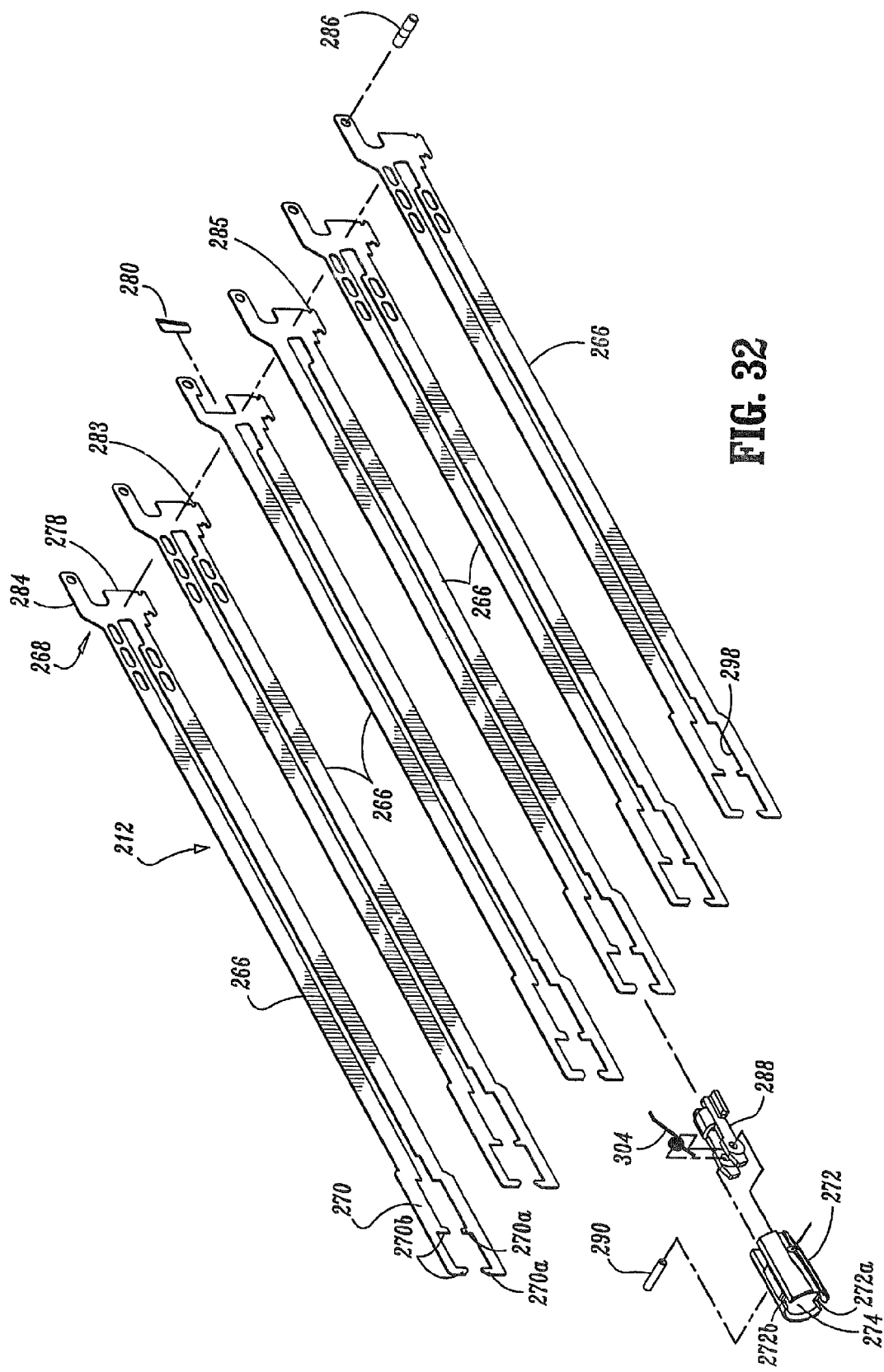
FIG. 32 is a perspective view with parts separated of the axial drive assembly of the surgical stapling device shown in FIG. 2.
Figure 36:
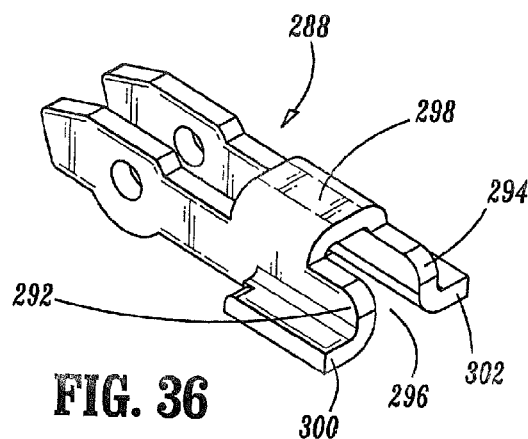
FIG. 36 is an enlarged perspective view of the locking device shown in FIG. 32.

FIGS. 28a-h illustrate an alternate embodiment of blow out plates 255 shown generally as blow out plate assembly 254a. Blow out plate assembly 254a includes a flexible body 255a and an H-block 256a. flexible body 255a has a proximal end 258a and a distal end 260a, The distal and proximal ends each include a retaining portion 258b and 260b, respectively. Retaining portion 258b is configured to be and is fixedly received and engaged within recesses 250a and/or 252a formed in respective upper and/or lower housing halves 250 and 252 of DLU 16 (FIG. 28b). Retaining section 260b includes a pair of J-shaped attachment members configured to be and which are fixedly received and engaged within recesses 236a and 238a formed in respective upper and/or lower mounting portions 236 and 238 of mounting assembly 202. The tips 260c of J-shaped attachment members are angled to engage and lock into recesses 236a and 238b (FIG. 28g), and are preferably press-fit into the walls that form recesses. A locking member 268a (FIGS. 28d-f) includes an H-shaped body having a pair of legs 266a and a central web 267a. Each leg 266a includes an elongated retaining protrusion 270a having tapered ends. Locking member 268a is dimensioned to be and is press fit within recesses 250a and 252a formed in respective upper and lower housing halves 250 and 252 of DLU 16 adjacent retaining section 258b to fixedly secure the retaining section 258b within the recesses. A central portion of blow out plate assembly 254a includes a pair of substantially U-shaped spring portions 262a. U-shaped spring portion 262a allows the central portion of body 255a to flex slightly outwardly to accommodate sliding and articulating movement of drive assembly 212 (FIG. 28) when tool assembly 20 is actuated, i.e., approximated or fired. As shown in FIG. 28h, H-block 256A is positioned with a small gap about spring portions 262a to limit the extent to which U-shaped spring portions 262a are able to flex to prevent buckling of the blow out plate assembly 254a and drive assembly 212 during actuation of device 10. A blow-out plate assembly 254a is positioned on each side of drive assembly 212 to prevent outward buckling of drive assembly 212 during actuation of device 10, including when device 10 is articulated.

Referring to FIGS. 30 and 31, second articulation link 256 includes at least one elongated metallic plate. Preferably, two or more metallic plates are stacked to form link 256. The proximal end of articulation link 256 includes a hook portion 258 configured to engage articulation link 130 (See FIG. 6) and the distal end includes a loop 260 dimensioned to engage a projection 262 formed on mounting portion 238 of mounting assembly 202, Projection 262 is laterally offset from pivot pin 244 such that linear movement of second articulation link 256 causes mounting assembly 202 to pivot about pivot pins 244 to articulate tool assembly 20 in relation to body portion 18.

Referring also to FIGS. 32-35 and 39, axial drive assembly 212 includes an elongated drive beam 266 including a distal working head 268 and a proximal engagement section 270. Drive beam 266 may be constructed from a single sheet of material or, preferably, multiple stacked sheets. Engagement section 270 includes a pair of engagement fingers 270a and 270b which are dimensioned and configured to mountingly engage a pair of corresponding retention slots 272a and 272b formed in drive member 272. Drive member 272 includes a proximal porthole 274 configured to receive the distal end 276 of firing rod 58 (See FIG. 12) when the proximal end of disposable loading unit 16 is engaged with elongated body 14 of surgical stapling apparatus 10.

The distal end of working head 268 of chive beam 266 is defined by a vertical support strut 278 (FIG. 32) which supports a knife blade 280, and an abutment surface 283 which engages the central portion of actuation sled 234 during a stapling procedure. Surface 285 is located at the base of surface 283 and is configured to receive a support member 287 (FIG. 39) which is slidably positioned along the bottom of the staple cartridge 220. Knife blade 280 is positioned to translate slightly behind actuation sled 234 through a central longitudinal slot 282 in staple cartridge 220 (FIG. 22) to form an incision between rows of stapled body tissue. A retention flange 284 projects distally from vertical strut 278 and supports a cylindrical cam roller 286 at its distal end. Cain roller 286 is dimensioned and configured to engage cam surface 209 on anvil body 204 to clamp anvil portion 204 against body tissue.

Referring also to FIGS. 21 and 36-38, a locking device 288 is pivotally secured to drive member 270 about a pivot pin 290. Locking device 288 includes a pair of elongate glides 292 and 294 which define a channel 296. A web 298 joins a portion of the upper surfaces of glides 292 and 294, and is configured and dimensioned to fit within elongated slot 298 formed in drive beam 266 at a position distal of drive member 272. Horizontal cams 300 and 302 extend from glides 292 and 294 respectively, and are accommodated along an inner surface of lower housing half 252. As best shown in FIG. 38, a torsion spring 304 is positioned adjacent drive member 270 and engages horizontal cams 300 and 302 (FIG. 36) of locking device 288 to normally bias locking device 288 downward toward lower housing half 252 onto ledge 310. Locking device 288 translates through housing portion 200 with axial drive assembly 212. Operation of locking device 288 will be described below.

FIGS. 80-96 illustrate an alternate embodiment of the presently disclosed disposable loading unit. As discussed above with respect to DLU 16, DLU 516 includes a mounting assembly 522. Mounting assembly 522 includes upper and lower mounting portions 580 and 582. A centrally located pivot member 584 extends from each of upper and lower mounting portions 580 and 582 through an opening 586a formed in a coupling member 586 which engages the distal end of proximal body portion 518. Coupling members 586 each include an interlocking proximal portion 588 configured to be received in grooves 590 formed in the proximal end of body portion 518 to retain mounting assembly 522 and body portion 518 in a longitudinally fixed position in relation to each other.

Body portion 518 of disposable loading unit 516 (FIG. 21) includes an upper housing half 592 and a lower housing half 594 contained within an outer casing 596. The proximal end of housing half 592 includes engagement lugs 596 for releasably engaging the distal end of instrument 10 (FIG. 20) and an insertion tip 598. Lugs 596 form a bayonet type coupling with the distal end of instrument 10. Housing halves 592 and 594 define a channel 600 for slidably receiving axial drive assembly 536. An articulation link 602 is dimensioned to be slidably positioned within a slot 604 formed housing upper and lower housing halves 592 and 594. A pair of blow out plate assemblies 606 are positioned adjacent the distal end of body portion 518 adjacent the distal end of axial drive assembly 536 to prevent outward buckling and/or bulging of drive assembly 536 during articulation and firing of tool assembly 520.

Figure 81:
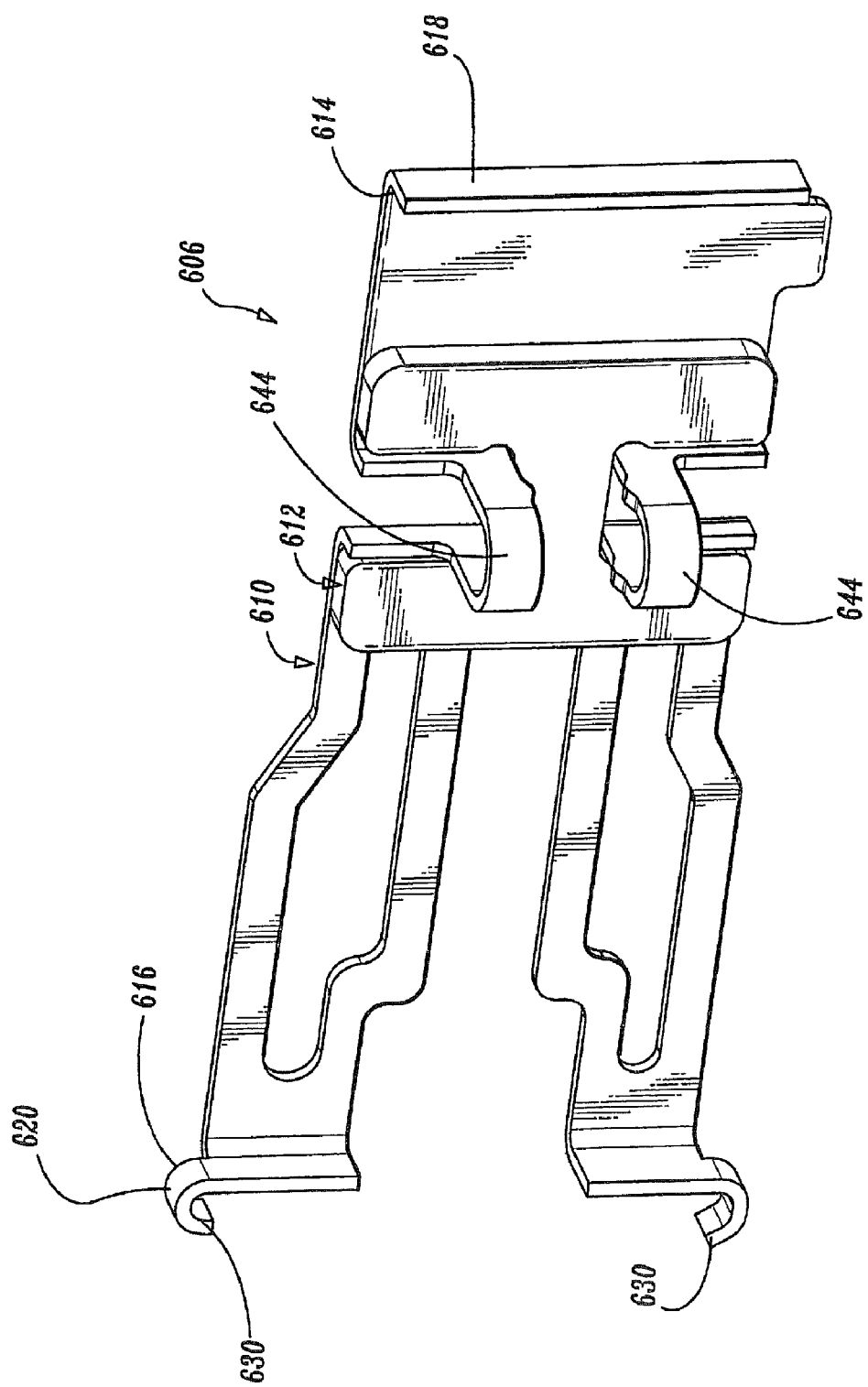
FIG. 81 is an enlarged side perspective view of the blow out plate assembly of the disposable loading unit shown in FIG. 80.
Figure 82:
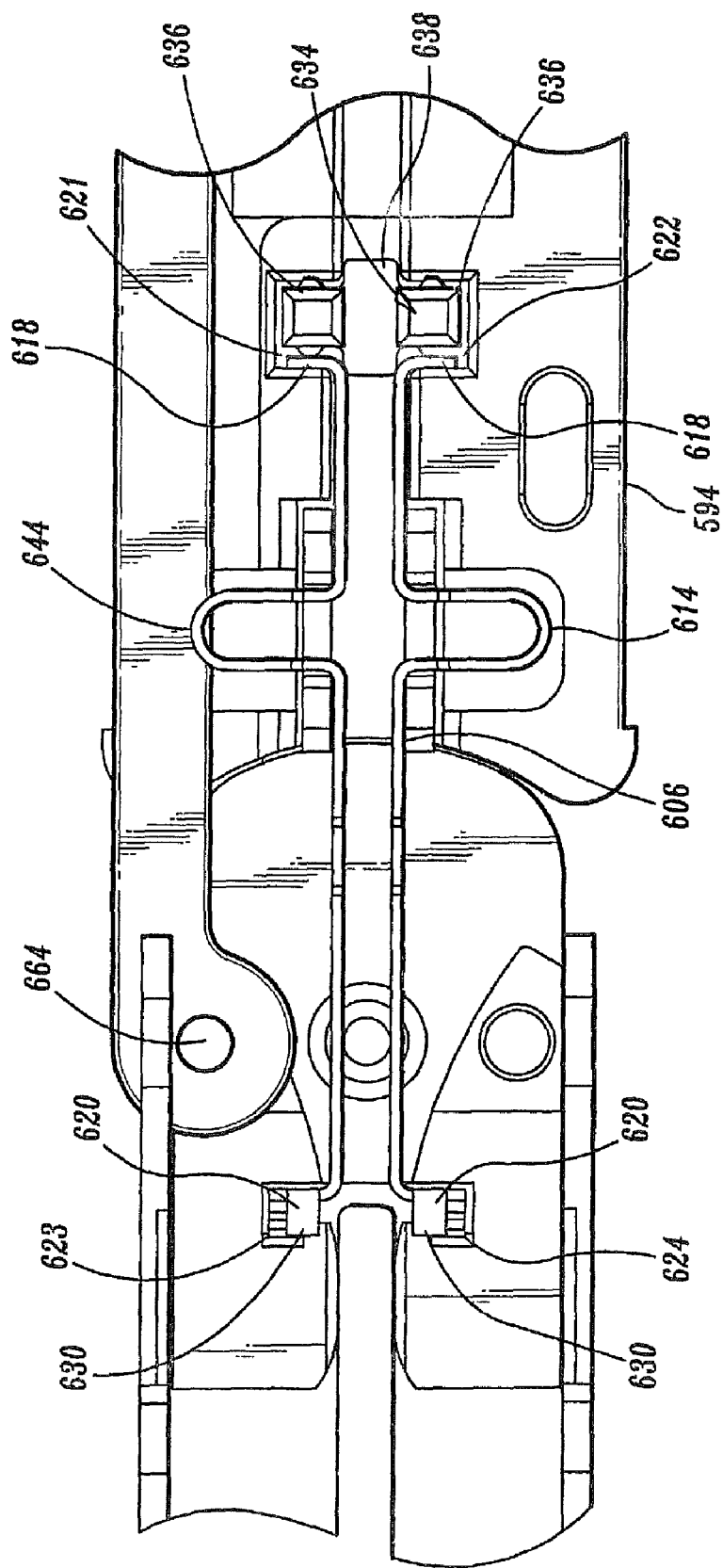
FIG. 82 is a top view, with portions broken away, of the proximal end of the tool assembly and the distal end of the proximal body portion of the disposable loading unit shown in FIG. 80 with the top housing half of the disposable loading unit removed.
Figure 83:
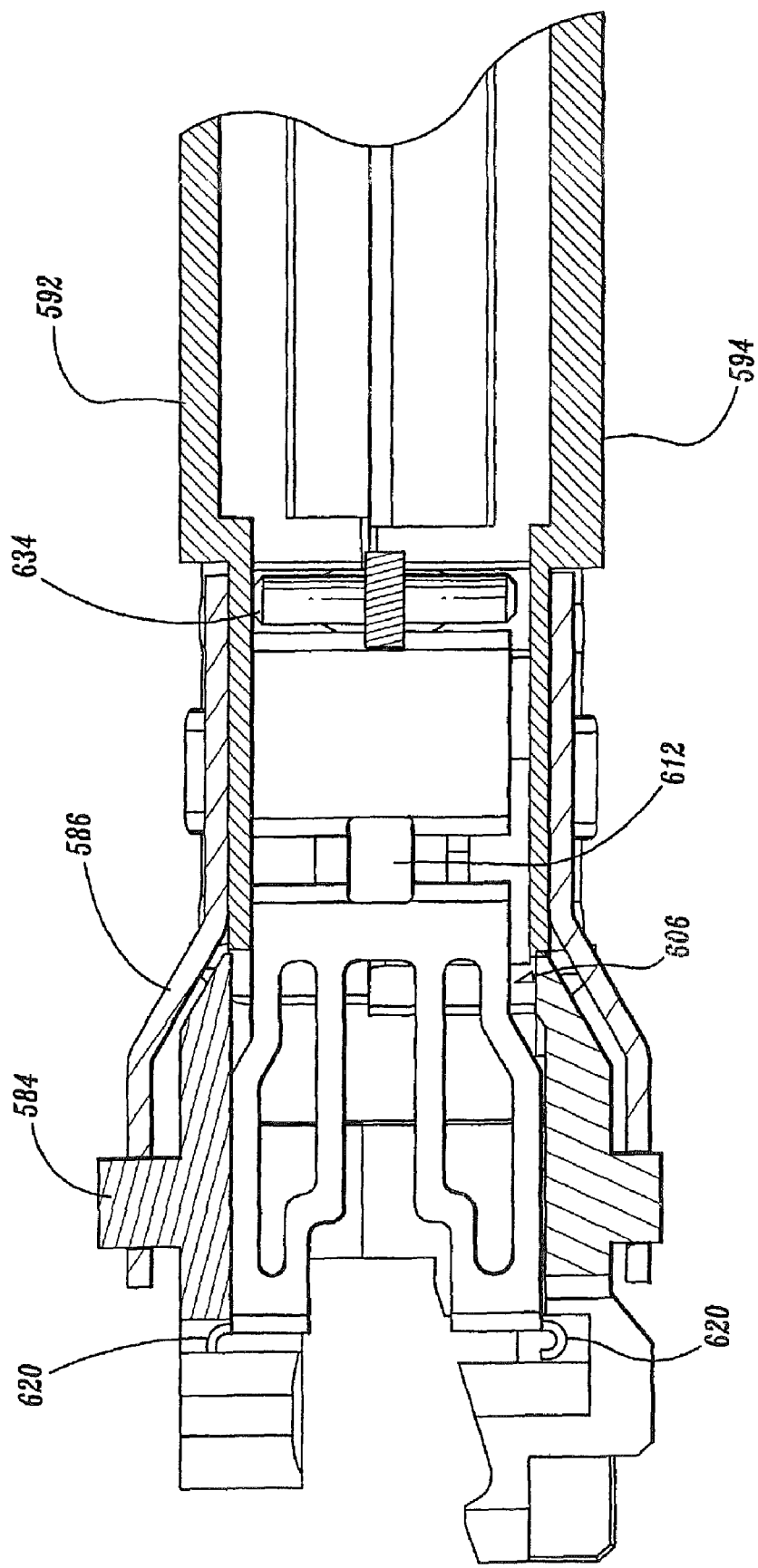
FIG. 83 is a side cross-sectional view of the proximal end of the tool assembly and the distal end of the proximal body portion of the disposable loading unit shown in FIG. 80.
Figure 85:
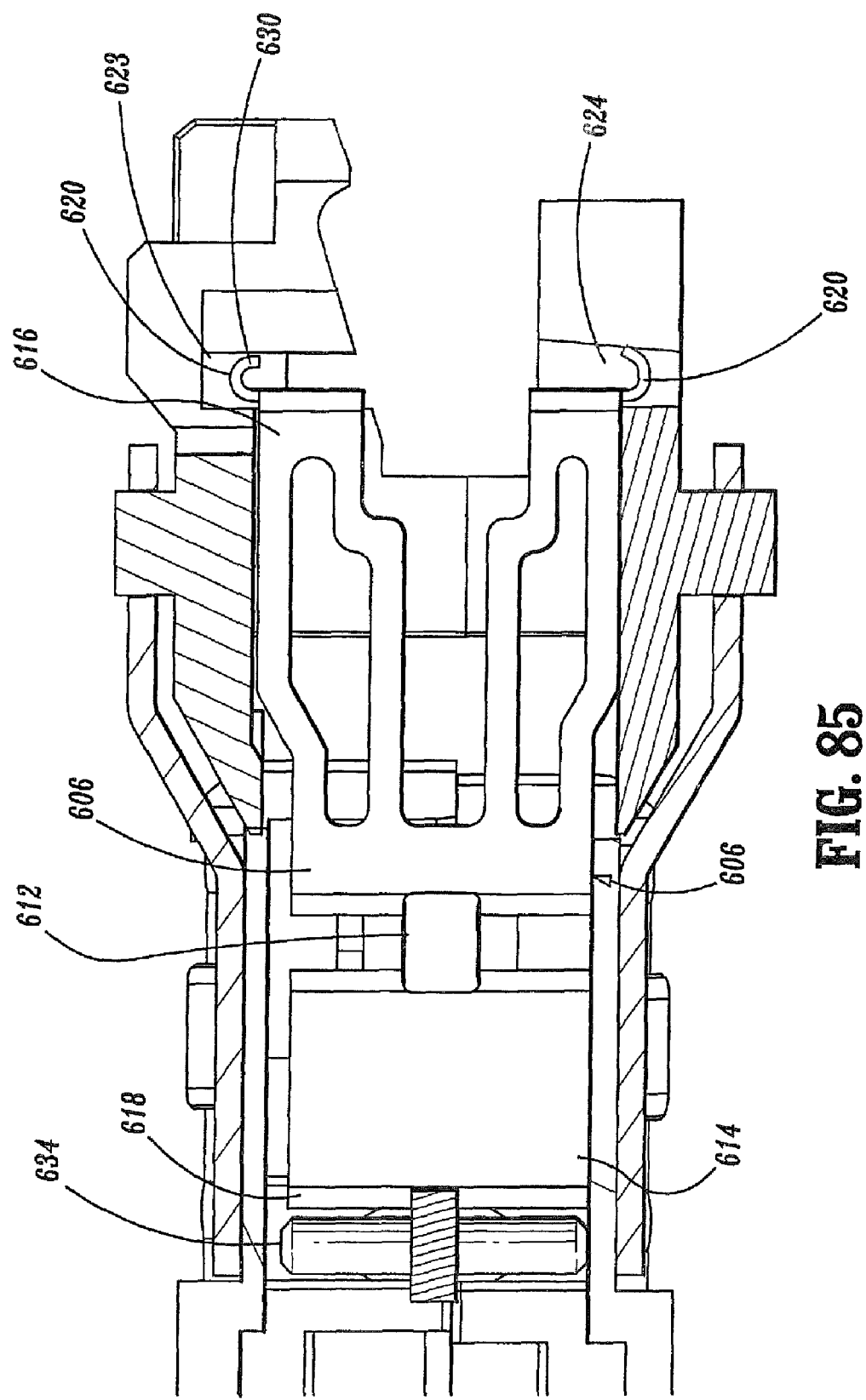
FIG. 85 is a side cross-sectional view of the proximal end of the tool assembly and the distal end of the proximal body portion of the disposable loading unit shown in FIG. 80.
Figure 86:
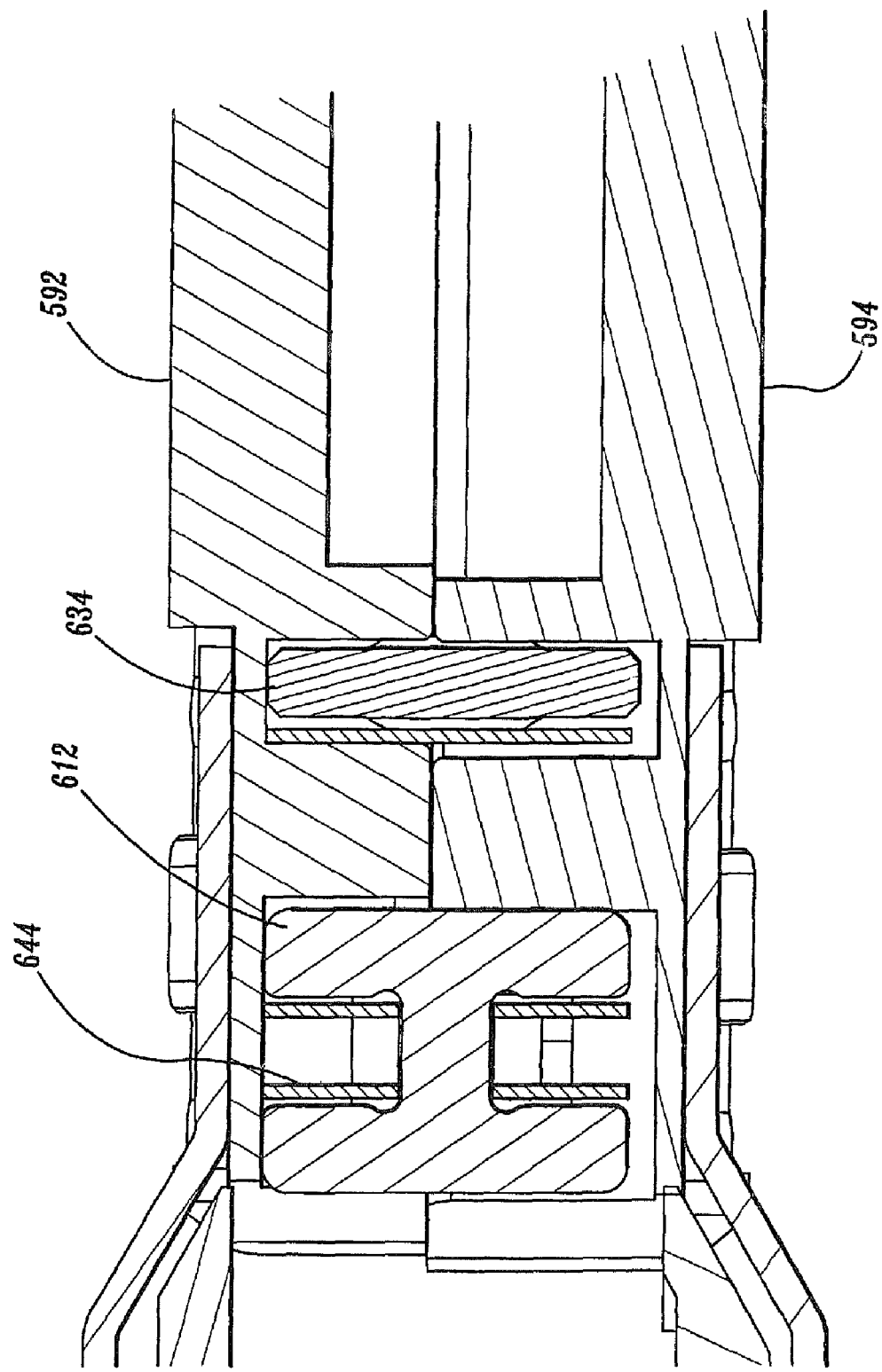
FIG. 86 is a transverse cross-sectional view of the proximal end of the tool assembly and the distal end of the proximal body portion of the disposable loading unit shown in FIG. 80.
Figure 87:
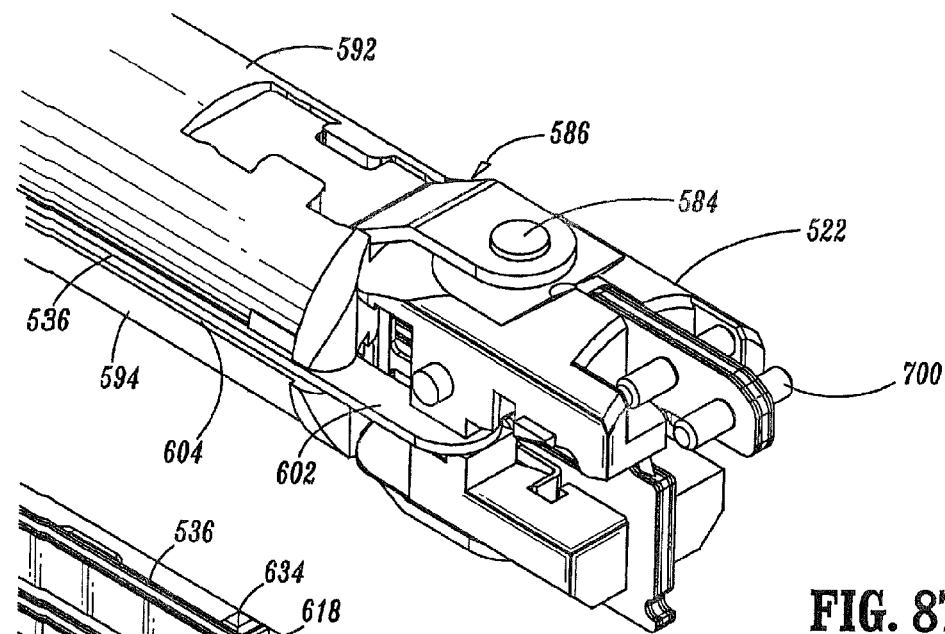
FIG. 87 is a perspective view of the distal end of the proximal body portion and the mounting assembly of the disposable loading unit shown in FIG. 80.
Figure 88:
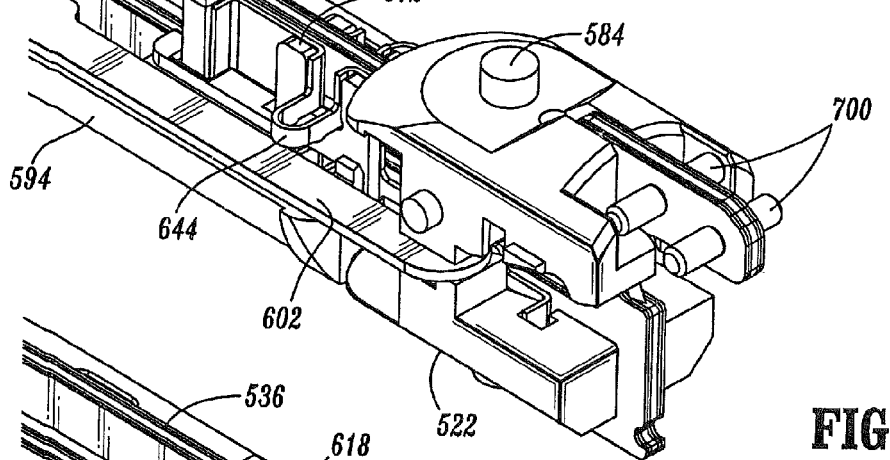
FIG. 88 is a perspective view of the distal end of the proximal body portion and mounting assembly of the disposable loading unit shown in FIG. 80 with the upper housing half removed.
Figure 89:
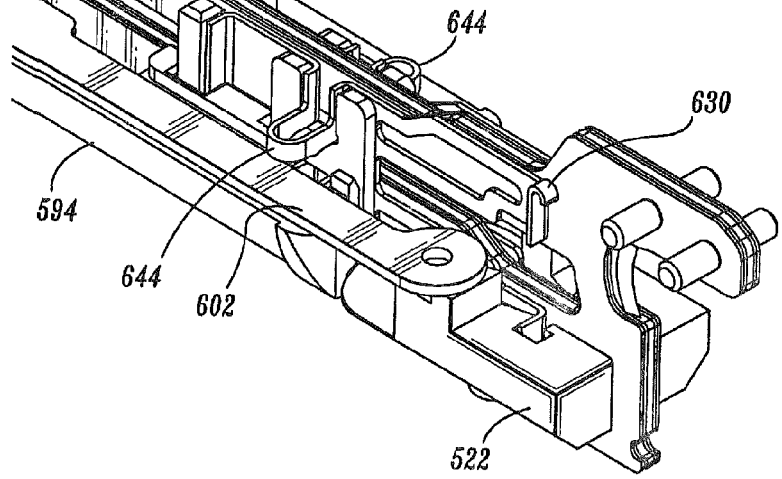
FIG. 89 is a perspective view of the distal end of the proximal body portion with the upper housing half section removed.
Figure 92:
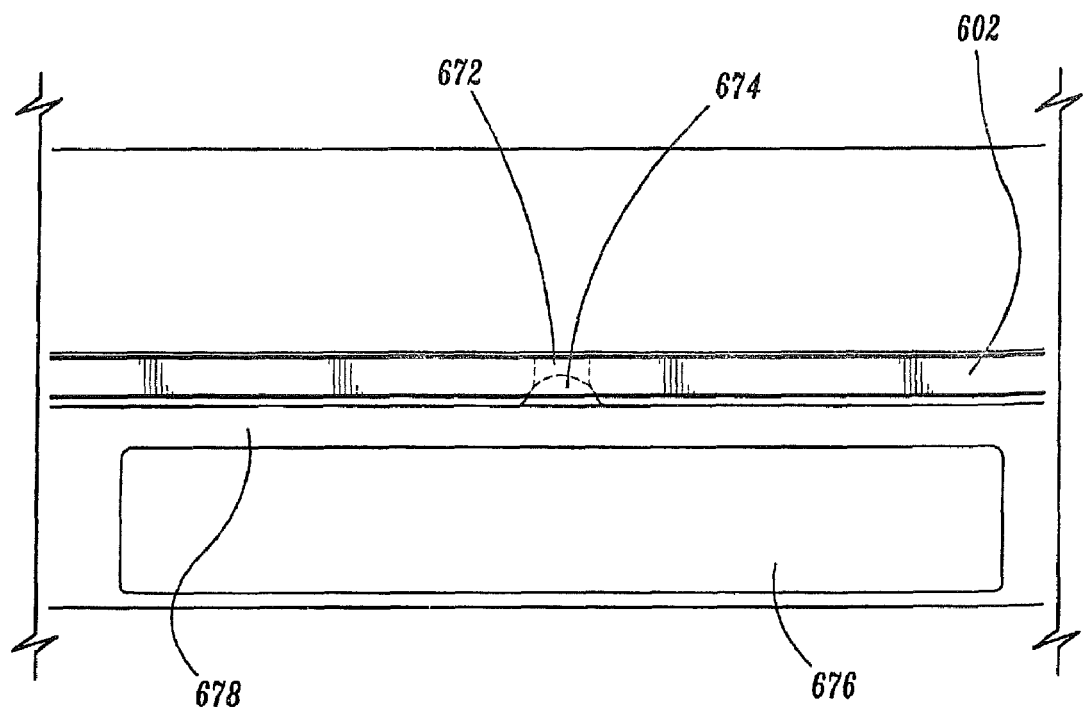
FIG. 92 is a side view of the upper housing half and the articulation link of the disposable loading unit shown in FIG. 80.
Figure 93:
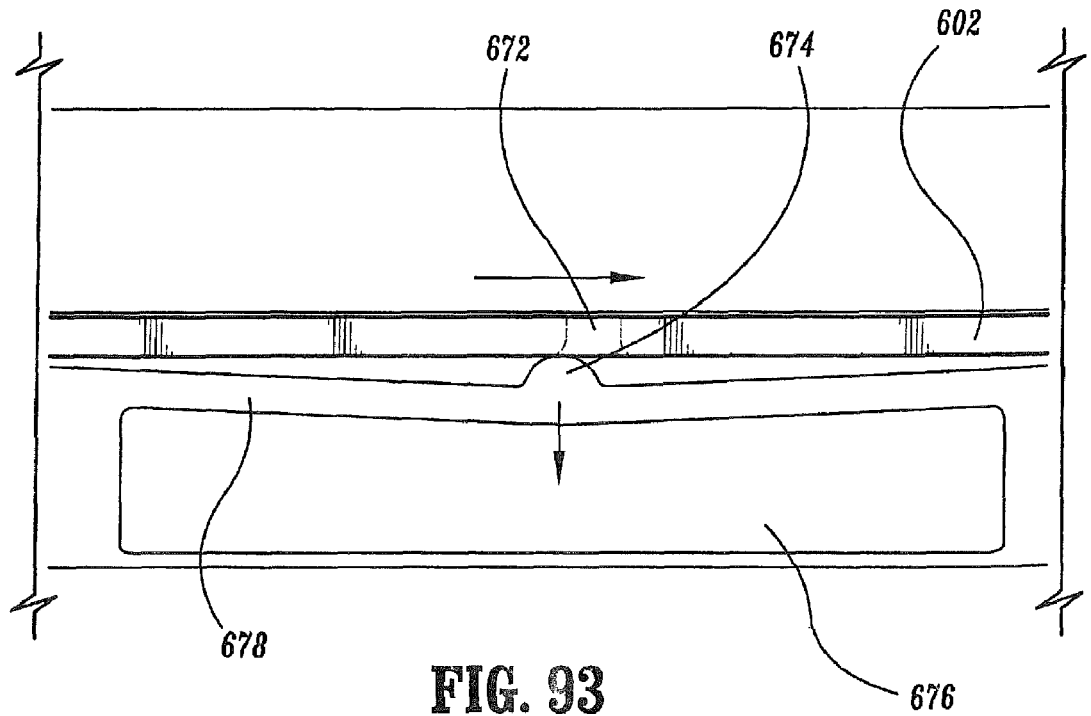
FIG. 93 is a side view of the upper housing half and articulation link of the disposable loading unit shown in FIG. 80 as the articulation link is advanced to articulate the tool assembly.

FIGS. 81-89 illustrate details of blowout plate assemblies 606. Each blow out plate assembly 606 includes a laterally flexible body 610 and an H-block 612. Flexible body 610 has a proximal end 614 and a distal end 616. The distal and proximal ends each include a retaining portion 618 and 620, respectively. Retaining portion 618 is configured to be and is fixedly received and engaged within recesses 621 and/or 622 formed in upper and/or lower housing halves 592 and 594 of DLU 16 (FIGS. 21, 82, 85). Retaining section 620 includes a pair of J-shaped attachment members configured to be and which are fixedly received and engaged within recesses 623 and 624 formed in upper and/or lower mounting portions 580 and 582 of mounting assembly 522. The tips 630 of J-shaped attachment members are angled to engage and lock into recesses 623 and 624 (FIG. 82), and are preferably press-fit into the walls that form the recesses.

A locking member 634 (FIGS, 84a-84c) includes an H-shaped body having a pair of legs 636 and a central web 638. Bach leg 636 includes an elongated retaining protrusion 640 having tapered ends. Locking member 634 is dimensioned to be and is press fit within recesses 621 and 622 formed in upper and lower housing halves 592 and 594 (FIG. 83) of DLU 16 (FIG. 21) adjacent retaining section 618 to fixedly secure retaining section 618 within the recesses. A central portion of blow out plate assembly 606 includes spring portion or section which preferably includes a pair of substantially U-shaped spring portions 644. U-shaped spring portion 644 allows the central portion of body 610 to lengthen axially and flex slightly outwardly relative to or of the longitudinal axis to accommodate sliding and articulating movement of drive assembly 536 (FIG. 80) including when tool assembly 20 (FIG. 21) is actuated, i.e., approximated or fired. By providing a support member which is capable of axially lengthening, binding of the drive assembly due to the difference in radius of curvature along the inner and outer surfaces of the drive assembly adjacent the pivot axis is substantially reduced.

As shown in FIG. 81, a limit member, which is preferably formed as an H-block 612, is positioned with a small gap about spring portions 644 to limit the extent to which U-shaped spring portions 644 are able to flex to prevent binding and/or buckling of the blow out plate assembly 606 and drive assembly 536 during actuation of device 510. A blow-out plate assembly 606 is positioned on each side of drive assembly 536 adjacent the pivot axis of tool assembly 512 to prevent outward buckling and/or binding of drive assembly 536 during actuation of device 510, including when device 510 is articulated.

Referring to FIGS. 80 and 87-93, an articulation link 602 includes at least one elongated metallic plate. Preferably, two or more metallic plates are stacked to form link 602. The proximal end of articulation link 602 includes a hook portion 660 configured to engage the articulation mechanism positioned within instrument 510 and the distal end includes a loop 662 dimensioned to engage a projection 664 formed on mounting portion 580 of mounting assembly 522. Projection 664 is laterally offset from pivot member 584 such that linear movement of articulation link 602 causes mounting assembly 522 to pivot about pivot members 584 to articulate tool assembly 20 (FIG. 21) in relation to proximal body portion 518.

Elongated body portion 14 (FIG. 1) or proximal body portion 518 may include a retaining member for preventing articulation of tool assembly 520 until a predetermined force has been applied to articulation link 602. Preferably, lower housing half 594 of proximal body portion 518 includes a recess 666 dimensioned to receive a biasing member 668, e.g., a compression spring, and a ball 670. Articulation member or link 602 includes a concavity 672 dimensioned to partially receive ball 670. Engagement between ball 670 and concavity 672 retains articulation link 602 in the unarticulated position Until it is desired to articulate the tool assembly. Referring to FIGS. 90-93, in an alternate embodiment, a spherical protrusion 674 is formed monolithically or integrally with lower housing half 594 and is dimensioned to be received within a recess, here shown as concavity 672, in articulation link 602. A cutout 676 is formed in lower housing half 594 such that protrusion 674 is supported on a flexible wall 678. When the tool assembly 520 is in the non-articulated position, protrusion 674 rests within concavity 672 to prevent movement of articulation link 602 (FIG. 91) unless a predetermined axial force is applied to link 602. When a sufficient or predetermined axial force is applied to link 602 and link 602 is moved linearly to articulate the tool assembly, flexible wall 678 flexes downwardly as illustrated in FIG. 21 to permit articulation link 602 to move-distally. It is envisioned that multiple protrusions may be provided on the housing to permit the tool assembly to be selectively retained at multiple articulated and non-articulated positions. Alternately, recesses may be formed in the housing and a protrusion may be provided on the articulation link. It is also envisioned that the above-disclosed retaining member(s) can be formed in elongated body portion 14 of the device.

Referring to FIGS. 80 and 94-96, axial drive assembly 536 includes an elongated drive beam 680 including a distal working head 682 (FIG. 80) and a proximal engagement section 684. Drive beam 680 may be constructed from a single sheet of material or, preferably, multiple stacked sheets. Engagement section 684 includes a pair of engagement fingers 686 which are dimensioned and configured to mountingly engage a pair of corresponding retention slots 688 formed in drive member 690. Drive member 690 includes a proximal porthole 692 configured to receive the distal end of a firing rod of an instrument 10 (FIG. 21) when the proximal end of disposable loading unit 512 is engaged with the elongated body of surgical stapling instrument 10.

The distal end of drive beam 680 is defined by a vertical support strut 694 which supports knife blade 578, and an abutment surface 696 which engages the central portion of actuation sled 234 (FIG. 22) during a stapling procedure. Surface 698 is located at the base of surface 696 and is configured to receive a support member (not shown) which is slidably positioned along the bottom of the staple cartridge assembly 22 (FIG. 22). Knife blade 578 is positioned to translate at a position slightly behind actuation sled 234 through a central longitudinal slot in staple cartridge assembly 22 to form an incision between rows of stapled body tissue. Retention flange 540 projects distally from vertical strut 694 and supports cylindrical cam rollers 700 at its distal end. Cam rollers 700 are dimensioned and configured to engage cam surface 209 on anvil body 204 to clamp anvil body 204 against body tissue.

Referring to FIGS. 80 and 93-96, a locking member 702 is supported on the proximal end of drive beam 680. Locking member 702 has a generally H-shaped configuration including first and second legs 704 and 706, a cross-over portion 708, and a pair of arms 710. Each leg 704 and 706 includes a lateral protrusion 712. Cross-over portion 708 is positioned within a slot 714 formed in drive beam 680 of drive assembly 536. Protrusions 712 are received within recesses 716 formed in lower housing half 594. When drive assembly is actuated by applying a predetermined force to movable handle 28 to advance drive beam 680 distally, protrusions 712 are forced from recesses 716 to provide an audible and tactile indication that instrument 510 has been actuated. Locking member 702 also prevents inadvertent partial actuation of DLU 512, such as during shipping, by locking drive beam 680 at a fixed position within DLU 512 until a predetermined axial force has been applied to the drive beam 680, Sequence Of Operation A. Attachment of DLU Referring to FIGS. 20 and 40-48, to use stapling device 10, a DLU 16 is first secured to the distal end of elongated body 14. To secure DLU 16 (FIG. 41) to elongated body 14 (FIG. 40), insertion tip 193 of DLU 16 is positioned about the distal end 276 of firing rod 58 and moved axially in the direction indicated by arrow "A" in FIGS. 42 and 43. A channel (not shown) formed in the distal end of elongated body 14 is provided for slidably receiving hook portion 258 of second articulation link 256. Lugs 254 will also be positioned within channels (not shown) in the distal end of elongated body 14. As insertion tip 193 advances into elongated body 14, one of lugs 254 engages engagement finger 190a of lock button 190 to move lock button 190 proximally against the bias of spring 194 in the direction indicated by arrow "B" in FIGS. 43 and 44 within elongated body 14. As lock button 190 moves proximally, abutment surface 190b engages plate 192a of plate and spring assembly 192 to urge blocking portion 192b of plate 192 in the direction indicated by arrow "C" in FIG. 44 into notch 196 formed in firing rod 58 (FIG. 44). Positioning of blocking portion 192b in notch 196 of firing rod 58 prevents stapling device 10 from being actuated, i.e., approximated or fired, until DLU 16 has been rotated to a locked position.

Referring to FIG. 45, to lock DLU 16 in position on elongated body 14, DLU 16 and/or body 14 is rotated in relation to the other in the direction indicated by arrow "D" in FIG. 45, to move nub 254 out of alignment with finger 190a of lock button 190. When this occurs, lock button 190 is moved distally by spring 194 in the direction indicated by arrow "E" in FIG. 48 to allow blocking portion 192b of plate 192a to be moved by spring 192c in the direction indicated by arrow "F" in FIG. 48 out of notch 196 of firing rod 58. Finger 190a is moved to a position to the side of nub 254 to lock DLU 16 on elongated body 14. To remove DLU 16 from elongated body after it has been locked in position, lock button 190 must be manually moved proximally and this can only be done with firing rod 58 in the retracted position. As illustrated in FIG. 46, when DLU 16 is locked onto elongated body 14, engagement structure 160 of articulation link 130 is operably engaged with hook portion 258 of second articulation link 256.

B. Operation of the Sensor Mechanism

Referring now to FIGS. 44 and 49-52, when DLU 16 is inserted into elongated body 14 in the direction indicated by arrow "A" in FIG. 44, tip 193 of DLU 16 engages the distal end 170a of sensor plate 170 to move sensor plate 170 proximally in the direction indicated by arrow "G" in FIG. 44. Proximal end 170b of sensor plate 170, in turn, forces sensor cap 174 to move proximally in the direction indicated by arrows "H" in FIGS. 49 and 50. Flange 174b of sensor cap 174 is engaged with rack lock release member 172 such that rack lock release member 172 is moved proximally in the direction indicated by arrow "I" in FIG. 51 into engagement with rack lock 64. Engagement between rack lock release member 172 and rack lock 64 causes rack lock 64 to rotate in the direction indicated by arrow "J" in FIG. 51 to move blocking portion 64a of rack lock 64 to a position no longer obstructing engagement between pawl 48 and toothed rack 60 of actuation shaft 52, and to move locking portion 64b of rack lock 64 out of recess 52a of actuation shaft 52. Movement of sensor cap 174 proximally also moves sensor cap tab 174a in the direction indicated by arrow "K" in FIG. 52 from cam member cutout 176 to enable operation of the articulation mechanism of surgical stapling device 10.

Figure 42A:
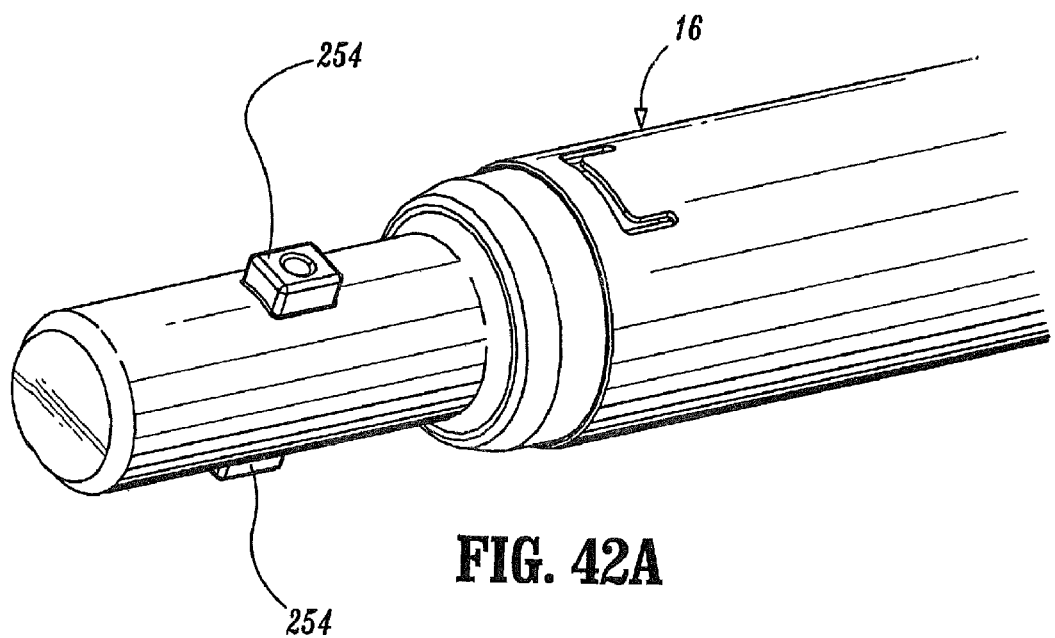
FIG. 42a is an enlarged perspective view of the proximal end of the disposable loading unit shown in FIG. 21.
Figure 52A:
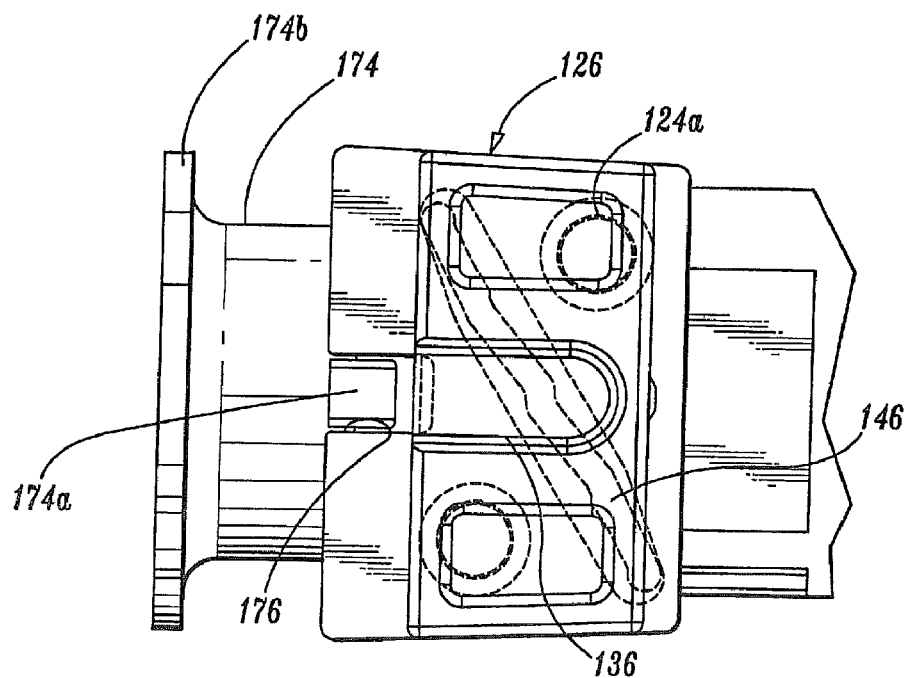
FIG. 52A is a top view of the cam cover and cam member assembly and sensor cap prior to attachment of a disposable loading unit to the elongated body portion of the surgical stapling device.
Figure 53:
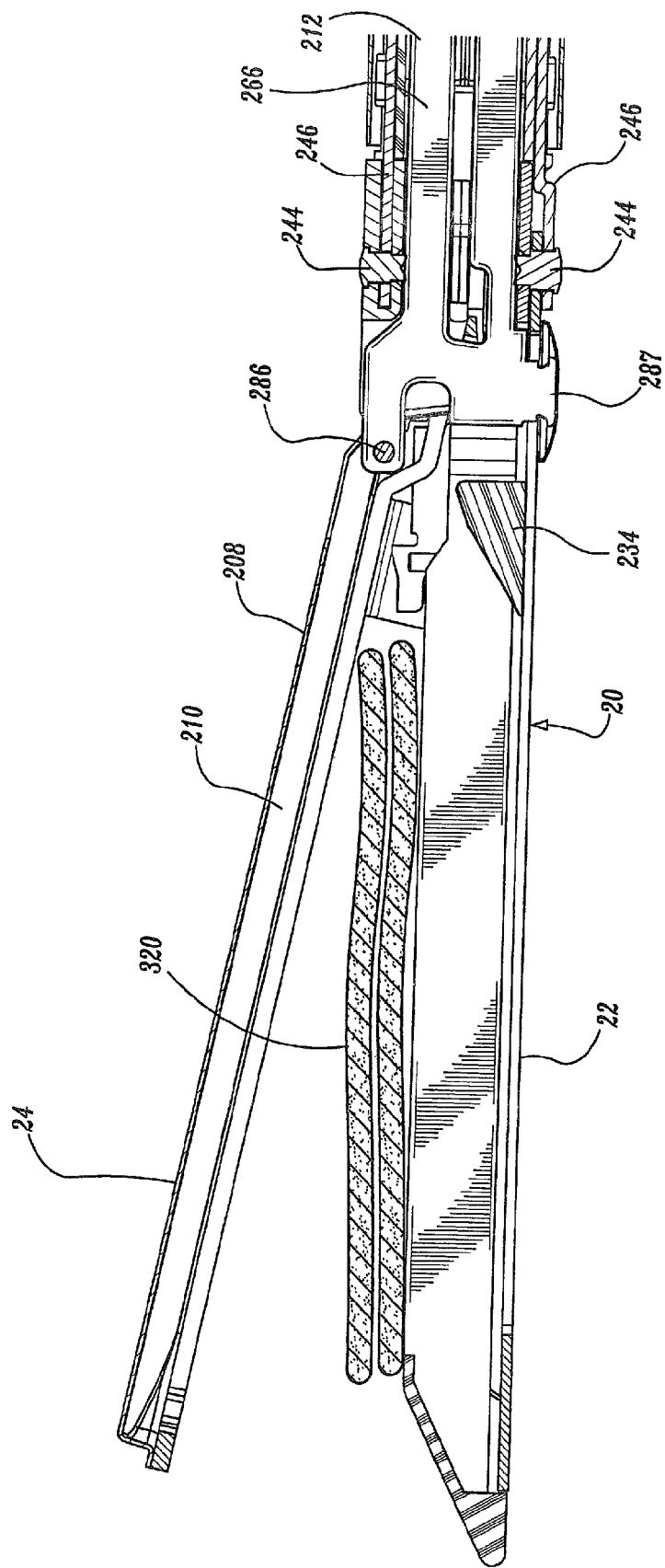
FIG. 53 is a side cross-sectional view of the tool assembly of the surgical stapling device shown in FIG. 2 in the unapproximated position.

Referring to FIGS. 42A and 52A, as discussed above, stapling device 10 is usable with both articulating and non-articulating DLU's. A non-articulating DLU 16a (FIG. 42A) does not include insertion tip 193 (See FIG. 42). As such, the sensor mechanism including sensor plate 170, sensor cap 174 and lock release member 172 are moved proximally a lesser distance when DLU 16a is attached to elongated body 14. The distance the sensor mechanism is moved proximally is sufficient to disengage rack lock release member 172 from actuation shaft 52 but is insufficient to move tab 174a from cutout 176 (FIG. 52A).

Referring to FIGS. 47-49, when a DLU is secured to surgical stapling device 10, vertical pawl 66 is positioned beneath an abutment surface 52a formed on actuation shaft 52 and is urged to the retracted position. As illustrated in FIG. 50, in this position, cam surfaces 80 of vertical pawl 66 are positioned below cam member 76 of plunger 72. Surgical stapling device 10 is now ready to be approximated about tissue 320 (FIG. 45).

C. Approximation

Figure 54:
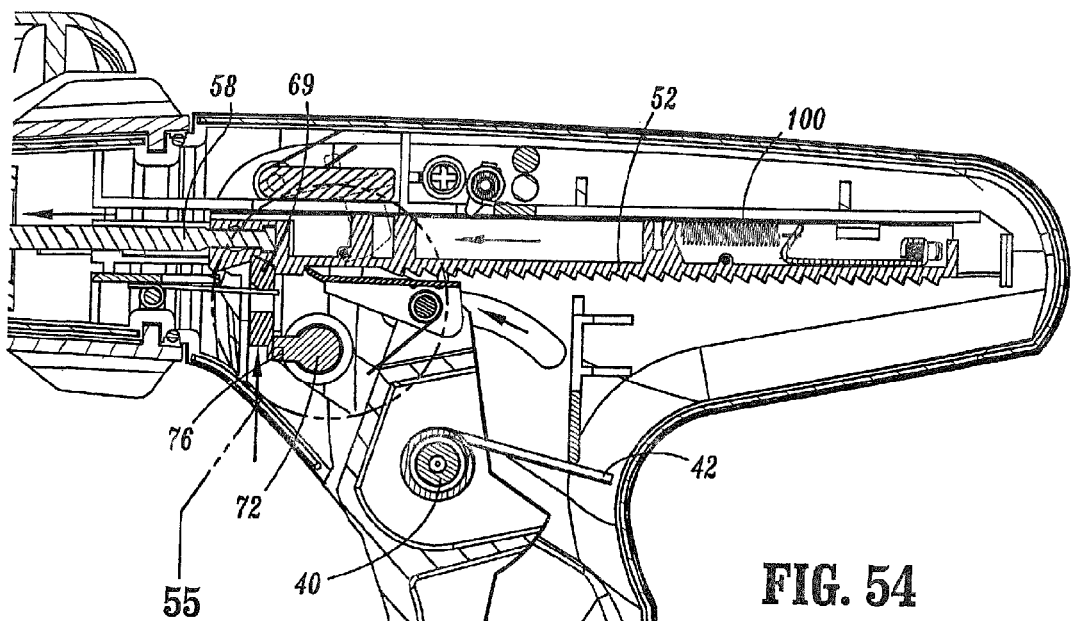
FIG. 54 is a side cross-sectional view, with portions broken away, of the handle assembly of the surgical stapling device shown in FIG. 2 during approximation of the surgical stapling device.
Figure 55:
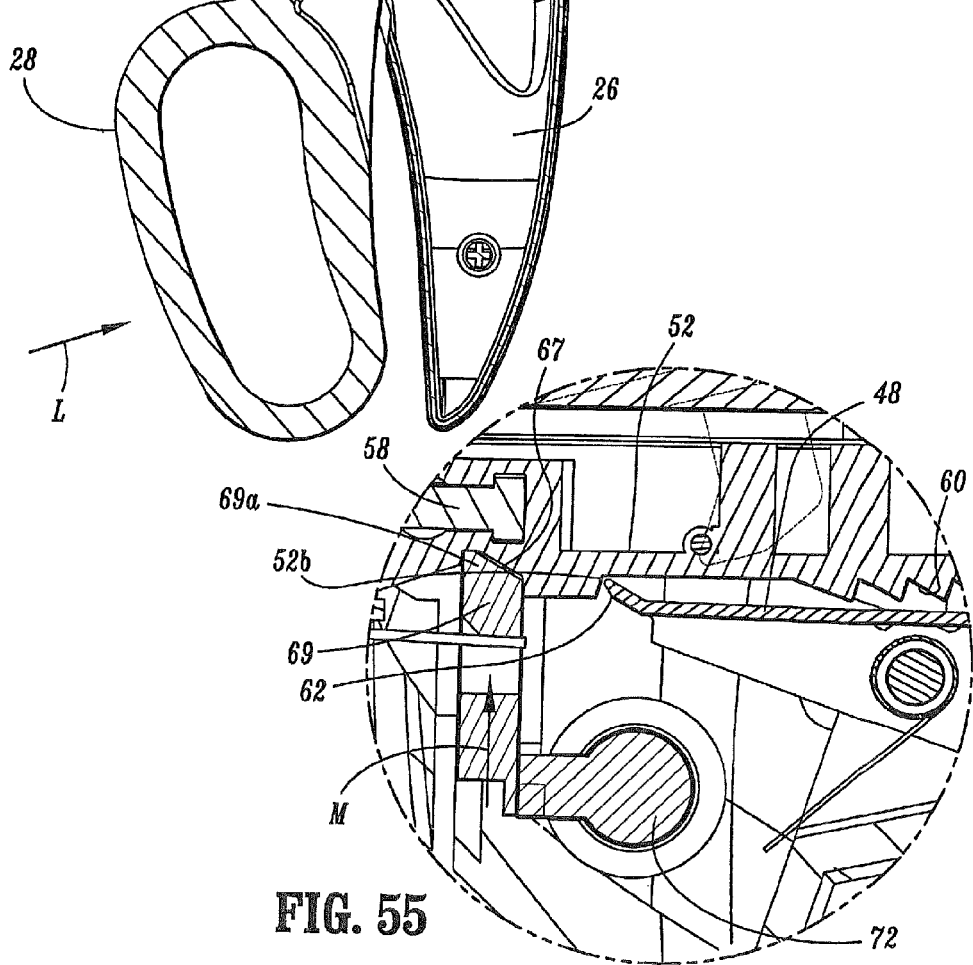
FIG. 55 is an enlarged view of the indicated area of detail shown in FIG. 54.

Referring to FIGS. 54 and 55, to approximate the cartridge and anvil assemblies 22 and 24, movable handle 28 is moved in the direction indicated by arrow "L" in FIG. 54 through an actuation stroke, i.e., movable handle 28 is compressed towards stationary handle 26 against the bias of torsion spring 42 to move engagement finger 62 of pawl 48 into engagement with a shoulder 52b formed on actuation shaft 52. Subsequent movement of movable handle 28 through the actuation stroke effects advancement of actuation shaft 52 and firing rod 58. As actuation shaft 52 is advanced, notch 67 formed in actuation shaft 52 moves into alignment with vertical pawl 69 and vertical pawl 69 is urged by spring member 70 in the direction indicated by arrow M in FIG. 55 into notch 67 to prevent further advancement of actuation shaft 52 (FIG. 55).

Referring to FIGS. 56 and 57, firing rod 58 is connected at its distal end to axial drive assembly 212 including drive beam 266, such that advancement of firing rod 58 effects advancement of drive beam 266 in the direction indicated by arrow "N" in FIGS. 56 and 57. As drive beam 266 is advanced, cam roller 286 moves into engagement with cam surface 209 of anvil portion 204 (FIG. 22) to urge anvil portion 204 in the direction indicated by arrow "O" in FIG. 57 to approximate cartridge and anvil assemblies 22 and 24 and clamp tissue 320 therebetween.

Referring to FIGS. 58 and 59, after movable handle 28 is actuated to approximate cartridge and anvil assemblies 22 and 24, biasing member 42 returns handle 28 in the direction indicated by arrow "P" in FIG. 58 to its non-compressed position spaced from stationary handle 26. As illustrated, in this position, vertical pawl 69 is in the extended position with tip 69a located within notch 67 of actuation shaft 52, thus preventing further advancement of actuation shaft 52. In the extended position, cam surfaces 80 on vertical pawl 69 are aligned with cam member 76 of plunger 72 (See FIG. 59).

D. Operation of the Plunger

Referring to FIGS. 60-62, when stapling device 10 is approximated, vertical pawl 69 is engaged within notch 67 of actuation shaft 52 to lock actuation shaft 52 in the approximated position. To release or unlock the actuation shaft 52 and put stapling device 10 in a fire-ready position, plunger 72 is provided. When plunger 72 is pressed in the direction indicated by arrow "Q" in FIG. 61, cam member 76 of plunger 72 engages cam surfaces 80 of vertical pawl 69 to urge vertical pawl 69 in the direction indicated by arrow "R" in FIG. 61 to its retracted position. In the retracted position, tip 69a of vertical pawl 69 is outside of notch 67 of actuation shaft 52 and device 10 is in a fire-ready position. Vertical pawl 69 is maintained in the retracted position by engagement between cam member 76 of plunger 72 and recesses 82 on cam surfaces 80 of vertical pawl 69.

E. Firing the Surgical Stapling Device

Referring to FIGS. 63-65, to fire stapling device 10, movable handle 28 is moved in the direction indicated by arrow "L" in FIG. 63 through a second actuation stroke during which, engagement finger 62 of pawl 48 engages toothed rack 60 of actuation shaft 52 to advance actuation shaft 52 and firing rod 58 distally. Referring again to FIG. 60, as actuation shaft 52 moves distally, a second abutment surface 52b formed on actuation shaft engages vertical pawl 69 to move vertical pawl 69 downwardly in the direction indicated by arrow "R" in FIG. 64 to disengage cam member 76 of plunger 72 from cam surface 80 of vertical pawl 69 and allow spring 78 to return plunger 72, in the direction indicated by arrow "S" in FIG. 64, to the neutral position.

Referring to FIGS. 66 and 67, as firing rod 58 is advanced in the manner discussed above, drive beam 266 is advanced in the direction indicated by arrow "T" in FIGS. 66 and 67 to advance actuation sled 234 through staple cartridge 22 to simultaneously sever tissue with knife 280 (FIG. 31) and drive pushers 228 to sequentially eject staples 226 from the cartridge.

Surgical stapling device 10 is adapted to receive DLU's having staple cartridges with staples in linear rows having a length of from about 30 mm to about 60 mm. Each actuation stroke of movable handle 28 during firing of surgical stapling device 10 advances actuation shaft 52 approximately 15 mm, although other lengths are envisioned. Accordingly, to fire a cartridge having a 45 mm row of staples, movable handle 28 must be moved through three actuation strokes after the approximating or clamping stroke of movable handle 28.

F. The Retraction Mechanism

Figure 68:
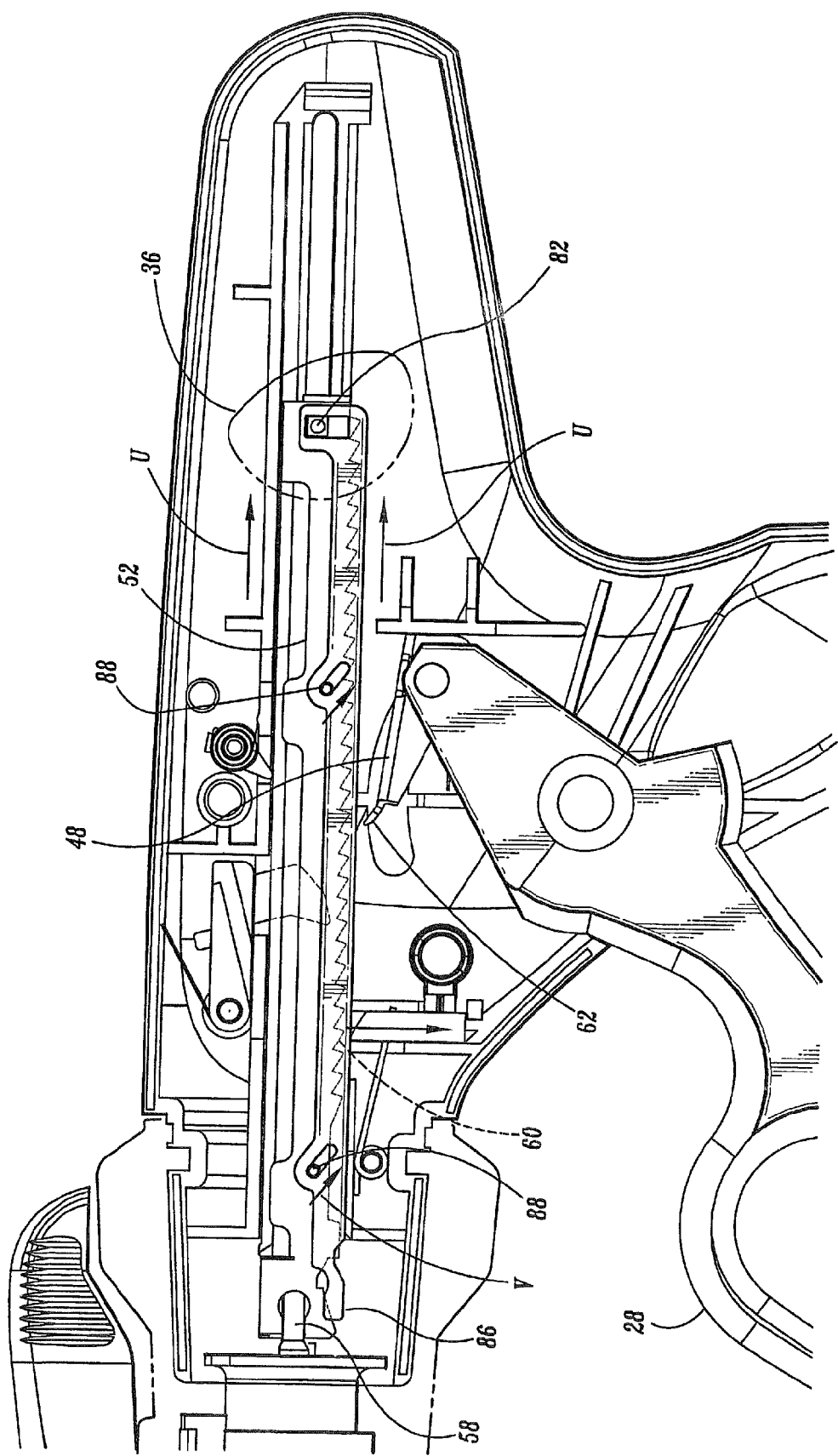
FIG. 68 is a side view of the handle assembly of the surgical stapling device shown in FIG. 2 during retraction of the actuation shaft.

FIG. 68 illustrates operation of the retraction mechanism of surgical stapling device 10. In use, when return knobs 36 are pulled rearwardly by a surgeon in the direction indicated by arrow "U" in FIG. 68, coupling rod 82 initially moves release plate 86 rearwardly in relation to actuation shaft 52 as rod 82 slides in slots 84 of actuation shaft 52 such that pins 88 cam release plate 86 downwardly in the direction indicated by arrow "V" to a position covering toothed rack 60 of actuation shaft 52 and disengaging finger 62 of pawl 48 from toothed rack 60. When coupling rod 82 is pulled rearwardly to a position at which it engages the back end 84a (FIG. 5A) of slots 84, additional rearward movement knobs 36 will effect proximal movement of actuation shaft 52 and firing rod 58.

G. Operation of the Articulation Mechanism

Referring to FIGS. 69-72, articulation lever 122 is pivotable to effect articulation of tool assembly 20. More specifically, when articulation lever 122 is rotated or pivoted about lever pin 132 (FIG. 12), projection 134 (FIG. 11) of lever 122 causes cam cover 126 and cam member 124 to move across transverse channel 120 of rotatable knob 32, Movement of cam member 124 across transverse channel 124 causes stepped cam slot 146 to move in relation to first projection 150 of cam pin 148, thus causing cam pin 148 to move through longitudinal slot 144 in rotatable knob 32. (FIG. 11). Longitudinal movement of cam pin 148 effects corresponding longitudinal movement of drive member 128 and articulation link 130. As illustrated in FIG. 69 when lever 122 is rotated in a counter-clockwise direction, articulation link 130 is moved proximally or retracted. As illustrated in FIG. 70, when lever 122 is rotated in a clockwise direction, articulation link 130 is moved distally or advanced, As illustrated in FIGS. 71-73, the distal end of articulation link 130 is operably connected to the proximal end of second articulation link 256. The distal end of articulation link 256 is connected to projection 262 on mounting assembly 200 (FIG. 73). Projection 262 is laterally offset from pivot members 244 such that movement of articulation link 256 causes articulation of tool assembly 20. More specifically, when articulation link 130 is retracted (FIG. 69), articulation link 256 is retracted and tool assembly 20 is articulated in a direction indicated by arrow "X" in FIG. 75. When articulation link 130 is advanced (FIG. 70), articulation link 256 is also advanced and tool assembly 20 is articulated in a direction indicated by the arrow "Y" in FIG. 74.

Referring to FIGS. 76 and 77, rotation knob 32 is rotatable in relation to handle assembly 12 to rotate elongated body 14 and DLU 16, including tool assembly 20, about a central longitudinal axis of elongated body 14. As illustrated in FIGS. 76 and 77, surgical stapling device 10 can be rotated while tool assembly 20 is articulated. Device 10 can also be rotated and then articulated.

H. Operation of Lockout Mechanism

Figure 37:
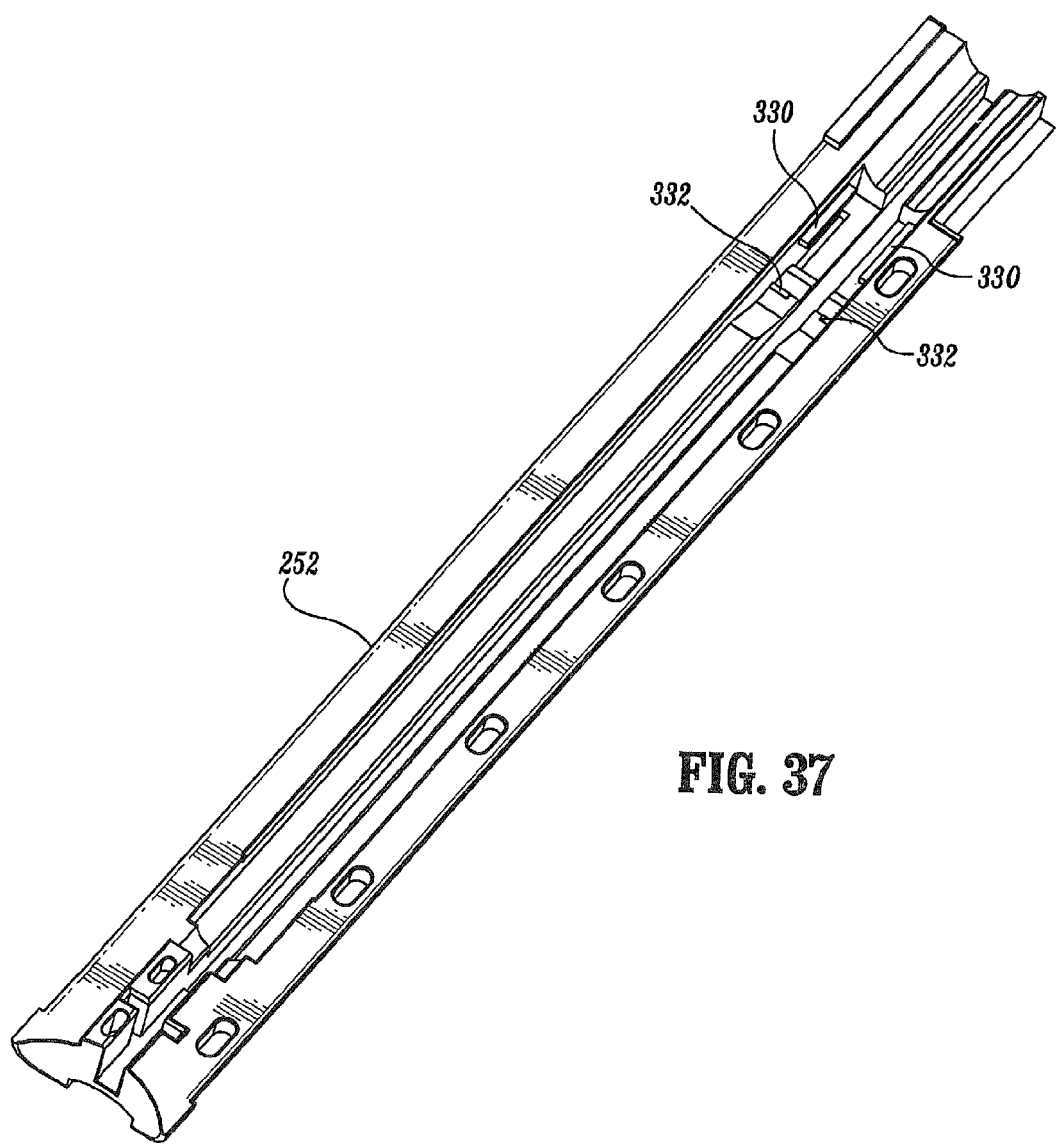
FIG. 37 is an enlarged perspective view of a lower housing half of the proximal body portion of the disposable loading unit shown in FIG. 21.

Referring now to FIGS. 36-38, 78 and 79, the sequence of lockout operation will be described in detail. In. FIG. 38, lockout device 288 is shown in its prefired position with horizontal cams 300 and 302 resting on top of projections 330 (FIG. 36) formed in the sidewalls of lower housing half 252 (FIG. 37). In this position, locking device 288 is held up out of alignment with projection 332 (FIG. 37) formed in the bottom surface of lower housing half 252, and web 298 is in longitudinal juxtaposition with shelf 334 (FIG. 38) defined in drive beam 266. This configuration permits the anvil 24 (FIG. 39) to be opened and repositioned onto the tissue to be stapled until the surgeon is satisfied with the position without activating locking device 288 to disable the disposable loading unit 16.

As shown in FIG. 72, upon distal movement of drive beam 266, locking device 288 rides off of projections 330 (not shown) and is biased into engagement with base lower housing half 252 by spring 304, distal to projection 332. Locking device 288 remains in this configuration throughout firing of the apparatus.

Figure 78:
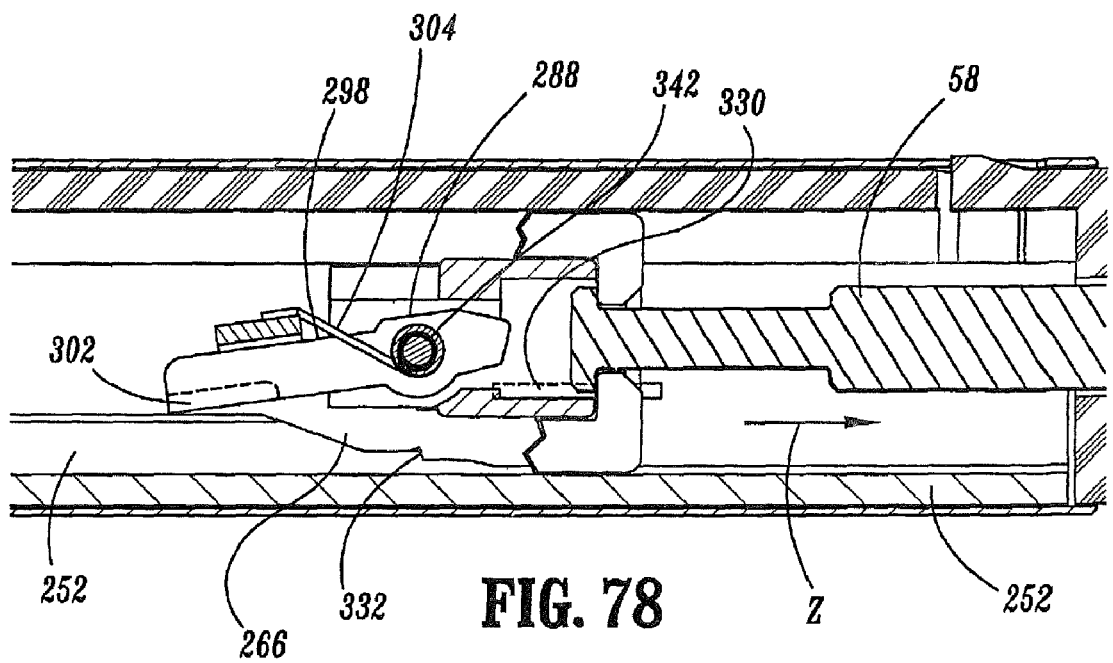
FIG. 78 is a side partial cross-sectional view of a portion of the disposable loading unit shown in FIG. 21 during retraction of the locking device.
Figure 79:
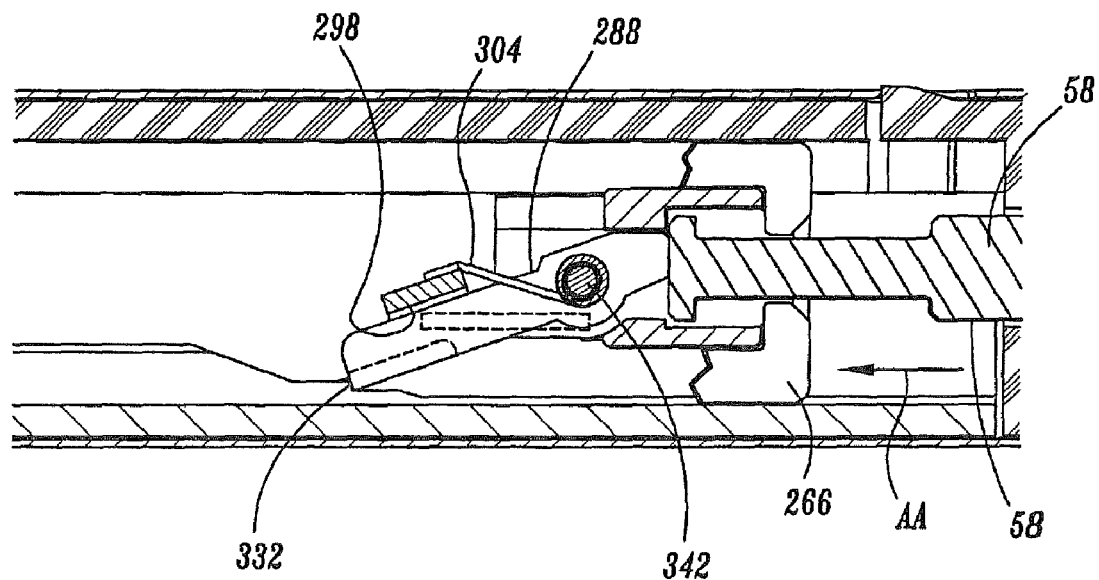
FIG. 79 is a side partial cross-sectional view of a portion of the disposable loading unit shown in FIG. 21 with the locking device in the locked position.
Figure 80:
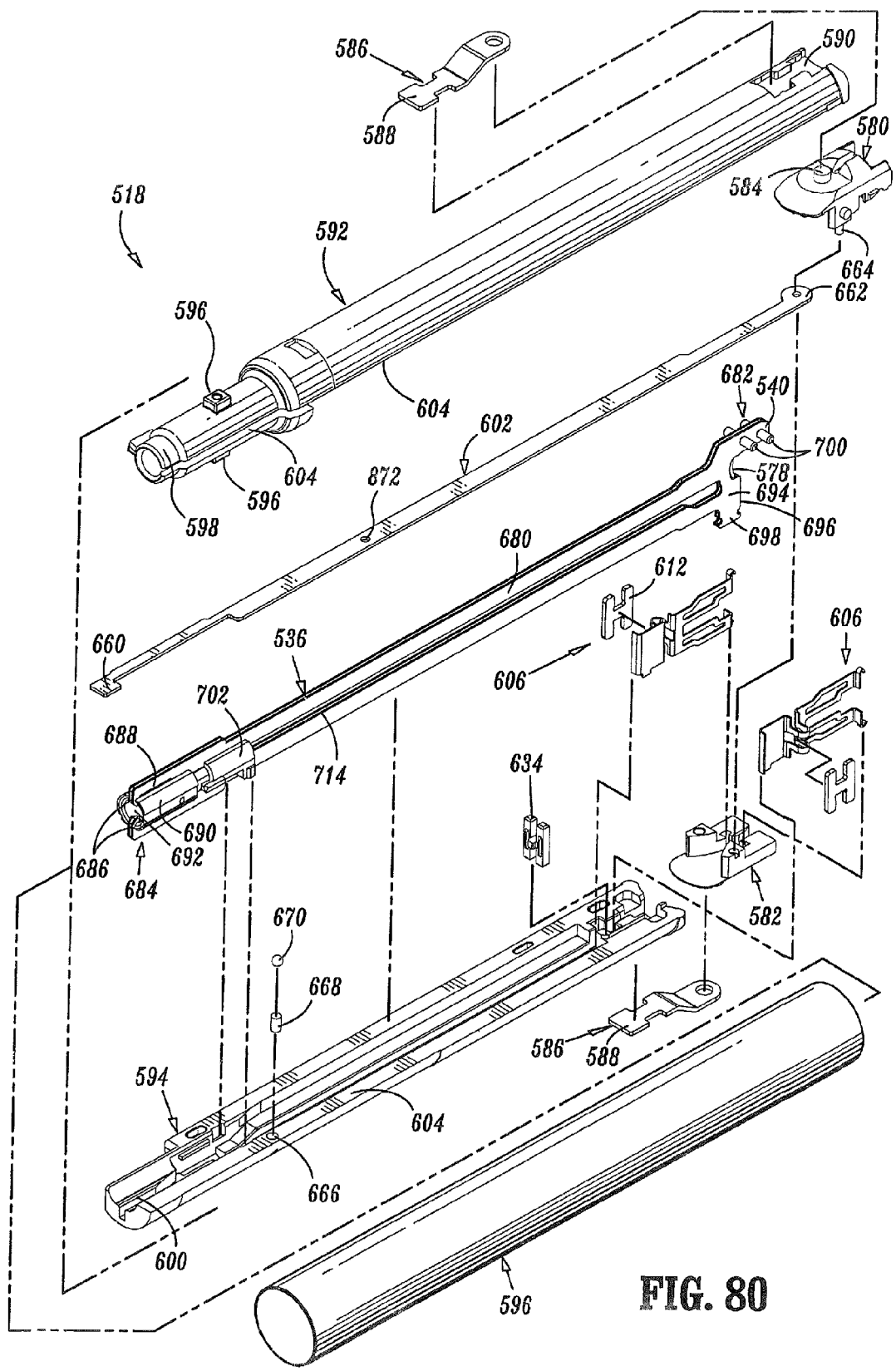
FIG. 80 is an enlarged exploded perspective view of the proximal body portion and mounting assembly of another preferred embodiment of the disposable loading unit.

Upon retraction of the drive beam 266 in the direction indicated by arrow "U" in FIG. 78, locking device 288 passes over projections 330 and rides over projection 332 until the distalmost portion of locking device 288 is proximal to projection 332. Spring 304 biases locking device 288 into juxtaposed alignment with projection 332, effectively disabling the disposable loading unit. If an attempt is made to reactuate the apparatus, the firing rod 58 will abut a proximal end surface of locking device 288 which surface is diagonally sloped to impart a moment about pivot pin 342 such that the distal end of locking device 288 is rotationally urged into contact with projection 332. Continued distal force in the direction indicated by arrow "AA" in FIG. 79, will only serve to increase the moment applied to the locking device thus the locking device will abut projection 332 and inhibit distal movement of the firing rod 58.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical stapling device comprising:
   an elongated body portion defining a longitudinal axis, and having proximal and distal ends, the elongated body including at least one housing half defining a recess;
   a tool assembly pivotally supported at the distal end of the elongated body portion about a pivot axis which is substantially perpendicular to the longitudinal axis of the elongated body, the tool assembly including a cartridge assembly housing a plurality of staples and an anvil assembly, the anvil assembly and the cartridge assembly having open and closed positions;
   a flexible drive assembly having a distal end configured to translate through the cartridge assembly to eject the staples therefrom, the flexible drive assembly being bendable relative to the longitudinal axis when the tool assembly pivots;
   a first support member positioned adjacent the pivot axis on a side of the flexible drive assembly, the first support member having a first end disposed in the recess in the housing half and fixedly attached to the housing half, wherein the first end of the first support member includes a retaining portion having a J-shaped attachment member to engage a recess in the tool assembly; and
   a locking member press fit in the recess in the housing half.

2. A surgical stapling device according to claim 1, further comprising a second support member adjacent the flexible drive assembly.

3. A surgical stapling device according to claim 1, wherein the first support member has a U-shaped portion that flexes when the tool assembly pivots.

4. A surgical stapling device according to claim 1 wherein the first support member is laterally flexible.

5. A surgical stapling device according to claim 1, wherein the attachment member has tips that are angled to engage and lock into the recess.

6. A surgical stapling device according to claim 1, wherein the tool assembly includes a pivot member, the pivot member defining the recess in the tool assembly.

7. A surgical stapling device according to claim 1, wherein the locking member has an H-shaped body.

8. A surgical stapling device according to claim 7, wherein the locking member includes an elongated retaining protrusion arranged so that the locking member is press fit within the recess of the housing half.

* * * * *